United States Patent
Craig

(10) Patent No.: US 9,670,503 B2
(45) Date of Patent: Jun. 6, 2017

(54) PIGGYBAC TRANSPOSON VARIANTS AND METHODS OF USE

(71) Applicant: The Johns Hopkins University, Baltimore, MD (US)

(72) Inventor: Nancy Lynn Craig, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 111 days.

(21) Appl. No.: 14/038,132

(22) Filed: Sep. 26, 2013

(65) Prior Publication Data

US 2014/0065124 A1 Mar. 6, 2014

Related U.S. Application Data

(63) Continuation of application No. 13/203,393, filed as application No. PCT/US2010/025386 on Feb. 25, 2010, now abandoned.

(60) Provisional application No. 61/155,207, filed on Feb. 25, 2009.

(51) Int. Cl.
*C12N 15/90* (2006.01)
*A61K 48/00* (2006.01)
*C12N 15/85* (2006.01)

(52) U.S. Cl.
CPC ............ *C12N 15/85* (2013.01); *C12N 15/90* (2013.01); *A61K 48/00* (2013.01); *C12N 2800/00* (2013.01)

(58) Field of Classification Search
None
See application file for complete search history.

(56) References Cited

U.S. PATENT DOCUMENTS

2007/0204356 A1 8/2007 Fraser
2009/0042297 A1 2/2009 George, Jr. et al.

OTHER PUBLICATIONS

Wilson et al., "PiggyBac Transposon-mediated Gene Transfer in Human Cells", The American Society of Gene Therapy, vol. 15, No. 1, pp. 139-145 (2007).
Ray et al., "Multiple waves of recent DNA transpoon activity in the bat, *Myotis lucifugus*", Genome Research, vol. 18, pp. 717-728 (2008).
Ding et al., "Efficient Transposition of the piggyBac (PB) Transposon in Mammalian Cells and Mice", Cell, vol. 122, pp. 473-483 (2005).
Wu et al., "piggyBac is a flexible and highly active transposon as compared to Sleeping Beauty, ToI2, and Mos1 in mammalian cells", PNAS, vol. 103, No. 41, pp. 15008-15013 (2006).
Cadinanos et al., "Generation of an inducible and optimized piggyBac transposon system", Nucleic Acids Research, vol. 35, No. 12, doi:10.1093/nar/gkm446 (2007).
Wang et al., "Chromosomal transposition of PiggyBac in mouse embryonic stem cells", PNAS, vol. 105, No. 27, pp. 9290-9295 (2008).
Arkhipova et al. Diverse DNA transposons in rotifers of the class Bdelloidea. Proc Natl Acad Sci U S A. Aug. 16, 2005;102(33):11781-6.
Mitra et al. PiggyBac can bypass DNA synthesis during cut and paste transposition. EMBO J. Apr. 9, 2008;27(7):1097-109.
Yant et al. Site-directed transposon integration in human cells. Nucleic Acids Res. 2007;35(7):e50.
Yusa et al. A hyperactive piggyBac transposase for mammalian applications. Proc Natl Acad Sci U S A. Jan. 25, 2011;108(4):1531-6.

*Primary Examiner* — Nancy Treptow
(74) *Attorney, Agent, or Firm* — Mintz Levin Cohn Ferris Glovsky and Popeo, P.C.

(57) ABSTRACT

The present invention provides hyperactive piggyBac transposons, in particular hyperactive piggyBac transposons from *Trichoplusia ni* (cabbage looper moth) that transpose at a higher frequency than wildtype. The invention also features integration defective piggyBac transposons. The piggyBac transposons and transposases can be used in gene transfer systems for stably introducing nucleic acids into the DNA of a cell. The gene transfer system can be used in methods, for example, but not limited to, gene therapy, insertional mutagenesis, or gene discovery.

14 Claims, 5 Drawing Sheets

FIG. 1

Table 2

PiggyBac hyperactives - fold increase

| | |
|---|---:|
| wildtype | 1 |
| G2C, Q40R | 8.7 |
| S3N | 23.7 |
| S26P | 12.3 |
| I30V, G165S | 16.4 |
| T43A | 15.9 |
| Q55R | 8.1 |
| T57A | 5.3 |
| S61R | 23.9 |
| I82V | 6.8 |
| I90V | 13.7 |
| S103P | 12.3 |
| S103T | 5.0 |
| N113S | 8.87 |
| M185L | 7.3 |
| M194V | 9.1 |
| S230N | 11.7 |
| R281G | 12.6 |
| M282V | 15.7 |
| G316E | 8.4 |
| P410L | 13.8 |
| I426V | 10.7 |
| Q497L | 8.1 |
| K501N, K565I | 59 |
| N505D, S573L | 10.9 |
| S509G, N570S | 11.1 |
| N538K | 16.4 |
| K575R | 16.9 |
| Q591P | 156 |
| Q591R | 31.8 |
| F594L | 42.2 |

FIG. 2A-1

```
SEQ ID NO: 1
>Trichoplusia ni piggyBac transposon
CCCTAGAAAGATAGTCTGCGTAAAATTGACGCATGCATTCCTTGAAATATTGCTCTCTCTCTTCTAAATAGCGGCGAATCCGTCGCTGTGCGT
TTAGGACATCTCAGTCGCCGCTGGAGCTCCCGTGAGGCGTGCTTGTCAATGCGGTAAGTGCACTGATTTTGAACTATAACGACCGCGT
GAGTCAAAATGACGCATGATTATCTTTACGTGACTGTTTAAGATTTAACTCATACGATAATTATATTGTTATTCATGTTCTACTTACGT
GATAACTTATTATTATATATATTTCTTGTTATAGATATCGTGACTAATATATATAAAATGGGTAGTTCTTTAGACGATGAGCATATCCT
CTCTGCTCTTCTGCAAAGCGATGCAGAGCTTGTTGGTGAGGATTCTGACAGTGAGATCACGTAAGTGAAGATGACGTCCAGAG
CGATACAGAGAAGCGTTTATAGATGAGGTACATGAAGTGCAGCCAACGTCAAGCGGTAGTGAAATATTAGACGAACAAAATGTTATTGA
ACAACCAGGTTCTTCATTGGCTTCTAACAAAATCTTGACCTTGCCACAGAGGACTATTAGAGGTAAGAATAAACATTGTTGGTCAACTTC
AAAGTCCACGAGGCGTAGCCGAGTCTCTGCACTCTCAGATCTCAGATGTCCAGAATTTCGAGATTAATTTCGAGAATTGTAAAATGGACAAATGCTGAGATATCATTGAAACGTCGGGA
ACTTTTATGCTTCAAATCTATTTTTTACTGATGAGATATTTCGGAGAATTGTAAAATGGACAAATGCTGAGATATCATTGAAACGTCGGGA
ATCTATGACAGTGCTACATTCGTGACACGAATGAAGATGAAATCTATGCTTTCTTGGTATTCTGGTAATGACAGCAGTGAGAAAAGA
TAACCACATGTCCACAGATGACCTCTTTGATGCCTTGTCAATGGTGTACGTCTCGTAATGGTCGTGATCGTTTTGATTTTTGAT
ACGATGTCTTAGAATGGATGACAAAAGTATTACACTCCAGGGCCCCACACTTCCCCCAGGCGCCACACTTCGGTTTTAGGACGGTGTCCGTTAG
TATCCATCAGTGCATACAAAATTACACTCCCAGGGCCTATTGGAATAAAATCCTCATGATCGTGTGACAGTGTGTACAAAGTATATGATAAATGGAATGCC
GATGTATATCCCAAAGAGGAACACAGCAAGTAAGTACCAAGCCACTCGGTGAATACGGAGTACCACTCCCTTTGGCAAAAACAGTCGCTCCAATCGGTATCACGTATAAGTAGCTGTGTCG
TAATATTACGTGTGACAATTGGTTCACCTCAGTTGGTCACAATTGGTTCACCTCAGTTAACCATTGTGGAACCGT
GCGATCAAACAACGCGAGATACCGGAAGCCAGTACTGAAAAACAGTCGCTCCAATCGGTATCACGTATAAGTAGCTGTGTCCG
TACTCTCGTCTCATATAAACCGAAGCTAAGATGGTATTAATCAAACTAAGGCGGAGTGGACACATTGCCTGCCATAAGCCCGTCATCGTTTATGCGTTTAGAAGC
TAAACCGCAAATAGGTGGCCTATGCCATTATTGTACGGAATGATAAACATTGCCTGCCATAAGCCCGTCATCGTTTATGCGTTTAGAAGC
CAAGGGAGAAAAGGTTCAAGATATTTGCGCGAGATATCTGCCCCGATAAAATATCTCTGACCTGCAAAATGAAGTGCCTGGTACATCAGATGCCTGGTACTGAAGAGCC
TCCTACTTTGAAGAAATCTGCCTCCATGCGAAATCTTTTCCCAAATGAGGCGAATAAGGCGAAATGCATCGTGCAAAATGCAAAAAGTTAT
AGTAACGAAAAAACGTACTTACTGTACTTACTGCCCCCTCTAAATAAGGCGAATAAGGCGAAATGCATCGTGCAAAATGCAAAAAGTTAT
TGTCGAGAGCATAATATTGATATGTGCCAAAGTTGTTTCTGACTGAGTGTTTCTATTGTTTCATATGTATAAGTTAAGCTAA
TTACTTATTTTATAATACAACACATGATTTGTTTTTTAATTAAAATAAATAAATCATAAATAAATAAATAAGTTTGTTGAATTATTATAGTAAGT
TTATAGAAGAAATTTGAGTTTGTTTTTTTTTTAAAAGTACAAAATAAGTTTATTTTGTAAAGAGAATGTTTTAAAAGTTTTGTTACT
GTAAATATAAATAATAAACTTAATATGTATTCAAATTAATAATAAACCTCGATATACAGACCGATAAAACATGCGTCAATTTTACGCATA
TTATCTTTAACGTACGTCACAATATGATTATCTTTCTAGGG
```

FIG. 2A-2

SEQ ID NO: 2

MGSSLDDEHILSALLQSDDELVGEDSDSEISDHVSEDDVQSDTEEAFIDEVHEVQPTSSGSEILDEQNVIEQPGSSLASNRILTLPQRTI
RGKNKHCWSTSKSTRRSRVSALNIVRSQRGPTRMCRNIYDPLLCFKLFFTDEIISEIVKWTNAEISLKRRESMTGATERDTNEDEIYAFF
GILVMTAVRKDNHMSTDDLFDRSLSMVYVSVMSRDRFDELIRCLRMDDKSIRPTLRENDVFTPVRKIWDLFIHQCIQNYTPGAHLTIDEQ
LLGFRGRCPFRMYIPNKPSKYGIKILMMCDSGTKYMINGMPYLGRGTQTNGVPLIGEYYVKELSKPVHGSCRNITCDNWFTSIPLAKNLLQ
EPYKLTIVGTVRSNKREIPEVLKNSRSRPVGTSMFCFDGPLTLVSYKPKPAKMVYLLSSCDEDASINESTGKPQMVMYYNQTKGGVDTLD
QMCSVMTCSRKTNRWPMALLYGMINIACINSFIIYSHNVSSKGEKVQSRKKFMRNLYMSLTSSFMRKRLEAPTLKRYLRDNISNILPNEV
PGTSDDSTEEPVMKKRTYCTYCPSKIRRKANASCKKCKKVICREHNIDMCQSCF

FIG. 2B

SEQ ID NO: 33
>Trichoplasia ni piggyBac transposase
MGSSLDDEHILSALLQSDDELVGEDSDSEISDHVSEDDVQSDTEEAFIDEVHEVQPTSSGSEILDEQNVIEQPGSSLASNKILTLPQRTI
RGKNKHCWSTSKSTRRSRVSALNHVRSQRGPTRMCRNIYDPLLCFKLFFTDEIISEIVKWTNAEISLKRRESMTGATERDTNEDEIYAFF
GILVMTAVRKDNHMSTDDLFDRSLSMVYVSVMSRDRFDELIRCLRMDDKSIRPTLRENDVFTPVRKIWDLFIHQCIQNYTPGAHLTIDEQ
LLGFRGRCPFRMYIPNKPSKYGIKILMMCDSGTKYMINGMPYLGRGTQTNGVPLIGEYYVKELSKPVHGSCRNITCDNWFTSIPLAKNLLQ
EPYKLTIVGTVRSNKREIPEVLKNSRSRPVGTSMFCFDGPLTLVSYKPKPAKMVYLLSSCDEDASINESTGKPQMVMYYNQTKGGVDTLD
QMCSVMTCSRKTNRWPMALLYGMINIACINSFIIYSHNVSSKGEKVQSRKKFMRNLYMSLTSSFMRKRLEAPTLKRYLRDNISNILPNEV
PGTSDDSTEEPVTKKRTYCTYCPSKIRRKANASCKKKCKKVICREHNIDMCQSCF

FIG. 3

| | | | | |
|---|---|---|---|---|
| -Tps | V436I/S213S | E66G | -Tps | M194V |
| PB int- | Stop to GLESCN | M194V | PB int- | S103P |
| PB | M589V/D170D | M194T | PB | T319A |
| F594L | E45G | L15P | | S31P/T164A |
| F395L | R189K/G120G | L15P | | T560A |
| D19N/S481S | S592G | C97R/T242I | | M589V |
| S573A | H33Y/Q360Q/N571S | E44K/K334R | | F395L |
| Stop to WLESCN | N571S | I221T | | N384T |
| S17G | S373P | | | -Tps |
| S584P | R189W/D450N/R526R | | | |
| | | | PB | PM6+ |

FIG. 4

SEQ ID NO: 64
MGSSLDDEHILSALLQSDDELVGEDSDSEISDHVSEDDVQSDTEEAFIDEVHEVQPTSSGSEILDEQNVIEQPGSSLASNRILTLPQRTI
RGKNKHCWSTSKSTRRSRVSALNIVRSQRGPTRMCRNIYDPLLCFKLFFTDEIISEIVKWTNAEISLKRRESMTGATFRDTNEDEIYAFF
GILVMTAVRKDNHMSTDDLFDRSLSMVYVSVMSRDRFDELIRCLRMDDKSIRPTLRENDVFTPVRKIWDLFHQCIQNYTPGAHLTIDEQ
LLGFRGRCPFRMYIPNKPSKYGIKILMMCDSGTKYMINGMPYLGRGTQTNGVPLGEYYVKELSKPVHGSCRNITCDNWFTSIPLAKNLLQ
EPYKLTIVGTVASNKREIPEVLKNSRSRPVGTSMFCFDGPLTLVSYKPKPAKMVYLLSSCDEDASINESTGKPQMVMYYNQTKGGVDTLD
QMCSVMTCSRKTNRWPMALLYGMINIACINSFIIYSHNVSSKGEKVQSRKKFMRNLYMSLTSSFMRKRLEAPTLKRYLRDNISNILPNEV
PGTSDDSTEEPVMKKRTYCTYCPSKIRRKANASCKKCKKVICREHNIDMCQSCF

SEQ ID NO: 65
MGSSLDDEHILSALLQSDDELVGEDSDSEISDHVSEDDVQSDTEEAFIDEVHEVQPTSSGSEILDEQNVIEQPGSSLASNRILTLPQRTI
RGKNKHCWSTSKSTRRSRVSALNIVRSQRGPTRMCRNIYDPLLCFKLFFTDEIISEIVKWTNAEISLKRRESMTGATFRDTNEDEIYAFF
GILVMTAVRKDNHMSTDDLFDRSLSMVYVSVMSRDRFDELIRCLRMDDKSIRPTLRENDVFTPVRKIWDLFHQCIQNYTPGAHLTIDEQ
LLGFRGRCPFRMYIPNKPSKYGIKILMMCDSGTKYMINGMPYLGRGTQTNGVPLGEYYVKELSKPVHGSCRNITCDNWFTSIPLAKNLLQ
EPYKLTIVGTVASNKREIPEVLKNSRSRPVGTSMFCFDGPLTLVSYKPKPAKMVYLLSSCDEDASINESTGKPQMVMYYNQTKGGVDTLD
QMCSVMTCSRKTNRWPMALLYGMINIACINSFIIYSHNVSSKGEKVQSRKKFMRNLYMSLTSSFMRKRLEAPTLKRYLRDNISNILPNEV
PGTSDDSTEEPVMKKRTYCTYCPSKIRRKANASCKKCKKVICREHNIDMCQSCF

SEQ ID NO: 66
MGSSLDDEHILSALLQSDDELVGEDSDSEISDHVSEDDVQSDTEEAFIDEVHEVQPTSSGSEILDEQNVIEQPGSSLASNRILTLPQRTI
RGKNKHCWSTSKSTRRSRVSALNIVRSQRGPTRMCRNIYDPLLCFKLFFTDEIISEIVKWTNAEISLKRRESMTGATFRDTNEDEIYAFF
GILVMTAVRKDNHMSTDDLFDRSLSMVYVSVMSRDRFDELIRCLRMDDKSIRPTLRENDVFTPVRKIWDLFHQCIQNYTPGAHLTIDEQ
LLGFRGRCPFRMYIPNKPSKYGIKILMMCDSGTKYMINGMPYLGRGTQTNGVPLGEYYVKELSKPVHGSCRNITCDNWFTSIPLAKNLLQ
EPYKLTIVGTVASNKREIPEVLKNSRSRPVGTSMFCFDGPLTLVSYKPKPAKMVYLLSSCDEDASINESTGKPQMVMYYNQTKGGVDTLD
QMCSVMTCSRKTNRWPMALLYGMINIACINSFIIYSHNVSSKGEKVQSRKKFMRNLYMSLTSSFMRKRLEAPTLKRYLRDNISNILPNEV
PGTSDDSTEEPVMKKRTYCTYCPSKIRRKANASCKKCKKVICREHNIDMCQSCF

PIGGYBAC TRANSPOSON VARIANTS AND METHODS OF USE

CROSS-REFERENCE TO RELATED APPLICATION

This application is a continuation application of U.S. Ser. No. 13/203,393, filed Aug. 25, 2011, which is a national stage application filed under 35 U.S.C. §371 of international application no. PCT/US2010/025386, filed Feb. 25, 2010, which claims the benefit of priority under 35 U.S.C. §119(e) to U.S. Provisional Application No. 61/155,207, filed Feb. 25, 2009, each of which is incorporated herein by reference in its entirety.

BACKGROUND OF THE INVENTION

Typical methods for introducing DNA into a cell include DNA condensing reagents such as calcium phosphate, polyethylene glycol, lipid-containing reagents, such as liposomes, multi-lamellar vesicles, as well as virus-mediated strategies. However, such methods can have certain limitations. For example, there are size constraints associated with DNA condensing reagents and virus-mediated strategies. Further, the amount of nucleic acid that can be transfected into a cell is limited in virus strategies. Not all methods facilitate insertion of the delivered nucleic acid into cellular nucleic acid, and while DNA condensing methods and lipid-containing reagents are relatively easy to prepare, the insertion of nucleic acid into viral vectors can be labor intensive. Virus-mediated strategies can be cell-type or tissue-type specific, and the use of virus-mediated strategies can create immunologic problems when used in vivo.

One suitable tool to address these issues are transposons. Transposons, or transposable elements, include a (short) nucleic acid sequence, with terminal repeat sequences upstream and downstream. Active transposons encode enzymes that facilitate the excision and insertion of the nucleic acid into target DNA sequences.

Transposable elements represent a substantial fraction of many eukaryotic genomes. For example, ~50% of the human genome is derived from transposable element sequences, and other genomes, for example plants, may consist of substantially higher proportions of transposable element-derived DNA. Transposable elements are typically divided into two classes, class 1 and class 2. Class 1 is represented by the retrotransposons (LINEs, SINEs, LTRs, and ERVs). Class 2 includes the "cut-and-paste" DNA transposons, which are characterized by terminal inverted repeats (TIRs) and are mobilized by an element-encoded transposase. Currently, 10 superfamilies of cut-and-paste DNA transposons are recognized in eukaryotes (Feschotte and Pritham, 2007).

While class 2 elements are widespread and active in a variety of eukaryotes, they have been thought to be transpositionally inactive in mammalian genomes. This conclusion was based primarily on the initial analyses of the human and mouse genome sequences. While both species harbor a significant number and a diverse assortment of DNA transposons, they show no signs of recent activity (Lander et at. 2001; Waterston et al. 2002). For example, there are more than 300,000 DNA elements recognizable in the human genome, which are grouped into 120 families and belong to five superfamilies. A large subset of these elements (40 families; ~98,000 copies) were integrated in the last 40-80 million years (Myr), but there remains no evidence for any human DNA transposon families younger than ~37 Myr (Pace and Feschotte, 2007).

The natural process of horizontal gene transfer can be mimicked under laboratory conditions. In plants, transposons of the Ac/Ds and Spm families have been routinely transfected into heterologous species (Osborne and Baker, 1995 Curr. Opin. Cell Biol. 7, 406-413). In animals, however, a considerable obstacle to the transfer of an active transposon system from one species to another has been that of species-specificity of transposition due to the requirement for factors produced by the natural host.

Both invertebrate and vertebrate transposons hold potential for transgenesis and insertional mutagenesis in model organisms. Particularly, the availability of alternative transposon systems in the same species opens up new possibilities for genetic analyses.

There still remains a need for new methods for introducing DNA into a cell, and particularly methods that promote the efficient insertion of transposons of varying sizes into the nucleic acid of a cell or the insertion of DNA into the genome of a cell while allowing more efficient transcription/translation results than constructs as available in the state of the art.

SUMMARY OF THE INVENTION

As described in more detail below, the piggyBac transposon from *Trichoplusia ni* (cabbage looper moth) has been shown to be an active element in a number of insects, mice, swine and mammalian cells, including human. The present inventors have isolated *Trichoplusia ni* piggyBac variants that transpose at a higher frequency than wildtype. The hyperactive transposons can be used in gene transfer systems for stably introducing nucleic acids into the DNA of a cell. Moreover, the present inventors have identified integration defective piggyBac transposons. The gene transfer systems of the present invention can be used in methods, for example, but not limited to, gene therapy, insertional mutagenesis, or gene discovery.

Accordingly, in a first aspect, the invention features a transposon comprising one or more hyperactive piggyBac nucleic acid sequences and variants, derivatives and fragments thereof that retain transposon activity.

In one embodiment, the hyperactive piggyBac transposon has a higher level of transposon excision compared to a wildtype piggyBac transposon.

In another embodiment, the transposon comprises 2, 3, 4, 5 or more hyperactive piggyBac nucleic acid sequences and variants, derivatives and fragments thereof that retain transposon activity.

In another further embodiment, the hyperactive piggyBac nucleic acid sequence is from the family Noctuidae. In a further related embodiment, the hyperactive piggyBac nucleic acid sequence is from the species *Trichoplusia ni*.

In another further embodiment, the nucleic acid sequence is selected from SEQ ID NO: 34-SEQ ID NO: 63 or SEQ ID NO: 70 SEQ ID NO: 96.

In a further embodiment, the nucleic acid sequence encodes an amino acid sequence selected from SEQ ID NO: 3-SEQ ID NO: 32.

In another aspect, the present invention features a transposon comprising one or more integration defective piggyBac nucleic acid sequences and variants, derivatives and fragments thereof.

In one embodiment, the integration defective piggyBac transposon has a lower rate of integration as compared to a wildtype piggyBac transposon.

In another embodiment, the integration defective piggyBac nucleic acid sequence is from the family Noctuidae. In a further related embodiment, the integration defective piggyBac nucleic acid sequence is from the species *Trichoplusia ni*.

In one embodiment, the nucleic acid sequence is selected from SEQ ID NO: 67-SEQ ID NO: 69.

In a further embodiment, the nucleic acid sequence encodes an amino acid sequence selected from SEQ ID NO: 64-SEQ ID NO: 66.

In another further embodiment, the wildtype piggyBac transposon comprises a nucleic acid sequence corresponding to SEQ ID NO: 1.

In certain exemplary embodiments, the hyperactive variants comprise an amino acid change in SEQ ID NO: 2 selected from the group consisting of: G2C, Q40R, S3N, S26P, I30V, G165S, T43A, Q55R, T57A, S61R, I82V, I90V, S103P, S103T, N113S, M185L, M194V, 5230N, R281G, M282V, G316E, P410L, I426V, Q497L, K501N, K565I, N505D, S573L, 5509G, N570S, N538K, K575R, Q591P, Q591R, F594L.

In one embodiment of the above aspects, the transposon is capable of inserting into the DNA of a cell.

In another embodiment of the above aspects, the transposon further comprises a marker protein.

In still another embodiment of the above aspects, the transposon is inserted in a plasmid.

In one embodiment, the transposon further comprises at least a portion of an open reading frame. In another embodiment, the transposon further comprises at least one expression control region. In still another further embodiment, the expression control region is selected from the group consisting of a promoter, an enhancer or a silencer. In another related embodiment, the transposon further comprises a promoter operably linked to at least a portion of an open reading frame.

In one embodiment, the cell is obtained from an animal.

In another embodiment, the cell is from a vertebrate or an invertebrate.

In a further embodiment, the vertebrate is a mammal.

In one embodiment, the invention features a gene transfer system comprising a transposon according to any one of the above aspects; and a piggyBac transposase.

In one embodiment, the piggyBac transposase is from the family Noctuidae. In a related embodiment, the piggyBac transposase is from the species *Trichoplusia ni*.

In a further embodiment, the piggyBac transposase comprises an amino acid sequence corresponding to SEQ ID NO: 33.

In another embodiment, the piggyBac transposase is a mammalian piggyBac transposase.

In one embodiment, the transposon is inserted into the genome of the cell.

In another embodiment, the cell is obtained from an animal.

In another embodiment, the cell is from a vertebrate or an invertebrate.

In a further embodiment, the vertebrate is a mammal.

The present invention also features in certain embodiments a cell comprising a transposon of any one of the above-described aspects.

In other aspects, the present invention features a pharmaceutical composition comprising a transposon comprising a hyperactive piggyBac nucleic acid sequence and a piggyBac transposase, together with a pharmaceutically acceptable carrier, adjuvant or vehicle.

The present invention also features a method for introducing exogenous DNA into a cell comprising contacting the cell with the gene transfer system of the above-described aspects, thereby introducing exogenous DNA into a cell.

In one embodiment, the cell is a stem cell.

The present invention also features a kit comprising: a transposon comprising a hyperactive piggyBac nucleic acid sequence and instructions for introducing DNA into a cell.

In one embodiment, the hyperactive piggyBac nucleic acid sequence is from the family Noctuidae. In a further embodiment, the hyperactive piggyBac nucleic acid sequence is from the species *Trichoplusia ni*.

In another embodiment, the nucleic acid is sequence selected from SEQ ID NO: 34-SEQ ID NO: 63 or SEQ ID NO: 70-SEQ ID NO: 96.

In another aspect, the present invention also features a kit comprising: a transposon comprising a integration defective piggyBac nucleic acid sequence and instructions for use.

In one embodiment, the nucleic acid sequence is selected from SEQ ID NO: 67-SEQ ID NO: 69.

Other features and advantages of the invention will be apparent from the detailed description, and from the claims.

DEFINITIONS

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "integration defective" is meant to refer to a transposon that integrates at a lower frequency into the host genome than a corresponding wild type transposon. In certain exemplary embodiments, the inventive transposons integrate by conventional integration mechanisms.

As used herein, the term "nucleotide" or "polynucleotide" is meant to refer to both double- and single-stranded DNA and RNA, and combinations thereof. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, or a fragment. A "coding sequence" or a "coding region" is a polynucleotide that encodes a polypeptide and, when placed under the control of appropriate regulatory sequences, expresses the encoded polypeptide. The boundaries of a coding region are generally determined by a translational start codon at its 5' end and a translational stop codon at its 3' end. A regulatory sequence is a nucleotide sequence that regulates expression of a coding region to which it is operably linked. Non-limiting examples of regulatory sequences include promoters, transcriptional initiation sites, translational start sites, translational stop sites, transcriptional terminators (including, for instance, polyadenylation signals), and intervening sequences (introns).

As used herein, the term "operably linked" is meant to refer a nucleotide sequence that is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary join two protein coding regions, contiguous and in reading frame. Since enhancers may function when separated from the promoter by several kilobases and intron sequences may be of variable lengths, some nucleotide sequences may be operably linked but not contiguous.

As used herein, the term "polypeptide" is meant to refer to a polymer of amino acids of any length. Thus, for example, the terms peptide, oligopeptide, protein, antibody, and enzyme are included within the definition of polypeptide. This term also includes post-expression modifications of the polypeptide, for example, glycosylations (e.g., the addition of a saccharide), acetylations, phosphorylations and the like.

As used herein, the term "transposon" or "transposable element" is meant to refer to a polynucleotide that is able to excise from a donor polynucleotide, for instance, a vector, and integrate into a target site, for instance, a cell's genomic or extrachromosomal DNA. A transposon includes a polynucleotide that includes a nucleic acid sequence flanked by cis-acting nucleotide sequences on the termini of the transposon. A nucleic acid sequence is "flanked by" cis-acting nucleotide sequences if at least one cis-acting nucleotide sequence is positioned 5' to the nucleic acid sequence, and at least one cis-acting nucleotide sequence is positioned 3' to the nucleic acid sequence. Cis-acting nucleotide sequences include at least one inverted repeat (also referred to herein as an inverted terminal repeat, or ITR) at each end of the transposon, to which a transposase, preferably a member of the mammalian piggyBac family of transposases, binds. In certain preferred embodiments, the transposon is from the family Noctuidae. In further preferred embodiments, the transposon is a *Trichoplusia ni* (Cabbage looper moth) piggyBac transposon.

As used herein "*Trichoplusia ni*" is meant to refer to a member of the moth family Noctuidae.

An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

As used herein, the term "transposase" is meant to refer to a polypeptide that catalyzes the excision of a transposon from a donor polynucleotide (e.g., a vector) and the subsequent integration of the transposon into the genomic or extrachromosomal DNA of a target cell. Preferably, the transposase binds an inverted sequence or a direct repeat. The transposase may be present as a polypeptide. Alternatively, the transposase is present as a polynucleotide that includes a coding sequence encoding a transposase. The polynucleotide can be RNA, for instance an mRNA encoding the transposase, or DNA, for instance a coding sequence encoding the transposase. When the transposase is present as a coding sequence encoding the transposase, in some aspects of the invention the coding sequence may be present on the same vector that includes the transposon, i.e., in cis. In other aspects of the invention, the transposase coding sequence may be present on a second vector, i.e., in trans. In certain preferred embodiments, the transposase is a mammalian piggyBac transposase.

BRIEF DESCRIPTION OF THE DRAWINGS

FIG. 1 is a Table (Table 2) that shows the amino acid changes and fold increase in transposition from that of wildtype (normalized to 1) in inventive hyperactive variants.

FIGS. 2A1-2A2 and FIG. 2B show various transposon sequences. FIG. 2A-1 shows the nucleic acid sequence of the wild type *Trichoplusia ni* transposon, corresponding to SEQ ID NO: 1. The corresponding amino acid sequence (SEQ ID NO: 2) is shown in FIG. 2A-2. FIG. 2B shows the amino acid sequence corresponding to the wild type *Trichoplusia ni* transposase, corresponding to SEQ ID NO: 33.

FIG. 3 shows identification of excision hyperactive piggyBac mutants. FIG. 3 discloses "GLESCN" as SEQ ID NO: 130 and "WLESCN" as SEQ ID NO: 128.

FIG. 4 shows the amino acid sequences of the integration defective piggyBac transposons, corresponding to SEQ ID NOs 64-66.

DETAILED DESCRIPTION

The ability to use a transposon for genome engineering is highly dependent upon the frequency with which it can move. For example if 1 progeny in 10 has a transposon event, it will be much easier to isolate derivatives of the desired type than if the transposition event occurs in 1 in 1000 progeny. The present inventors have isolated hyperactive piggyBac transposons from *Trichoplusia ni* (cabbage looper moth) that transpose at a higher frequency than wildtype. Transposons such as piggyBac are widely used for genome engineering by insertional mutagenesis and transgenesis in a wide variety of organisms. The piggyBac transposon from *Trichoplusia ni* has been shown to be an active element in a number of insect, mice, swine and mammalian cells including human.

Accordingly, the present invention features hyperactive piggyBac transposons. A hyperactive piggyBac transposon is meant to refer to a transposon that has a transposon event at a higher frequency than wild type piggyBac transposon. For example, in certain exemplary embodiments, in a hyperactive piggyBac transposon transposition occurs 0.5 fold, 1 fold, 2 fold, 3 fold, 4 fold, 5 fold, 6 fold, 7 fold, 8 fold, 9 fold, 10 fold, 15 fold, 20 fold, 25 fold, 30 fold, 40 fold, 45 fold, 50 fold or more.

According to certain preferred embodiments of the present invention, a hyperactive piggyBac transposon is bound by a transposase, contains a pair of repeat sequences. In certain preferred embodiments, the first repeat is typically located upstream to the nucleic acid sequence and the second repeat is typically located downstream of the nucleic acid sequence. Accordingly, the second repeat represents the same sequence as the first repeat, but shows an opposite reading direction as compared with the first repeat (5' and 3' ends of the complementary double strand sequences are exchanged). These repeats are then termed "inverted repeats" (IRs), due to the fact that both repeats are just inversely repeated sequences. In certain embodiments, repeats may occur in a multiple number upstream and downstream of the above mentioned nucleic acid sequence. Preferably, the number of repeats located upstream and downstream of the above mentioned nucleic acid sequence is identical. In certain embodiments, the repeats are short, between 10-20 base pairs, and preferably 15 base pairs.

The repeats (IRs) as described herein preferably flank a nucleic acid sequence which is inserted into the DNA of a cell. The nucleic acid sequence can include all or part of an open reading frame of a gene (i.e., that part of a protein encoding gene), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame. According to certain preferred embodiments, hyperactive transposons of the present invention can preferably occur as a linear transposons (extending from the 5' end to the 3' end, by convention) that can be used as a linear fragment or circularized, for example in a plasmid.

The present invention features hyperactive piggyBac nucleic acid sequence and variants, derivatives and fragments thereof that retain transposon activity. In preferred embodiments of the invention, the hyperactive piggyBac transposon has a higher level of transposon excision compared to a wildtype piggyBac transposon In certain preferred embodiments, the hyperactive piggyBac transposon nucleic acid sequence is from the family Noctuidae. In further exemplary embodiments, the hyperactive piggyBac transposon nucleic acid sequence is from *Trichoplusia ni*.

Preferred embodiments of the present invention refer to nucleic acids encoding a hyperactive piggyBac transposon as defined herein.

It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides used in the invention to reflect the codon usage of any particular host organism in which the polypeptides are to be expressed. The polynucleotides may be modified by any method available in the art. Such modifications may be carried out in order to enhance the in vivo activity or life span of the polynucleotides of the invention.

Polynucleotides such as DNA polynucleotides may be produced recombinantly, synthetically, or by any means available to those of skill in the art. They may also be cloned by standard techniques.

Longer polynucleotides will generally be produced using recombinant means, for example using PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

It will be appreciated that the polynucleotide of the invention may contain only coding regions. However, it is preferred if the polynucleotide further comprises, in operable linkage, a portion of nucleic acid that allows for efficient translation of the coding sequence. It is further preferred if the polynucleotide (when in a DNA form) further comprises a promoter in operable linkage which allows for the transcription of the coding region and the portion of nucleic acid that allows for efficient translation of the coding region in a target cell.

Nucleic acids according to the present invention typically comprise ribonucleic acids, including mRNA, DNA, cDNA, chromosomal DNA, extrachromosomal DNA, plasmid DNA, viral DNA or RNA. In certain preferred embodiments, a nucleic acid is preferably selected from any nucleic sequence encoding the same amino acid sequence of a hyperactive piggyBac transposon due to degeneration of its genetic code. These alternative nucleic acid sequences may lead to an improved expression of the encoded fusion protein in a selected host organism. Tables for appropriately adjusting a nucleic acid sequence are known to a skilled person. Preparation and purification of such nucleic acids and/or derivatives are usually carried out by standard procedures (see Sambrook et al. 2001, Molecular Cloning: A Laboratory Manual, Cold Spring Harbor, N.Y.). Other variants of these native nucleic acids may have one or more codon(s) inserted, deleted and/or substituted as compared to native nucleic acid sequences. These sequence variants preferably lead to integration defective and/or hyperactive piggyBac transposon proteins having at least one amino acid substituted, deleted and/or inserted as compared to the native nucleic acid sequences of transposons. Therefore, nucleic acid sequences of the present invention may code for modified (non-natural) transposon sequences. Further, promoters or other expression control regions can be operably linked with the nucleic acids encoding the proteins described herein to regulate expression of the protein in a quantitative or in a tissue-specific manner.

In a particular embodiment, the *Tichoplusia ni* wildtype piggyBac transposon comprises a nucleic acid sequence corresponding to SEQ ID NO: 1.

SEQ ID NO: 1
>Trichoplusia ni piggyBac transposon
CCCTAGAAAGATAGTCTGCCTAAAATTGACGCATGCATTCTTGAAATATTGCTCTCTCTTTCTAAATAGCGCGAATCC

GTCACTGTGCGTTTAGGACATCTCAGTCGCCGCTTGGAGCTCCCGTGAGGCGTGCTTGTCAATGCGGTAAGTGTCACT

GATTTTGAACTATAACGACCGCGTGAGTCAAAATGACACATGATTATCTTTTACGTGACTTTTAAGATTTAACTCATA

CGATAATTACATTGTTATTTCATGTTCTACTTACGTGATAACTTATTATATATATTTTCTTGTTATAGATATCGTG

ACTAATATATAATAAAATGGGTAGTTCTTTAGACGATGAGCATATCCTCTCTGCTCTTCTGCAAAGCGATGACGAGCT

TGTTGGTGAGGATTCTGACAGTGAAATATCAGATCACGTAAGTGAAGATGACGTCCAGAGCGATACAGAAGAAGCGTT

TATAGATGAGGTACAGGAAGTGCAGCCAACGTCAAGCGGTAGTGAAATATTAGACGAACAAAATGTTATTGAACAACC

AGGTTCTTCATTGGCTTCTAACAAAATCTTGACCTTGCCACAGAGGACTATTAGAGGTAAGAATAAACATTGTTGGTC

AACTTCAAAGTCCACGAGGCGTAGCCGAGTCTCTGCACTGAATCATGTCAGATCTCAAAGAGGTCCGACGCGTATGTG

CCGCAATATATATGACCCACTTTTATGCTTCAAACTATTTTTTACTGATGAGATAATTTCGGAAATTGTAAAATGGAC

AAATGCTGAGATATCATTGAAACGTCGGGAATCTATGACAGGTGCTACATTTCGTGACACGAATGAAGATGAAATCTA

TGCTTTCTTTAGTATTCTGGTAACGACAGCAGTGAGAAAAGATAACCACATGTCCACAGATGACCTCTTTGATCGATC

TTTGTCAATGGTGTACGTCTCTGTAATGAGTGGTGATCGTTTTGATTTTTTGATACGATGTCTTAGAATGGATGACAA

AAGTATACGGCCCACACTTCGAGAAAACGATGTATTTACTCCTGTTAGAAAAATATGGGATCTCTTTATCCATCAGTG

CATACAAAATTACACTCCAGGGGCTCATTTGACCATAGATGAACAGTTACTTGGTTTTAGAGGACGGTGTGCGTTTAG

GATGTATATGCCAAACAAGGCAAGTAAGTATGGAATAAAAATCGTCATGATGTGTGAGAGTGGTACAAAGTATATGAT

AAATGGAATGCCTTATTAGGGAAGAGGAACACAGACCAACGGAGCACCACTCGGTGAATACTACGTGAAGGAGTTATC

AAAGCCTGTGCACGTAGTTTGTCGCAATATTACGTGTGACAATTGGTTCACCTCAATCCCTTTGGCAAAAAACTTACT

ACAAGAACCGTATAAGTTAACCATTGTGGGAACCGTGCGATCAAACAAACGCGAGATACCGGAAGTACTGAAAAACAG

TCGCTCCAGGCCAGTGGGAACATCGATGTTTTGTTTTGACGGACCCCTTACTCTCGTCTCATATAAACCGAAGCCAGC

TAAGATGGTATACTTATTATCATCTTGTGATGAGGATGCTTCTATCAACGAAAGTACCGGTAAACCGCAAATGGTTAT

GTATTATAATCAAACTAAAGGCGGAGTGGACACGCTAGACCAAATGTGTTCTGTGATGACCTGCAGTAGGAAGACGAA

TAGGTGGCCTATGGCATTATTGTACGGAATGATAAACATTGCCTGCATAAATTCTTTTATTATATACAGCCATAATGT

CAGTAGCAAGGGAGAAAAGGTTCAAAGTCGCAAAAAATTTATGAGAAACCTTTACATGAGCCTGACGTCATCGTTTAT

GCGTAAGCGTTTAGAAGCTCCTACTTTGAAGAGATATTCGCGCGATAATATCTCTAATATTTTGCCAAATGAAGTGCC

TGGTACATCAGATGACAGTACTGAAGAGCCAGTAACGAAAAAACGTACTTACTGTACTTACTGCCCCTCTAAAATAAG

GCGAAAGGCAAAGCATCGTGCAAAAAATGCAAAAAAGTTTATTTGTCGAGAGCATAATATTGATATGTGCCAAAGTTG

TTTCTGACTGACTAATAAGTATAATTTGTTTCTATTATGTATAAGTTAAGCTAATTACTTATTTTATAATACAACATG

AGTGTTTTTAAAGTACAAAATAAGTTTATTTTAGTAAAGGAGAGAATGTTTAAAAGTTTTGTTACTTTATAGAAGAAA

TTTTGAGTTTTTGTTTTTTTTAATAAATAAATAAACATAAATAAATAGTTTGTTGAATTTATTATTAGTATGTAAGT

GTAAATATAATAAAACTTAATATCTATTCAAATTAATAAATAAACCTCGATATACAGACCGATAAAACACATGCGTCA

ATTTTAGGATATTATCTTTAAGGTACGTCACAATATGATTATCTTTCTAGGG

In further embodiments, the *Tichoplusia ni* wildtype piggyBac transposon amino acid sequence corresponds to SEQ ID NO: 2, shown below:

MGSSLDDEHILSALLQSDDELVGEDSDSEISDHVSEDDVQSDTEEAFIDE

VHEVQPTSSGSEILDEQNVIEQPGSSLASNRILTLPQRTIRGKNKHCWST

SKSTRRSRVSALNIVRSQRGPTRMCRNIYDPLLCFKLFFTDEIISEIVKW

TNAEISLKRRESMTGATFRDTNEDEIYAFFGILVMTAVRKDNHMSTDDLF

DRSLSMVYVSVMSRDRFDFLIRCLRMDDKSIRPTLRENDVFTPVRKIWDL

FIHQCIQNYTPGAHLTIDEQLLGFRGRCPFRMYIPNKPSKYGIKILMMCD

SGTKYMINGMPYLGRGTQTNGVPLGEYYVKELSKPVHGSCRNITCDNWFT

SIPLAKNLLQEPYKLTIVGTVRSNKREIPEVLKNSRSRPVGTSMFCFDGP

LTLVSYKPKPAKMVYLLSSCDEDASINESTGKPQMVMYYNQTKGGVDTLD

QMCSVMTCSRKTNRWPMALLYGMINIACINSFIIYSHNVSSKGEKVQSRK

```
KFMRNLYMSLTSSFMRKRLEAPTLKRYLRDNISNILPNEVPGTSDDSTEE

PVMKKRTYCTYCPSKIRRKANASCKKCKKVICREHNIDMCQSCF.
```

As described herein, in certain embodiments, the present invention features integration defective piggyBac transposons. Integration defective is meant to refer to a transposon that integrates at a lower frequency into the host genome than a corresponding wild type transposon. In certain exemplary embodiments, the inventive transposons integrate by conventional integration mechanisms.

Integration defective piggyBac transposons, in certain exemplary embodiments, are derived from the wildtype piggyBac sequence, SEQ ID NO: 2. In exemplary embodiments, the integration defective piggyBac transposon comprises a change in SEQ ID NO: 2 selected from R372A or K375A.

In certain preferred embodiments, the integration defective piggyBac transposon comprises am amino acid sequence selected from SEQ ID NO: 64, SEQ ID NO: 65 or SEQ ID NO: 66.

In certain embodiments, the amino acid change in SEQ ID NO: 2 comprises R372A and corresponds to SEQ ID NO: 64.

```
                                           SEQ ID NO: 64
MGSSLDDEHILSALLQSDDELVGEDSDSEISDHVSEDDVQSDTEEAFIDE

VHEVQPTSSGSEILDEQNVIEQPGSSLASNRILTLPQRTIRGKNKHCWST

SKSTRRSRVSALNIVRSQRGPTRMCRNIYDPLLCFKLFFTDEIISEIVKW

TNAEISLKRRESMTGATFRDTNEDEIYAFFGILVMTAVRKDNHMSTDDLF

DRSLSMVYVSVMSRDRFDFLIRCLRMDDKSIRPTLRENDVFTPVRKIWDL

FIHQCIQNYTPGAHLTIDEQLLGFRGRCPFRMYIPNKPSKYGIKILMMCD

SGTKYMINGMPYLGRGTQTNGVPLGEYYVKELSKPVHGSCRNITCDNWFT

SIPLAKNLLQEPYKLTIVGTVASNKREIPEVLKNSRSRPVGTSMFCFDGP

LTLVSYKPKPAKMVYLLSSCDEDASINESTGKPQMVYYNQTKGGVDTLD

QMCSVMTCSRKTNRWPMALLYGMINIACINSFIIYSHNVSSKGEKVQSRK

KFMRNLYMSLTSSFMRKRLEAPTLKRYLRDNISNILPNEVPGTSDDSTEE

PVMKKRTYCTYCPSKIRRKANASCKKCKKVICREHNIDMCQSCF
```

The integration defective variant encoded by SEQ ID NO: 64 corresponds to a nucleotide change of CGA to GCA in SEQ ID NO: 1, and corresponds to SEQ ID NO: 67.

In other certain embodiments, the amino acid change in SEQ ID NO: 2 comprises K375A and corresponds to SEQ ID NO: 65.

```
                                           SEQ ID NO: 65
MGSSLDDEHILSALLQSDDELVGEDSDSEISDHVSEDDVQSDTEEAFIDE

VHEVQPTSSGSEILDEQNVIEQPGSSLASNRILTLPQRTIRGKNKHCWST

SKSTRRSRVSALNIVRSQRGPTRMCRNIYDPLLCFKLFFTDEIISEIVKW

TNAEISLKRRESMTGATFRDTNEDEIYAFFGILVMTAVRKDNHMSTDDLF

DRSLSMVYVSVMSRDRFDFLIRCLRMDDKSIRPTLRENDVFTPVRKIWDL

FIHQCIQNYTPGAHLTIDEQLLGFRGRCPFRMYIPNKPSKYGIKILMMCD

SGTKYMINGMPYLGRGTQTNGVPLGEYYVKELSKPVHGSCRNITCDNWFT

SIPLAKNLLQEPYKLTIVGTVRSNAREIPEVLKNSRSRPVGTSMFCFDGP

LTLVSYKPKPAKMVYLLSSCDEDASINESTGKPQMVYYNQTKGGVDTLD

QMCSVMTCSRKTNRWPMALLYGMINIACINSFIIYSHNVSSKGEKVQSRK

KFMRNLYMSLTSSFMRKRLEAPTLKRYLRDNISNILPNEVPGTSDDSTEE

PVMKKRTYCTYCPSKIRRKANASCKKCKKVICREHNIDMCQSCF
```

The integration defective variant encoded by SEQ ID NO: 65 corresponds to a nucleotide change of AAA to GCA in SEQ ID NO: 1, and corresponds to SEQ ID NO: 68.

In other certain embodiments, the amino acid change in SEQ ID NO: 2 comprises R372A, K375A and corresponds to SEQ ID NO: 66.

```
                                           SEQ ID NO: 66
MGSSLDDEHILSALLQSDDELVGEDSDSEISDHVSEDDVQSDTEEAFIDE

VHEVQPTSSGSEILDEQNVIEQPGSSLASNRILTLPQRTIRGKNKHCWST

SKSTRRSRVSALNIVRSQRGPTRMCRNIYDPLLCFKLFFTDEIISEIVKW

TNAEISLKRRESMTGATFRDTNEDEIYAFFGILVMTAVRKDNHMSTDDLF

DRSLSMVYVSVMSRDRFDFLIRCLRMDDKSIRPTLRENDVFTPVRKIWDL

FIHQCIQNYTPGAHLTIDEQLLGFRGRCPFRMYIPNKPSKYGIKILMMCD

SGTKYMINGMPYLGRGTQTNGVPLGEYYVKELSKPVHGSCRNITCDNWFT

SIPLAKNLLQEPYKLTIVGTVASNAREIPEVLKNSRSRPVGTSMFCFDGP

LTLVSYKPKPAKMVYLLSSCDEDASINESTGKPQMVYYNQTKGGVDTLD

QMCSVMTCSRKTNRWPMALLYGMINIACINSFIIYSHNVSSKGEKVQSRK

KFMRNLYMSLTSSFMRKRLEAPTLKRYLRDNISNILPNEVPGTSDDSTEE

PVMKKRTYCTYCPSKIRRKANASCKKCKKVICREHNIDMCQSCF
```

The integration defective variant encoded by SEQ ID NO: 66 corresponds to a nucleotide change of CGA to GCA/AAA to GCA in SEQ ID NO: 1, and corresponds to SEQ ID NO: 69.

As described herein, the present invention also features hyperactive piggyBac transposons.

In certain preferred embodiments, the hyperactive piggyBac transposons are generated from the integration defective piggyBac variants. That is, alterations, preferably one or more mutations, are made in the integration defective piggyBac transposon sequence. In other embodiments, the hyperactive piggyBac transposons are generated from the wildtype sequences. That is, alterations, preferably one or more mutations, are made in the wild type piggyBac transposon sequence.

In exemplary embodiments, the hyperactive piggyBac comprises an amino acid sequence selected from the group consisting of: SEQ ID NO: 3-SEQ ID NO: 32.

In other exemplary embodiments, the hyperactive piggyBac comprises a nucleic acid sequence selected from the group consisting of: SEQ ID NO: 34-SEQ ID NO: 63.

The hyperactive piggyBac can preferably comprise one or more nucleic acid sequences selected from the group consisting of: SEQ ID NO: 34-SEQ ID NO: 63. For example, the hyperactive piggyBac can may preferably comprise 1, 2, 3, 4, 5 or more nucleic acid sequences selected from the group consisting of: SEQ ID NO: 34-SEQ ID NO: 63.

In certain exemplary embodiments, the hyperactive variants comprise an amino acid change in SEQ ID NO: 2 selected from the group consisting of: L15P, D19N/F395L, S31P/T164A, H33Y, E44K/K334R, E45G, C97R/T242I, S103P, R189K/G120G, R189R/D450N/R526R, M194T, M194V, S213S/V436I, I221T, S373P, N384T, 453S/N571S, T560A, N571S, S573A, S584P, M589V, M589V/D170D, S592G, F594L, Stop/WLESCN ("WLESCN" disclosed as SEQ ID NO: 128), Stop595ELESCN/H33H ("ELESCN" disclosed as SEQ ID NO: 129).

In certain exemplary embodiments, the hyperactive variants comprise an amino acid change in SEQ ID NO: 64 or 65 selected from the group consisting of: L15P, D19N/F395L, S31P/T164A, H33Y, E44K/K334R, E45G, C97R/T242I, S103P, R189K/G120G, R189R/D450N/R526R, M194T, M194V, S213SN436I, I221T, S373P, N384T, 453S/N571S, T560A, N571S, S573A, S584P, M589V, M589V/D170D, S592G, F594L, Stop/WLESCN ("WLESCN" disclosed as SEQ ID NO: 128), Stop595ELESCN/H33H ("ELESCN" disclosed as SEQ ID NO: 129).

In certain exemplary embodiments, the hyperactive variants comprise an amino acid change in SEQ ID NO: 2 selected from the group consisting of: G2C, Q40R, S3N, S26P, I30V, G165S, T43A, Q55R, T57A, S61R, I82V, I90V, S103P, S103T, N113S, M185L, M194V, S230N, R281G, M282V, G316E, P410L, I426V, Q497L, K501N, K565I, N505D, S573L, 5509G, N570S, N538K, K575R, Q591P, Q591R, F594L.

In certain embodiments, the amino acid change in SEQ ID NOS 64 or 65 comprises L15P and corresponds to SEQ ID NOS 3 & 97. The hyperactive variants encoding SEQ ID NOS 3 & 97 corresponds to a nucleotide change of CUG to CCG in SEQ ID NOS 67 or 68, and corresponds to SEQ ID NOS 34 or 70.

In certain embodiments, the amino acid change in SEQ ID NOS 64 or 65 comprises D19N/F395L and corresponds to SEQ ID NOS 4 & 98. The hyperactive variants encoding SEQ ID NOS 4 & 98 corresponds to a nucleotide change of GAC to AAC/UUU to CUU in SEQ ID NOS 67 or 68, and corresponds to SEQ ID NOS 35 or 71.

In certain embodiments, the amino acid change in SEQ ID NOS 64 or 65 comprises S31P/T164A and corresponds to SEQ ID NOS 5 & 99. The hyperactive variants encoding SEQ ID NOS 5 & 99 corresponds to a nucleotide change of UCA to CCA/ACA to GCA in SEQ ID NOS 67 or 68 and corresponds to SEQ ID NOS 36 or 72.

In certain embodiments, the amino acid change in SEQ ID NOS 64 or 65 comprises H33Y and corresponds to SEQ ID NOS 6 & 100. The hyperactive variants encoding SEQ ID NOS 6 & 100 corresponds to a nucleotide change of CAC to UAC in SEQ ID NOS 67 or 68, and corresponds to SEQ ID NOS 37 or 73.

In certain embodiments, the amino acid change in SEQ ID NOS 64 or 65 comprises E44K/K334R and corresponds to SEQ ID NOS 7 & 101. The hyperactive variants encoding SEQ ID NOS 7 & 101 corresponds to a nucleotide change of GAA to AAA/AAG to AGG in SEQ ID NOS 67 or 68, and corresponds to SEQ ID NOS 38 or 74.

In certain embodiments, the amino acid change in SEQ ID NOS 64 or 65 comprises E45G and corresponds to SEQ ID NOS 8 & 102. The hyperactive variants encoding SEQ ID NOS 8 & 102 corresponds to a nucleotide change of GAA to GGA in SEQ ID NOS 67 or 68, and corresponds to SEQ ID NOS 39 or 75.

In certain embodiments, the amino acid change in SEQ ID NOS 64 or 65 comprises C97R/T242I and corresponds to SEQ ID NOS 9 & 103. The hyperactive variants encoding SEQ ID NOS 9 & 103 corresponds to a nucleotide change of UGU to CGU/ACU to AUU in SEQ ID NOS 67 or 68, and corresponds to SEQ ID NOS 40 or 76.

In certain embodiments, the amino acid change in SEQ ID NOS 64 or 65 comprises S103P and corresponds to SEQ ID NOS 10 & 104. The hyperactive variants encoding SEQ ID NOS 10 & 104 corresponds to a nucleotide change of UCC to CCC in SEQ ID NOS 67 or 68, and corresponds to SEQ ID NOS 41 or 77.

In certain embodiments, the amino acid change in SEQ ID NOS 64 or 65 comprises R189K/G120G and corresponds to SEQ ID NOS 11 & 105. The hyperactive variants encoding SEQ ID NOS 11 & 105 corresponds to a nucleotide change of AGA to AAA/GGU to GGC in SEQ ID NOS 67 or 68, and corresponds to SEQ ID NOS 42 or 78.

In certain embodiments, the amino acid change in SEQ ID NOS 64 or 65 comprises R189R/D450N/R526R and corresponds to SEQ ID NOS 12 & 106. The hyperactive variants encoding SEQ ID NOS 12 & 106 corresponds to a nucleotide change of AGA to AGG/GAC to AAC in SEQ ID NOS 67 or 68, and corresponds to SEQ ID NOS 43 or 79.

In certain embodiments, the amino acid change in SEQ ID NOS 64 or 65 comprises M194T and corresponds to SEQ ID NOS 13 & 107. The hyperactive variants encoding SEQ ID NOS 13 & 107 corresponds to a nucleotide change of AUG to ACG in SEQ ID NOS 67 or 68, and corresponds to SEQ ID NOS 44 or 80.

In certain embodiments, the amino acid change in SEQ ID NOS 64 or 65 comprises M194V and corresponds to SEQ ID NOS 14 & 108. The hyperactive variants encoding SEQ ID NOS 14 & 108 corresponds to a nucleotide change of AUG to GUG in SEQ ID NOS 67 or 68, and corresponds to SEQ ID NOS 45 or 81.

In certain embodiments, the amino acid change in SEQ ID NOS 64 or 65 comprises S213S/V436I and corresponds to SEQ ID NOS 15 & 109. The hyperactive variants encoding SEQ ID NOS 15 & 109 corresponds to a nucleotide change of AGU to AGC in SEQ ID NOS 67 or 68, and corresponds to SEQ ID NOS 46 or 82.

In certain embodiments, the amino acid change in SEQ ID NOS 64 or 65 comprises I221T and corresponds to SEQ ID NOS 16 & 110. The hyperactive variants encoding SEQ ID NOS 16 & 110 corresponds to a nucleotide change of AUA to ACA in SEQ ID NOS 67 or 68, and corresponds to SEQ ID NOS 47 or 83.

In certain embodiments, the amino acid change in SEQ ID NOS 64 or 65 comprises S373P between M6+ and corresponds to SEQ ID NOS 17 & 111. The hyperactive variants encoding SEQ ID NOS 17 & 111 corresponds to a nucleotide change of UCA to CCA in SEQ ID NOS 67 or 68, and corresponds to SEQ ID NOS 48 or 84.

In certain embodiments, the amino acid change in SEQ ID NOS 64 or 65 comprises N384T and corresponds to SEQ ID NOS 18 & 112. The hyperactive variants encoding SEQ ID NOS 18 & 112 corresponds to a nucleotide change of AAC to ACC in SEQ ID NOS 67 or 68, and corresponds to SEQ ID NOS 49 or 85.

In certain embodiments, the amino acid change in SEQ ID NOS 64 or 65 comprises C453S/N571S and corresponds to SEQ ID NOS 19 & 113. The hyperactive variants encoding SEQ ID NOS 19 & 113 corresponds to a nucleotide change of UGU to AGU/AAU to AGU in SEQ ID NOS 67 or 68, and corresponds to SEQ ID NOS 50 or 86.

In certain embodiments, the amino acid change in SEQ ID NOS 64 or 65 comprises T560A and corresponds to SEQ ID NOS 20 & 114. The hyperactive variants encoding SEQ ID NOS 20 & 114 corresponds to a nucleotide change of ACU to GCU in SEQ ID NOS 67 or 68, and corresponds to SEQ ID NOS 51 or 87.

In certain embodiments, the amino acid change in SEQ ID NOS 64 or 65 comprises N571S and corresponds to SEQ ID NOS 21 & 115. The hyperactive variants encoding SEQ ID NOS 21 & 115 corresponds to a nucleotide change of AAU to AAG in SEQ ID NOS 67 or 68, and corresponds to SEQ ID NOS 52 or 88.

In certain embodiments, the amino acid change in SEQ ID NOS 64 or 65 comprises S573A and corresponds to SEQ ID NOS 22 & 116. The hyperactive variants encoding SEQ ID NOS 22 & 116 corresponds to a nucleotide change of UCG to GCG in SEQ ID NOS 67 or 68, and corresponds to SEQ ID NOS 53 or 89.

In certain embodiments, the amino acid change in SEQ ID NOS 64 or 65 comprises S584P and corresponds to SEQ ID NOS 23 & 117. The hyperactive variants encoding SEQ ID NOS 23 & 117 corresponds to a nucleotide change of UCU to CCU in SEQ ID NOS 67 or 68, and corresponds to SEQ ID NOS 54 or 90.

In certain embodiments, the amino acid change in SEQ ID NOS 64 or 65 comprises M589V and corresponds to SEQ ID NOS 24 & 118. The hyperactive variants encoding SEQ ID NOS 24 & 118 corresponds to a nucleotide change of AUG to GUG in SEQ ID NOS 67 or 68, and corresponds to SEQ ID NOS 55 or 91.

In certain embodiments, the amino acid change in SEQ ID NOS 64 or 65 comprises M589V/D170D and corresponds to SEQ ID NOS 25 & 119. The hyperactive variants encoding SEQ ID NOS 25 & 119 corresponds to a nucleotide change of ATG to GUG/GAC to GAU in SEQ ID NOS 67 or 68, and corresponds to SEQ ID NOS 56 or 92.

In certain embodiments, the amino acid change in SEQ ID NOS 64 or 65 comprises S592G and corresponds to SEQ ID NOS 26 & 120. The hyperactive variants encoding SEQ ID NOS 26 & 120 corresponds to a nucleotide change of AGU to GGU in SEQ ID NOS 67 or 68, and corresponds to SEQ ID NOS 57 or 93.

In certain embodiments, the amino acid change in SEQ ID NOS 64 or 65 comprises F594L and corresponds to SEQ ID NOS 27 & 121. The hyperactive variants encoding SEQ ID NOS 27 & 121 corresponds to a nucleotide change of UUC to TTA in SEQ ID NOS 67 or 68, and corresponds to SEQ ID NOS 58 or 94.

In certain embodiments, the amino acid change in SEQ ID NOS 64 or 65 comprises Stop/WLESCN ("WLESCN" disclosed as SEQ ID NO: 128) and corresponds to SEQ ID NOS 28 & 122. The hyperactive variants encoding SEQ ID NOS 28 & 122 corresponds to a nucleotide change of TGA to TGG in SEQ ID NOS 67 or 68, and corresponds to SEQ ID NOS 59 or 95.

In certain embodiments, the amino acid change in SEQ ID NOS 64 or 65 comprises Stop595ELESCN/H33H ("ELESCN" disclosed as SEQ ID NO: 129) and corresponds to SEQ ID NOS 29 & 123. The hyperactive variants encoding SEQ ID NOS 29 & 123 corresponds to a nucleotide change of TGA to GGA/CAC to CAU in SEQ ID NOS 67 or 68, and corresponds to SEQ ID NOS 60 or 96.

In another preferred embodiment the nucleic acid encoding the hyperactive piggyBac transposon is selected from a nucleic acid sequence encoding the hyperactive piggyBac transposon as defined above and being capable of hybridizing to a complement of a nucleic acid sequence as defined above under stringent conditions. In another preferred embodiment the nucleic acid encoding the hyperactive piggyBac transposon is selected from a nucleic acid sequence encoding the hyperactive piggyBac transposase as defined above and being capable of hybridizing to a complement of a nucleic acid sequence as defined above under stringent conditions. Stringent conditions are, for example: 30% (v/v) formamide in 0.5*SSC, 0.1% (w/v) SDS at 42 C for 7 hours.

Assays for measuring the excision of a transposon from a vector, the integration of a transposon into the genomic or extrachromosomal DNA of a cell, and the ability of transposase to bind to an inverted repeat are described herein and are known to the art (see, for instance, (Ivics et al. Cell, 91, 501-510 (1997); WO 98/40510 (Hackett et al.); WO 99/25817 (Hackett et al.), WO 00/68399 (Mclvor et al.), incorporated by reference in their entireties herein. For purposes of determining the frequency of transposition of a transposon of the present invention, the activity of the baseline transposon is normalized to 100%, and the relative activity of the transposon of the present invention determined. Preferably, a transposon of the present invention transposes at a frequency that is, in increasing order of preference, at least about 50%, at least about 100%, at least about 200%, most preferably, at least about 300% greater than a baseline transposon. Preferably, both transposons (i.e., the baseline transposon and the transposon being tested) are flanked by the same nucleotide sequence in the vector containing the transposons.

The invention also features protein sequence showing at least 80%, preferably at least 85%, more preferably at least 90%, even more preferably at least 95% and most preferably at least 98% sequence identity with the protein sequence of any one of SEQ ID NOs 3-32.

The invention also features protein sequence showing at least 80%, preferably at least 85%, more preferably at least 90%, even more preferably at least 95% and most preferably at least 98% sequence identity with the protein sequence of any one of SEQ ID NOs 3-32.

The term "identity" is understood as the degree of identity between two or more proteins, nucleic acids, etc., which may be determined by comparing these sequences using known methods such as computer based sequence alignments (basic local alignment search tool, S. F. Altschul et al., J. Mol. Biol. 215 (1990), 403-410). Such methods include without being limited thereto the GAG programme, including GAP (Devereux, J., et al., Nucleic Acids Research 12 (12): 287 (1984); Genetics Computer Group University of Wisconsin, Madison, (WI)); BLASTP or BLASTN, and FASTA (Altschul, S., et al., J. Mol. Biol. 215:403-410) (1999)). Additionally, the Smith Waterman-algorithm may be used to determine the degree of identity between two sequences.

Functional derivatives according to the present invention preferably maintain the biological function of the mammalian transposase, i.e. the transposase activity, the excision of the nucleic acid sequence and its insertion activity concerning the excised sequences into specific target sequences. Functional derivatives according to the present invention may comprise one or more amino acid insertion(s), deletion(s) and/or substitution(s) of the hyperactive variants as described herein, for example, as those corresponding to SEQ ID NOs 3-32.

Amino acid substitutions as described herein are preferably conservative amino acid substitutions, which do not alter the biological activity of the transposon or transposase protein. Conservative amino acid substitutions are characterized in that an amino acid belonging to a group of amino acids having a particular size or characteristic can be substituted for another amino acid, particularly in regions of the inventive protein that are not associated with catalytic activity or DNA binding activity, for example. Other amino acid sequences may include, for example, amino acid sequences containing conservative changes that do not significantly alter the activity or binding characteristics of the resulting transposase. Substitutions for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Particularly preferred conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$.

Amino acid insertions and substitutions are preferably carried out at those sequence positions of that do not alter the spatial structure or which relate to the catalytic center or binding region of the piggyBac transposon or transposase. A change of a spatial structure by insertion(s) or deletion(s) can be detected readily with the aid of, for example, CD spectra (circular dichroism spectra) (Urry, 1985, Absorption, circular Dichroism and ORD of Polypeptides, in: Modern Physical Methods in Biochemistry, Neuberger et al. (Ed.), Elsevier, Amsterdam). Suitable methods for generating proteins with amino acid sequences which contain substitutions in comparison with the native sequence(s) are disclosed for example in the publications U.S. Pat. No. 4,737,462, U.S. Pat. No. 4,588,585, U.S. Pat. No. 4,959,314, U.S. Pat. No. 5,116,943, U.S. Pat. No. 4,879,111 and U.S. Pat. No. 5,017,691, incorporated by reference in their entireties herein. Other functional derivatives may be additionally stabilized in order to avoid physiological degradation. Such stabilization may be obtained by stabilizing the protein backbone by a substitution of by stabilizing the protein backbone by substitution of the amide-type bond, for example also by employing [beta]-amino acids.

According to certain preferred embodiments of the present invention, the transposon of the present invention may further comprise a marker protein. For example, in certain preferred embodiments, the nucleic acid sequence can be of any variety of recombinant proteins, e.g. any protein known in the art. e.g. the protein encoded by the nucleic acid sequence can be a marker protein such as green fluorescent protein (GFP), the blue fluorescent protein (BFP), the photo activatable-GFP (PA-GFP), the yellow shifted green fluorescent protein (Yellow GFP), the yellow fluorescent protein (YFP), the enhanced yellow fluorescent protein (EYFP), the cyan fluorescent protein (CFP), the enhanced cyan fluorescent protein (ECFP), the monomeric red fluorescent protein (mRFP1), the kindling fluorescent protein (KFP1), aequorin, the autofluorescent proteins (AFPs), or the fluorescent proteins JRed, TurboGFP, PhiYFP and PhiYFP-m, tHc-Red (HcRed-Tandem), PS-CFP2 and KFP-Red (all available commercially available), or other suitable fluorescent proteins chloramphenicol acetyltransferase (CAT). The protein further may be selected from growth hormones, for example to promote growth in a transgenic animal, or from beta-galactosidase (lacZ), luciferase (LUC), and insulin-like growth factors (IGFs), alpha-anti-trypsin, erythropoietin (EPO), factors VIII and XI of the blood clotting system, LDL-receptor, GATA-1, etc. The nucleic acid sequence further may be a suicide gene encoding e.g. apoptotic or apoptose related enzymes and genes including A1F, Apaf e.g. Apaf-1, Apaf-2, Apaf-3, or APO-2 (L), APO-3 (L), Apopain, Bad, Bak, Bax, Bcl-2, Bcl-x.sub.L, Bcl-x.sub.S, bik, CAD, Calpain, Caspases e.g. Caspase-1, Caspase-2, Caspase-3, Caspase-4, Caspase-5, Caspase-6, Caspase-7, Caspase-8, Caspase-9, Caspase-10, Caspase-11, or Granzyme B, ced-3, ced-9, Ceramide, c-Jun, c-Myc, CPP32, crm A, Cytochrome c, D4-GDP-DI, Daxx, CdR1, DcR1, DD, DED, DISC, DNA-PK.sub.CS, DR3, DR4, DR5, FADD/MORT-1, FAK, Fas, Fas-ligand CD95/fas (receptor), FLICE/MACH, FLIP, Fodrin, fos, G-Actin, Gas-2, Gelsolin, glucocorticoid/glucocorticoid receptor, granzyme A/B, hnRNPs C1/C2, ICAD, ICE, JNK, Lamin A/B, MAP, MCL-1, Mdm-2, MEKK-1, MORT-1, NEDD, NF-.sub.kappa.B, NuMa, p53, PAK-2, PARP, Perforin, PITSLRE, PKC.delta., pRb, Presenilin, prICE, RAIDD, Ras, RIP, Sphingomyelinase, SREBPs, thymidine kinase from Herpes simplex, TNF-.alpha., TNF-alpha receptor, TRADD, TRAF2, TRAIL-R1, TRAIL-R2, TRAIL-R3, Transglutaminase, U1 70 kDa snRNP, YAMA, etc.

The inventive piggyBac transposons, preferably in combination with a piggyBac transposase, has several advantages compared to approaches in the prior art, e.g. with respect to viral and retroviral methods. For example, unlike proviral insertions, transposon insertions can be (re)mobilized by supplying the transposase activity in trans. Thus, for example, instead of performing time-consuming microinjections, it is possible according to the present invention to generate transposon insertions at new loci.

The inventive piggyBac transposons, in combination with transposase proteins as defined above can be transfected into a cell as a protein or as ribonucleic acid, including mRNA, as DNA, e.g. as extrachromosomal DNA including, but not limited to, episomal DNA, as plasmid DNA, or as viral nucleic acid. Furthermore, the nucleic acid encoding the transposase protein can be transfected into a cell as a nucleic acid vector such as a plasmid, or as a gene expression vector, including a viral vector. Therefore, the nucleic acid can be circular or linear. A vector, as used herein, refers to a plasmid, a viral vector or a cosmid that can incorporate nucleic acid encoding the transposase protein or the transposon of this invention. The terms "coding sequence" or "open reading frame" refer to a region of nucleic acid that can be transcribed and/or translated into a polypeptide in vivo when placed under the control of the appropriate regulatory sequences.

DNA encoding the transposase protein can be stably inserted into the genome of the cell or into a vector for constitutive or inducible expression. Where the transposase protein is transfected into the cell or inserted into the vector as nucleic acid, the transposase encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product. Exemplary nucleic acid sequences encoding the hyperactive piggyBac transposon are provided as SEQ ID NO: 3-SEQ ID NO: 32 or other hyperactive variants as described herein. In addition to the conservative changes discussed above that would necessarily alter the transposon-encoding nucleic acid sequence (all of which are disclosed herein as well), there are other DNA or RNA sequences encoding the hyperactive piggyBac transposon protein. These DNA or RNA sequences have the same amino acid sequence as a hyperactive piggyBac transposon protein, but take advantage of the degeneracy of the three letter codons used to specify a particular amino acid. For example, it is well known in the art that various specific RNA codons (corresponding DNA codons, with a T substituted for a U) can be used interchangeably to code for specific amino acids.

Methods for manipulating DNA and proteins are known in the art and are explained in detail in the literature such as Sambrook et al, (1989) Molecular Cloning: A Laboratory Manual, Cold Spring Harbor Laboratory Press or Ausubel, R. M., ed. (1994). Current Protocols in Molecular Biology.

Gene Transfer System

The present invention also features a gene transfer system comprising an inventive transposon, an integration defective transposon or a hyperactive piggyBac transposon as described herein, and a piggyBac transposase as described herein.

As mentioned above, the piggyBac transposase protein preferably recognizes repeats (e.g. IRs) on the hyperactive piggyBac transposon. The gene transfer system of this invention, therefore, preferably comprises two components: the transposase as described herein and a hyperactive transposon or integration defective transposon as described herein. Preferably, in certain embodiments, the transposon has at least two repeats (e.g. IRs). When put together these two components provide active transposon activity and allow the transposon to be relocated. In use, the transposase binds to the repeats and promotes insertion of the intervening nucleic acid sequence into DNA of a cell as defined below.

In further exemplary embodiments, the gene transfer system comprises an inventive piggyBac transposon as defined above in combination with a piggyBac transposase protein (or nucleic acid encoding a piggyBac transposase protein to provide its activity in a cell). This combination preferably results in the insertion of the nucleic acid sequence into the DNA of the cell. Alternatively, it is possible to insert the transposon of the present invention into DNA of a cell through non-homologous recombination through a variety of reproducible mechanisms. In either event the inventive transposon can be used for gene transfer by using this gene transfer system.

In certain preferred embodiments, the gene transfer system mediates insertion of the hyperactive piggyBac transposon into the DNA of a variety of cell types and a variety of species by using the piggyBac transposase protein. Preferably, such cells include any cell suitable in the present context, including but not limited to animal cells or cells from bacteria, fungi (e.g., yeast, etc.) or plants. Preferred animal cells can be vertebrate or invertebrate. For example, preferred vertebrate cells include cells from mammals including, but not limited to, rodents, such as rats or mice, ungulates, such as cows or goats, sheep, swine or cells from a human.

In other further exemplary embodiments, such cells, particularly cells derived from a mammals as defined above, can be pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). These cells are advantageously used in order to affirm stable expression of the transposase or to obtain a multiple number of cells already transfected with the components of the inventive gene transfer system. Additionally, cells such as oocytes, eggs, and one or more cells of an embryo may also be considered as targets for stable transfection with the present gene transfer system.

In certain preferred embodiments of the invention, the cells are stem cells.

Cells receiving the inventive piggyBac transposon and/or the piggyBac transposase protein and capable of inserting the transposon into the DNA of that cell also include without being limited thereto, lymphocytes, hepatocytes, neural cells, muscle cells, a variety of blood cells, and a variety of cells of an organism, embryonic stem cells, somatic stem cells e.g. hematopoietic cells, embryos, zygotes, sperm cells (some of which are open to be manipulated by an in vitro setting).

In other certain exemplary embodiments, the cell DNA that acts as a recipient of the transposon of described herein includes any DNA present in a cell (as mentioned above) to be transfected, if the inventive piggyBac transposon, e.g. the hyperactive piggyBac transposon, is in contact with an piggyBac transposase protein within the cell. For example, the DNA can be part of the cell genome or it can be extrachromosomal, such as an episome, a plasmid, a circular or linear DNA fragment. Typical targets for insertion are e.g. double-stranded DNA.

The components of the gene transfer system described herein, i.e. the piggyBac transposase protein (either as a protein or encoded by a nucleic acid as described herein) and an inventive piggyBac transposon can be transfected into a cell, preferably into a cell as defined above, and more preferably into the same cell. Transfection of these components may furthermore occur in subsequent order or in parallel. E.g. the piggyBac transposase protein or its encoding nucleic acid may be transfected into a cell as defined above prior to, simultaneously with or subsequent to transfection of the mammalian piggyBac transposon. Alternatively, the transposon may be transfected into a cell as defined above prior to, simultaneously with or subsequent to transfection of the piggyBac transposase protein or its encoding nucleic acid. If transfected parallel, preferably both components are provided in a separated formulation and/or mixed with each other directly prior to administration in order to avoid transposition prior to transfection. Additionally, administration of at least one component of the gene transfer system may occur repeatedly, e.g. by administering at least one, two or multiple doses of this component.

For any of the above transfection reactions, the gene transfer system may be formulated in a suitable manner as known in the art, or as a pharmaceutical composition or kit as described herein.

In further preferred embodiments, the components of the gene transfer system may preferably be transfected into one or more cells by techniques such as particle bombardment, electroporation, microinjection, combining the components with lipid-containing vesicles, such as cationic lipid vesicles, DNA condensing reagents (e.g., calcium phosphate, polylysine or polyethyleneimine), and inserting the components (i.e. the nucleic acids thereof into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

As already mentioned above the nucleic acid encoding the piggyBac transposase protein may be RNA or DNA. Similarly, either the nucleic acid encoding the piggyBac transposase protein or the transposon of this invention can be transfected into the cell as a linear fragment or as a circularized fragment, preferably as a plasmid or as recombinant viral DNA.

Furthermore, the nucleic acid encoding the piggyBac transposase protein is thereby preferably stably or transiently inserted into the genome of the cell to facilitate temporary or prolonged expression of the piggyBac transposase protein in the cell.

The gene transfer system as disclosed above represents a considerable refinement of non-viral DNA-mediated gene transfer. For example, adapting viruses as agents for gene therapy restricts genetic design to the constraints of that virus genome in terms of size, structure and regulation of expression. Non-viral vectors, as described herein, are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors. Additionally, the inventive gene transfer system is a non-viral gene transfer system that facilitates insertion into DNA and markedly improves the frequency of stable gene transfer.

The present invention further provides an efficient method for producing transgenic animals, including the step of applying the inventive gene transfer system to an animal. Transgenic DNA has not been efficiently inserted into chromosomes. Only about one in a million of the foreign DNA molecules is inserted into the cellular genome, generally several cleavage cycles into development. Consequently, most transgenic animals are mosaic (Hackett et al. (1993). The molecular biology of transgenic fish. In Biochemistry and Molecular Biology of Fishes (Hochachka & Mommsen, eds) Vol. 2, pp. 207-240). As a result, animals raised from embryos into which transgenic DNA has been delivered must be cultured until gametes can be assayed for the presence of inserted foreign DNA. Many transgenic animals fail to express the transgene due to position effects. A simple, reliable procedure that directs early insertion of exogenous DNA into the chromosomes of animals at the one-cell stage is needed. The present system helps to fill this need.

In certain preferred embodiments, the gene transfer system of this invention can readily be used to produce transgenic animals that carry a particular marker or express a particular protein in one or more cells of the animal. Generally, methods for producing transgenic animals are known in the art and incorporation of the inventive gene transfer system into these techniques does not require undue experimentation, e.g. there are a variety of methods for producing transgenic animals for research or for protein production including, but not limited to Hackett et al. (1993, supra). Other methods for producing transgenic animals are described in the art (e.g. M. Markkula et al. Rev. Reprod., 1, 97-106 (1996); R. T. Wall et al., J. Dairy Sci., 80, 2213-2224 (1997)), J. C. Dalton, et al. (Adv. Exp. Med. Biol., 411, 419-428 (1997)) and H. Lubon et al. (Transfus. Med. Rev., 10, 131-143 (1996)).

In another embodiment, the present invention features a transgenic animal produced by the methods described herein, preferably by using the gene transfer system presently described. For example, transgenic animals may preferably contain a nucleic acid sequence inserted into the genome of the animal by the gene transfer system, thereby enabling the transgenic animal to produce its gene product, e.g. a protein. In transgenic animals this protein is preferably a product for isolation from a cell, for example the inventive protein can be produced in quantity in milk, urine, blood or eggs. Promoters can be used that promote expression in milk, urine, blood or eggs and these promoters include, but are not limited to, casein promoter, the mouse urinary protein promoter, beta-globin promoter and the ovalbumin promoter respectively. Recombinant growth hormone, recombinant insulin, and a variety of other recombinant proteins have been produced using other methods for producing protein in a cell. Nucleic acids encoding these or other proteins can be inserted into the transposon of this invention and transfected into a cell. Efficient transfection of the inventive transposon as defined above into the DNA of a cell occurs when mammalian piggyBac transposase protein is present. Where the cell is part of a tissue or part of a transgenic animal, large amounts of recombinant protein can be obtained.

Transgenic animals may be selected from vertebrates and invertebrates, e.g. fish, birds, mammals including, but not limited to, rodents, such as rats or mice, ungulates, such as cows or goats, sheep, swine or humans.

The present invention furthermore provides a method for gene therapy comprising the step of introducing the gene transfer system into cells as described herein. Therefore, the inventive piggyBac transposons as described herein preferably comprises a gene to provide a gene therapy to a cell or an organism. Preferably, the gene is placed under the control of a tissue specific promoter or of a ubiquitous promoter or one or more other expression control regions for the expression of a gene in a cell in need of that gene. Presently, a variety of genes are being tested for a variety of gene therapies including, but not limited to, the CFTR gene for cystic fibrosis, adenosine deaminase (ADA) for immune system disorders, factor IX and interleukin-2 (IL-2) for blood cell diseases, alpha-1-antitrypsin for lung disease, and tumor necrosis factors (INFs) and multiple drug resistance (MDR) proteins for cancer therapies. These and a variety of human or animal specific gene sequences including gene sequences to encode marker proteins and a variety of recombinant proteins are available in the known gene databases such as GenBank.

An advantage of the inventive gene transfer system for gene therapy purposes is that it is not limited to a great extent by the size of the intervening nucleic acid sequence positioned between the repeats. There is no known limit on the size of the nucleic acid sequence that can be inserted into DNA of a cell using the mammalian piggyBac transposase protein.

In particular preferred embodiments, for gene therapy purposes, but also for other inventive purposes the gene transfer system may be transfected into cells by a variety of methods, e.g. by microinjection, lipid-mediated strategies or by viral-mediated strategies. For example, where microinjection is used, there is very little restraint on the size of the intervening sequence of the transposon of this invention. Similarly, lipid-mediated strategies do not have substantial size limitations. However, other strategies for introducing the gene transfer system into a cell, such as viral-mediated strategies could limit the length of the nucleic acid sequence positioned between the repeats.

Accordingly, in certain exemplary embodiments, the gene transfer system as described herein can be delivered to cells via viruses, including retroviruses (such as lentiviruses, etc.), adenoviruses, adeno-associated viruses, herpes viruses, and others. There are several potential combinations of delivery mechanisms that are possible for the hyperactive piggyBac transposon portion containing the transgene of interest flanked by the terminal repeats and the gene encoding the transposase. For example, both the transposon and the transposase gene can be contained together on the same recombinant viral genome; a single infection delivers both parts of the gene transfer system such that expression of the transposase then directs cleavage of the transposon from the recombinant viral genome for subsequent insertion into a cellular chromosome. In another example, the transposase and the transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for insertion into chromosomal DNA.

In certain preferred embodiments of the present invention, inventive piggyBac transposons may be utilized for insertional mutagenesis, preferably followed by identification of the mutated gene. DNA transposons, particularly the transposons, have several advantages compared to approaches in the prior art, e.g. with respect to viral and retroviral methods. For example, unlike proviral insertions, transposon insertions can be remobilized by supplying the transposase activity in trans. Thus, instead of performing time-consuming microinjections, it is possible according to the present invention to generate transposon insertions at new loci by crossing stocks transgenic for the above mentioned two components of the transposon system, the inventive transposon and the inventive transposase. In a preferred embodiment the gene transfer system is directed to the germline of the experimental animals in order to mutagenize germ cells. Alternatively, transposase expression can be directed to particular tissues or organs by using a variety of specific promoters. In addition, remobilization of a mutagenic transposon out of its insertion site can be used to isolate revertants and, if transposon excision is associated with a deletion of flanking DNA, the inventive gene transfer system may be used to generate deletion mutations. Furthermore, since transposons are composed of DNA, and can be maintained in simple plasmids, inventive transposons and particularly the use of the inventive gene transfer system is much safer and easier to work with than highly infectious retroviruses. The transposase activity can be supplied in the form of DNA, mRNA or protein as defined above in the desired experimental phase.

In another embodiment, the present invention also provides an efficient system for gene discovery, e.g. genome mapping, by introducing an inventive piggyBac transposon, as defined above into a gene using a gene transfer system as described in the present invention. In one example, the hyperactive piggyBac transposon in combination with the piggyBac transposase protein or a nucleic acid encoding the piggyBac transposase protein is transfected into a cell. In certain preferred embodiments, the transposon preferably comprises a nucleic acid sequence positioned between at least two repeats, wherein the repeats bind to the piggyBac transposase protein and wherein the transposon is inserted into the DNA of the cell in the presence of the piggyBac transposase protein. In certain preferred embodiments, the nucleic acid sequence includes a marker protein, such as GFP and a restriction endonuclease recognition site. Following insertion, the cell DNA is isolated and digested with the restriction endonuclease. For example, if the endonuclease recognition site is a 6-base recognition site and a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the repeats in the transposon. The amplified fragments are then sequenced and the DNA flanking the direct repeats is used to search computer databases such as GenBank.

Using the gene transfer system for methods as disclosed above such as gene discovery and/or gene tagging, permits, for example, identification, isolation, and characterization of genes involved with growth and development through the use of transposons as insertional mutagens or identification, isolation and characterization of transcriptional regulatory sequences controlling growth and development.

In another exemplary embodiment of the present invention, the invention provides a method for mobilizing a nucleic acid sequence in a cell. According to this method the hyperactive piggyBac transposon is inserted into DNA of a cell, as described herein. Hyperactive piggyBac protein or nucleic acid encoding the piggyBac transposase protein is transfected into the cell and the protein is able to mobilize (i.e. move) the transposon from a first position within the DNA of the cell to a second position within the DNA of the cell. The DNA of the cell is preferably genomic DNA or extrachromosomal DNA. The inventive method allows movement of the transposon from one location in the genome to another location in the genome, or for example, from a plasmid in a cell to the genome of that cell.

In another exemplary embodiments, the inventive gene transfer system can also be used as part of a method involving RNA-interference techniques. RNA interference (RNAi), is a technique in which exogenous, double-stranded RNAs (dsRNAs), being complementary to mRNA's or genes/gene fragments of the cell, are introduced into this cell to specifically bind to a particular mRNA and/or a gene and thereby diminishing or abolishing gene expression. The technique has proven effective in *Drosophila, Caenorhabditis elegans*, plants, and recently, in mammalian cell cultures. In order to apply this technique in context with the present invention, the inventive transposon preferably contains short hairpin expression cassettes encoding small interfering RNAs (siRNAs), which are complementary to mRNA's and/or genes/gene fragments of the cell. These siRNAs have preferably a length of 20 to 30 nucleic acids, more preferably a length of 20 to 25 nucleic acids and most preferably a length of 21 to 23 nucleic acids. The siRNA may be directed to any mRNA and/or a gene, that encodes any protein as defined above, e.g. an oncogene. This use, particularly the use of mammalian piggyBac transposons for integration of siRNA vectors into the host genome provides a long-term expression of siRNA in vitro or in vivo and thus enables a long-term silencing of specific gene products.

Induced Pluripotent Stem Cells (iPS)

In certain preferred embodiments, the present invention may include a reprogramming vector that includes a polycistronic expression cassette comprising a transcriptional regulatory element, one or more reprogramming factors, and one or more hyperactive piggyBac transposons as described herein. Preferably, the reprogramming factor encoded is Sox, Oct, Nanog, Klf4, or c-Myc In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

Induced pluripotent stem cells, commonly abbreviated as iPS cells or iPSCs, are a type of pluripotent stem cells artificially derived from non-pluripotent cells, typically adult somatic cells, by inserting certain genes. Induced pluripotent stem cells are believed to be identical to natural pluripotent stem cells, such as embryonic stem cells in many respects, for example, in the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

iPS cells were first produced in 2006 (Takahashi et al., 2006, incorporated by reference in its entirety herein) from mouse cells and in 2007 from human cells (Takahashi et al., 2007, incorporated by reference in its entirety herein). This has been cited as an important advancement in stem cell research, as it may allow researchers to obtain pluripotent stem cells, which are important in research and potentially have therapeutic uses, without the controversial use of embryos.

"Reprogramming" is a process that confers on a cell a measurably increased capacity to form progeny of at least one new cell type, either in culture or in vivo, than it would have under the same conditions without reprogramming More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming Under certain conditions, the proportion of progeny with characteristics of the new cell type may be at least about 1%, 5%, 25% or more in the in order of increasing preference.

Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

The generation of iPS cells is crucial on the genes used for the induction. The following factors or combination thereof could be used in the present invention. In certain aspects, nucleic acids encoding Sox and Oct (preferably Oct3/4) will be included into the reprogramming vector. For example, a reprogramming vector may comprise expression cassettes encoding Sox2, Oct4, Nanog and optionally Lin-28, or expression cassettes encoding Sox2, Oct4, Klf4 and optionally c-myc. Nucleic acids encoding these reprogramming factors may be comprised in the same expression cassette, different expression cassettes, the same reprogramming vector, or different reprogramming vectors.

Oct-3/4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (C-myc, L-myc, and N-myc), Nanog, and LIN28, have been identified to increase the induction efficiency. Oct-3/4 (Pou5f1) is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction, thus demonstrating the exclusiveness of Oct-3/4 to the induction process.

The Sox family of genes is associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction by Yamanaka et al. (2007), Jaenisch et al. (1988) and Yu et al. (2007), other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, at least an Oct member such as Oct-3/4 and at least a Sox member such as Sox2, are necessary in promoting pluripotency. Yamanaka et al. (2007) reported that Nanog was unnecessary for induction although Yu et al. (2007) has reported it is possible to generate iPS cells with Nanog as one of the factors and Nanog certainly enhances reprogramming efficiency dose-dependently.

Klf4 of the Klf family of genes was initially identified by Yamanaka et al. and confirmed by Jaenisch et al. (1988) as a factor for the generation of mouse iPS cells and was demonstrated by Yamanaka et al. (2007) as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. (1988) demonstrated that c-myc is a factor implicated in the generation of mouse iPS cells and Yamanaka et al. demonstrated it was a factor implicated in the generation of human iPS cells. However, Thomson et al. and Yamanaka et al. (2007) reported that c-myc was unnecessary for generation of human iPS cells. Usage of the "myc" family of genes in induction of iPS cells is troubling for the eventuality of iPS cells as clinical therapies, as 25% of mice transplanted with c-myc-induced iPS cells developed lethal teratomas. N-myc and L-myc have been identified to induce in the stead of c-myc with similar efficiency.

Pharmaceutical Compositions

The present invention further refers to pharmaceutical compositions containing either a piggyBac transposase as a protein or encoded by a nucleic acid, and/or a hyperactive piggyBac transposon, or a gene transfer system as described herein comprising a piggyBac transposase as a protein or encoded by a nucleic acid, in combination with a hyperactive piggyBac transposon.

The pharmaceutical composition may optionally be provided together with a pharmaceutically acceptable carrier, adjuvant or vehicle. In this context, a pharmaceutically acceptable carrier, adjuvant, or vehicle according to the invention refers to a non-toxic carrier, adjuvant or vehicle that does not destroy the pharmacological activity of the component(s) with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally or via an implanted reservoir.

The term parenteral as used herein includes subcutaneous, intravenous, intramuscular, intra-articular, intra-synovial, intrasternal, intrathecal, intrahepatic, intralesional and intracranial injection or infusion techniques. Preferably, the pharmaceutical compositions are administered orally, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the inventive gene transfer system or components thereof with a suitable non-irritating excipient that is solid at room temperature but liquid at rectal temperature and Therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

For topical applications, the pharmaceutically acceptable compositions may be formulated in a suitable ointment containing the inventive gene transfer system or components thereof suspended or dissolved in one or more carriers. Carriers for topical administration of the components of this invention include, but are not limited to, mineral oil, liquid petrolatum, white petrolatum, propylene glycol, polyoxyethylene, polyoxypropylene component, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the components of the present invention that may be combined with the carrier materials to produce a composition in a single dosage form will vary depending upon the host treated, the particular mode of administration. It has to be noted that a specific dosage and treatment regimen for any particular patient will depend upon a variety of factors, including the activity of the specific component employed, the age, body weight, general health, sex, diet, time of administration, rate of excretion, drug combination, and the judgment of the treating physician and the severity of the particular disease being treated. The amount of a component of the present invention in the composition will also depend upon the particular component(s) in the composition.

The pharmaceutical composition is preferably suitable for the treatment of diseases, particular diseases caused by gene defects such as cystic fibrosis, hypercholesterolemia, hemophilia, immune deficiencies including HIV, Huntington disease, .alpha.-anti-Trypsin deficiency, as well as cancer selected from colon cancer, melanomas, kidney cancer, lymphoma, acute myeloid leukemia (AML), acute lymphoid leukemia (ALL), chronic myeloid leukemia (CML), chronic lymphocytic leukemia (CLL), gastrointestinal tumors, lung cancer, gliomas, thyroid cancer, mamma carcinomas, prostate tumors, hepatomas, diverse virus-induced tumors such as e.g. papilloma virus induced carcinomas (e.g. cervix carcinoma), adeno carcinomas, herpes virus induced tumors (e.g. Burkitt's lymphoma, EBV induced B cell lymphoma), Hepatitis B induced tumors (Hepato cell carcinomas), HTLV-1 and HTLV-2 induced lymphoma, lung cancer, pharyngeal cancer, anal carcinoma, glioblastoma, lymphoma, rectum carcinoma, astrocytoma, brain tumors, stomach cancer, retinoblastoma, basalioma, brain metastases, medullo blastoma, vaginal cancer, pancreatic cancer, testis cancer, melanoma, bladder cancer, Hodgkin syndrome, meningeoma, Schneeberger's disease, bronchial carcinoma, pituitary cancer, mycosis fungoides, gullet cancer, breast cancer, neurinoma, spinalioma, Burkitt's lymphoma, laryngeal cancer, thymoma, corpus carcinoma, bone cancer, non-Hodgkin lymphoma, urethra cancer, CUP-syndrome, oligodendroglioma, vulva cancer, intestinal cancer, oesphagus carcinoma, small intestine tumors, craniopharyngeoma, ovarial carcinoma, ovarian cancer, liver cancer, leukemia, or cancers of the skin or the eye; etc.

Kits

The present invention also features kits comprising a piggyBac transposase as a protein or encoded by a nucleic acid, and/or a hyperactive piggyBac transposon; or a gene transfer system as described herein comprising a piggyBac transposase as a protein or encoded by a nucleic acid as described herein, in combination with a hyperactive piggyBac transposon; optionally together with a pharmaceutically acceptable carrier, adjuvant or vehicle, and optionally with instructions for use.

Any of the components of the inventive kit may be administered and/or transfected into cells in a subsequent order or in parallel. e.g. the piggyBac transposase protein or its encoding nucleic acid may be administered and/or transfected into a cell as defined above prior to, simultaneously with or subsequent to administration and/or transfection of the inventive hyperactive transposon. Alternatively, the hyperactive piggyBac transposon may be transfected into a cell as defined above prior to, simultaneously with or subsequent to transfection of the piggyBac transposase protein or its encoding nucleic acid. If transfected parallel, preferably both components are provided in a separated formulation and/or mixed with each other directly prior to administration in order to avoid transposition prior to transfection. Additionally, administration and/or transfection of at least one component of the kit may occur in a time staggered mode, e.g. by administering multiple doses of this component.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Identification of Integration-Defective piggyBac Variants

The present experiments describe screening and identification of excision-hyperactive piggyBac transposons using a version of the Cherry gene which produces a red fluorescent protein. A copy of the piggyBac transposon was put into the gene, inactivating it such as the cells are NOT red. However, piggyBac excision restores the gene, leading to the production of the red fluorescent protein. Accordingly, increased red colony color identifies mutants that excise better.

A large collection of mutant transposase genes was made using mutagenic PCR which was cloned into an expression vector in yeast. Colonies containing individual mutants were grow up on an agar plate and were then examined with red fluorescent light. FIG. 4 shows excision hyperactives that have been isolated to date.

In certain preferred embodiments, the integration defective piggyBac comprises an amino acid change in the wild type piggyBac sequence corresponding to SEQ ID NO: 2. Preferably, the amino acid change is R371A, R373A or R371A, R373A.

In preferred exemplary embodiments, the integration defective piggyBac corresponds to the amino acid sequence set forth as SEQ ID NO: 64, SEQ ID NO: 65 or SEQ ID NO: 66.

Example 2

Identification of Hyperactive Variants

Using the integration defective piggyBac mutants as a starting point, the present inventors have identified hyperactive piggyBac transposon mutants. The yeast excision assay that was developed as described in Mitra R. et al. (piggyBac can bypass DNA synthesis during cut and paste transposition. EMBO J. April 9; 27(7):1097-109. Epub 2008 Mar. 20) was used to identify the hyperactive mutants. The piggyBac ORF was mutagenized by mutagenic PCR using primers flanking the ORF as the expression construct and then recovered transformants by co-transformation of the PCR product with a gapped piggyBac plasmid into the yeast assay strain containing a ura− to ura+ cassesette in which transposon excision results in formation of ura+ colonies. Following recovery of transformants on SC-Trp-His plates, colonies were resuspended in water and spotted onto plates lacking uracil to identify excisions. By comparison to the number of ura+ colonies from the mutagenized transformants to wildtype in these spotting tests, potential hyperactive variants were identified. Each hyperactive candidate strain was then purified and quantitatively reassayed excision. Plasmid DNA containing the piggyBac gene from confirmed hyperactives was then sequenced to identify the piggyBac gene mutation and resulting amino acid change Amino acid changes and corresponding nucleic acid changes are shown in Table 1, below:

TABLE 1

| | |
|---|---|
| L15P | CUG to CCG |
| D19N/F395L | GAC to AAC/UUU to CUU |
| S31P/T164A | UCA to CCA/ACA to GCA |
| H33Y | CAC to UAC |
| E44K/K334R | GAA to AAA/AAG to AGG |
| E45G | GAA to GGA |
| C97R/T242I | UGU to CGU/ACU to AUU |
| S103P | UCC to CCC |
| R189K/G120G | AGA to AAA/GGU to GGC |
| R189R/D450N/R526R | AGA to AGG/GAC to AAC |
| M194T | AUG to ACG |
| M194V | AUG to GUG |
| S213S/V436I | AGU to AGC |
| I221T | AUA to ACA |
| S373P between M6+ | UCA to CCA |
| N384T | AAC to ACC |
| C453S/N571S | UGU to AGU/AAU to AGU |
| T560A | ACU to GCU |
| N571S | AAU to AAG |
| S573A | UCG to GCG |
| S584P | UCU to CCU |
| M589V | AUG to GUG |
| M589V/D170D | ATG to GUG/GAC to GAU |
| S592G | AGU to GGU |

TABLE 1-continued

| | |
|---|---|
| F594L | UUC to TTA |
| Stop/WLESCN | TGA to TGG |
| Stop595ELESCN/H33H | TGA to GGA/CAC to CAU |

Table 1 discloses "WLESCN" as SEQ ID NO: 128 and "ELESCN" as SEQ ID NO: 129.

The amino acid changes and fold increase in transposition from that of wildtype (normalized to 1) for certain exemplary hyperactive mutants is shown in Table 2 in FIG. 1.

Hyperactive mutations can occur at many positions within the transposase and it is expected that many more hyperactive piggyBac variants will be found. These variants may be altered in a single amino acid or multiple amino acids. Variants can be identified using the yeast assay as a screen. PCR mutagenesis of the entire gene as well as targeted mutagenesis using smaller piggyBac fragments or oligonucleotide-directed mutagenesis to regions that have been identified as giving hyperactive mutations will be used.

Example 3

Induced Pluripotent Stem Cell Generation Using the Hyperactive Transposon

In certain exemplary embodiments, the hyperactive piggyBac transposons can be used to created induced pluripotent stem cells using a minimal set of genes. In particular, Oct ¾, Sox2, Klf4 and c-myc are used as a minimal set of genes. Takahashi et al. (Cell, 131, 861-872, Nov. 30, 2007), incorporated by reference in its entirety herein, teach methods of generating induced pluripotent stem cells (iPS) from human dermal fibroblasts using Oct 3/4, Sox2, klf4, and c-Myc.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A transposon comprising a synthetic Noctuidae *Trichoplusia ni* piggyBac nucleic acid sequence, wherein said piggyBac nucleic acid sequence exhibits hyperactive piggyBac transposition activity, a higher level of piggyBac transposon excision, and a lower level of piggyBac transposon integration compared to a wildtype Noctuidae *Trichoplusia ni* piggyBac transposon, wherein said synthetic piggyBac nucleic acid sequence encodes a hyperactive variant of an amino acid sequence consisting of SEQ ID NO: 64, wherein a methionine at amino acid position 194 of SEQ ID NO: 64 is replaced with a valine (SEQ ID NO: 14); or wherein said synthetic piggyBac nucleic acid sequence encodes a hyperactive variant of an amino acid sequence consisting of SEQ ID NO: 65, wherein a methionine at amino acid position 194 of SEQ ID NO: 65 is replaced with a valine (SEQ ID NO: 108); or wherein said synthetic piggyBac nucleic acid sequence encodes a hyperactive variant of an amino acid sequence consisting of SEQ ID NO: 66, wherein a methionine at amino acid position 194 of SEQ ID NO: 66 is replaced with a valine.

2. A transposon comprising a synthetic Noctuidae *Trichoplusia ni* piggyBac nucleic acid sequence, wherein said piggyBac nucleic acid sequence exhibits hyperactive piggyBac transposition activity, a higher level of piggyBac transposon excision, and a lower level of piggyBac transposon integration compared to a wildtype Noctuidae *Trichoplusia ni* piggyBac transposon, wherein said synthetic piggyBac nucleic acid sequence encodes a hyperactive variant of an amino acid sequence consisting of SEQ ID NO: 64, wherein a methionine at amino acid position 194 of SEQ ID NO: 64 is replaced with a valine (SEQ ID NO: 14), and wherein an isoleucine at amino acid position 30 of SEQ ID NO: 64 is replaced with a valine, a serine at amino acid position 103 of SEQ ID NO: 64 is replaced with a proline, a glycine at amino acid position 165 of SEQ ID NO: 64 is replaced with a serine, a methionine at amino acid position 282 of SEQ ID NO: 64 is replaced with a valine, a serine at amino acid position 509 of SEQ ID NO: 64 is replaced with a glycine, an asparagine at amino acid position 538 of SEQ ID NO: 64 is replaced with a lysine, or an asparagine at amino acid position 571 of SEQ ID NO: 64 is replaced with a serine; or wherein said synthetic piggyBac nucleic acid sequence encodes a hyperactive variant of an amino acid sequence consisting of SEQ ID NO: 65, wherein a methionine at amino acid position 194 of SEQ ID NO: 65 is replaced with a valine (SEQ ID NO: 108), and wherein an isoleucine at amino acid position 30 of SEQ ID NO: 65 is replaced with a valine, a serine at amino acid position 103 of SEQ ID NO: 65 is replaced with a proline, a glycine at amino acid position 165 of SEQ ID NO: 65 is replaced with a serine, a methionine at amino acid position 282 of SEQ ID NO: 65 is replaced with a valine, a serine at amino acid position 509 of SEQ ID NO: 65 is replaced with a glycine, an asparagine at amino acid position 538 of SEQ ID NO: 65 is replaced with a lysine, or an asparagine at amino acid position 571 of SEQ ID NO: 65 is replaced with a serine; or wherein said synthetic piggyBac nucleic acid sequence encodes a hyperactive variant of an amino acid sequence consisting of SEQ ID NO: 66, wherein a methionine at amino acid position 194 of SEQ ID NO: 66 is replaced with a valine and wherein an isoleucine at amino acid position 30 of SEQ ID NO: 66 is replaced with a valine, a serine at amino acid position 103 of SEQ ID NO: 66 is replaced with a proline, a glycine at amino acid position 165 of SEQ ID NO: 66 is replaced with a serine, a methionine at amino acid position 282 of SEQ ID NO: 66 is replaced with a valine, a serine at amino acid position 509 of SEQ ID NO: 66 is replaced with a glycine, an asparagine at amino acid position 538 of SEQ ID NO: 66 is replaced with a lysine, or an asparagine at amino acid position 571 of SEQ ID NO: 66 is replaced with a serine.

3. A transposon comprising a synthetic Noctuidae *Trichoplusia ni* piggyBac nucleic acid sequence, wherein said piggyBac nucleic acid sequence exhibits hyperactive piggyBac transposition activity, a higher level of piggyBac transposon excision, and a lower level of piggyBac transposon integration compared to a wildtype Noctuidae *Trichoplusia ni* piggyBac transposon, wherein said synthetic piggyBac nucleic acid sequence encodes a hyperactive variant of an amino acid sequence consisting of SEQ ID NO: 64, wherein a methionine at amino acid position 194 of SEQ ID NO: 64 is replaced with a valine (SEQ ID NO: 14), and wherein an isoleucine at amino acid position 30 of SEQ ID NO: 64 is replaced with a valine, a serine at amino acid position 103 of SEQ ID NO: 64 is replaced with a proline, a glycine at amino acid position 165 of SEQ ID NO: 64 is replaced with a serine, a methionine at amino acid position 282 of SEQ ID NO: 64 is replaced with a valine, a serine at amino acid position 509 of SEQ ID NO: 64 is replaced with a glycine, an asparagine at amino acid position 538 of SEQ ID NO: 64 is replaced with a lysine, and an asparagine at amino acid position 571 of SEQ ID NO: 64 is replaced with a serine; or wherein said synthetic piggyBac nucleic acid sequence encodes a hyperactive variant of an amino acid sequence consisting of SEQ ID NO: 65, wherein a methionine at amino acid position 194 of SEQ ID NO: 65 is replaced with a valine (SEQ ID NO: 108), and wherein an isoleucine at amino acid position 30 of SEQ ID NO: 65 is replaced with a valine, a serine at amino acid position 103 of SEQ ID NO: 65 is replaced with a proline, a glycine at amino acid position 165 of SEQ ID NO: 65 is replaced with a serine, a methionine at amino acid position 282 of SEQ ID NO: 65 is replaced with a valine, a serine at amino acid position 509 of SEQ ID NO: 65 is replaced with a glycine, an asparagine at amino acid position 538 of SEQ ID NO: 65 is replaced with a lysine, and an asparagine at amino acid position 571 of SEQ ID NO: 65 is replaced with a serine; or wherein said synthetic piggyBac nucleic acid sequence encodes a hyperactive variant of an amino acid sequence consisting of SEQ ID NO: 66, wherein a methionine at amino acid position 194 of SEQ ID NO: 66 is replaced with a valine, and wherein an isoleucine at amino acid position 30 of SEQ ID NO: 66 is replaced with a valine, a serine at amino acid position 103 of SEQ ID NO: 66 is replaced with a proline, a glycine at amino acid position 165 of SEQ ID NO: 66 is replaced with a serine, a methionine at amino acid position 282 of SEQ ID NO: 66 is replaced with a valine, a serine at amino acid position 509 of SEQ ID NO: 66 is replaced with a glycine, an asparagine at amino acid position 538 of SEQ ID NO: 66 is replaced with a lysine, and an asparagine at amino acid position 571 of SEQ ID NO: 66 is replaced with a serine.

4. The transposon of claim 1, wherein said wildtype Noctuidae *Trichoplusia ni* piggyBac transposon comprises the nucleic acid sequence set forth in SEQ ID NO: 1.

5. A gene transfer system comprising the transposon of claim 1 and a piggyBac transposase.

6. A cell comprising the transposon of claim 1.

7. A pharmaceutical composition comprising the transposon of claim 1, a piggyBac transposase, and a pharmaceutically acceptable carrier, adjuvant or vehicle.

8. A method for introducing exogenous DNA into a cell comprising:
contacting a cell with the gene transfer system of claim 5 and exogenous DNA, thereby introducing exogenous DNA into the cell.

9. The method of claim 8, wherein said cell comprises a stem cell.

10. A kit comprising the transposon of claim 1 and instructions for introducing DNA into a cell.

11. A transposon comprising a synthetic Noctuidae *Trichoplusia ni* piggyBac nucleic acid sequence, wherein said piggyBac nucleic acid sequence exhibits hyperactive piggyBac transposition activity and a lower level of piggyBac transposon integration compared to a wildtype Noctuidae *Trichoplusia ni* piggyBac transposon,
wherein said piggyBac nucleic acid sequence encodes a hyperactive variant of an amino acid sequence consisting of SEQ ID NO: 64, and wherein an isoleucine at amino acid position 30 of SEQ ID NO: 64 is replaced with a valine, a serine at amino acid position 103 of SEQ ID NO: 64 is replaced with a proline, a glycine at amino acid position 165 of SEQ ID NO: 64 is replaced with a serine, a methionine at amino acid position 282 of SEQ ID NO: 64 is replaced with a valine, a serine at amino acid position 509 of SEQ ID NO: 64 is replaced with a glycine, an asparagine at amino acid position 538 of SEQ ID NO: 64 is replaced with a lysine, or an asparagine at amino acid position 571 of SEQ ID NO: 64 is replaced with a serine; or
wherein said piggyback nucleic acid sequence encodes a hyperactive variant of an amino acid sequence consisting of SEQ ID NO: 65, and wherein an isoleucine at amino acid position 30 of SEQ ID NO: 65 is replaced with a valine, a serine at amino acid position 103 of SEQ ID NO: 65 is replaced with a proline, a glycine at amino acid position 165 of SEQ ID NO: 65 is replaced with a serine, a methionine at amino acid position 282 of SEQ ID NO: 65 is replaced with a valine, a serine at amino acid position 509 of SEQ ID NO: 65 is replaced with a glycine, an asparagine at amino acid position 538 of SEQ ID NO: 65 is replaced with a lysine, or an asparagine at amino acid position 571 of SEQ ID NO: 65 is replaced with a serine; or
wherein said piggyback nucleic acid sequence encodes a hyperactive variant of an amino acid sequence consisting of SEQ ID NO: 66, and wherein an isoleucine at amino acid position 30 of SEQ ID NO: 66 is replaced with a valine, a serine at amino acid position 103 of SEQ ID NO: 66 is replaced with a proline, a glycine at amino acid position 165 of SEQ ID NO: 66 is replaced with a serine, a methionine at amino acid position 282 of SEQ ID NO: 66 is replaced with a valine, a serine at amino acid position 509 of SEQ ID NO: 66 is replaced with a glycine, an asparagine at amino acid position 538 of SEQ ID NO: 66 is replaced with a lysine, or an asparagine at amino acid position 571 of SEQ ID NO: 66 is replaced with a serine.

12. A transposon comprising a synthetic Noctuidae *Trichoplusia ni* piggyBac nucleic acid sequence, wherein said piggyBac nucleic acid sequence exhibits hyperactive piggyBac transposition activity and a lower level of piggyBac transposon integration compared to a wildtype Noctuidae *Trichoplusia ni* piggyBac transposon,
wherein said piggyBac nucleic acid sequence encodes a hyperactive variant of an amino acid sequence consisting of SEQ ID NO: 64, and wherein an isoleucine at amino acid position 30 of SEQ ID NO: 64 is replaced with a valine, a serine at amino acid position 103 of SEQ ID NO: 64 is replaced with a proline, a glycine at amino acid position 165 of SEQ ID NO: 64 is replaced with a serine, a methionine at amino acid position 282 of SEQ ID NO: 64 is replaced with a valine, a serine at amino acid position 509 of SEQ ID NO: 64 is replaced with a glycine, an asparagine at amino acid position 538 of SEQ ID NO: 64 is replaced with a lysine, and an asparagine at amino acid position 571 of SEQ ID NO: 64 is replaced with a serine; or
wherein said piggyback nucleic acid sequence encodes a hyperactive variant of an amino acid sequence consisting of SEQ ID NO: 65, and wherein an isoleucine at amino acid position 30 of SEQ ID NO: 65 is replaced with a valine, a serine at amino acid position 103 of SEQ ID NO: 65 is replaced with a proline, a glycine at amino acid position 165 of SEQ ID NO: 65 is replaced with a serine, a methionine at amino acid position 282 of SEQ ID NO: 65 is replaced with a valine, a serine at amino acid position 509 of SEQ ID NO: 65 is replaced with a glycine, an asparagine at amino acid position 538 of SEQ ID NO: 65 is replaced with a lysine, and an asparagine at amino acid position 571 of SEQ ID NO: 65 is replaced with a serine; or
wherein said piggyback nucleic acid sequence encodes a hyperactive variant of an amino acid sequence consisting of SEQ ID NO: 66, and wherein an isoleucine at amino acid position 30 of SEQ ID NO: 66 is replaced with a valine, a serine at amino acid position 103 of SEQ ID NO: 66 is replaced with a proline, a glycine at amino acid position 165 of SEQ ID NO: 66 is replaced with a serine, a methionine at amino acid position 282 of SEQ ID NO: 66 is replaced with a valine, a serine at amino acid position 509 of SEQ ID NO: 66 is replaced with a glycine, an asparagine at amino acid position 538 of SEQ ID NO: 66 is replaced with a lysine, and an asparagine at amino acid position 571 of SEQ ID NO: 66 is replaced with a serine.

13. A transposon comprising a synthetic Noctuidae *Trichoplusia ni* piggyBac nucleic acid sequence, wherein said piggyBac nucleic acid sequence exhibits hyperactive piggyBac transposition activity,
wherein said piggyBac nucleic acid sequence encodes a hyperactive variant of an amino acid sequence comprising SEQ ID NO: 2, and
wherein an isoleucine at amino acid position 30 of SEQ ID NO: 2 is replaced with a valine, a serine at amino acid position 103 of SEQ ID NO: 2 is replaced with a proline, a glycine at amino acid position 165 of SEQ ID NO: 2 is replaced with a serine, a methionine at amino acid position 282 of SEQ ID NO: 2 is replaced with a valine, a serine at amino acid position 509 of SEQ ID NO: 2 is replaced with a glycine, an asparagine at amino acid position 538 of SEQ ID NO: 2 is replaced with a lysine, or an asparagine at amino acid position 571 of SEQ ID NO: 2 is replaced with a serine.

14. A transposon comprising a synthetic Noctuidae *Trichoplusia ni* piggyBac nucleic acid sequence, wherein said piggyBac nucleic acid sequence exhibits hyperactive piggyBac transposition activity,
   wherein said piggyBac nucleic acid sequence encodes a hyperactive variant of an amino acid sequence comprising SEQ ID NO: 2, and
   wherein an isoleucine at amino acid position 30 of SEQ ID NO: 2 is replaced with a valine, a serine at amino acid position 103 of SEQ ID NO: 2 is replaced with a proline, a glycine at amino acid position 165 of SEQ ID NO: 2 is replaced with a serine, a methionine at amino acid position 282 of SEQ ID NO: 2 is replaced with a valine, a serine at amino acid position 509 of SEQ ID NO: 2 is replaced with a glycine, an asparagine at amino acid position 538 of SEQ ID NO: 2 is replaced with a lysine, and an asparagine at amino acid position 571 of SEQ ID NO: 2 is replaced with a serine.

* * * * *

SEQUENCE LISTING

<160> NUMBER OF SEQ ID NOS: 130

<210> SEQ ID NO 1
<211> LENGTH: 2472
<212> TYPE: DNA
<213> ORGANISM: Trichoplusia ni

<400> SEQUENCE: 1

```
ccctagaaag atagtctgcg taaaattgac gcatgcattc ttgaaatatt gctctctctt        60
tctaaatagc gcgaatccgt cgctgtgcgt ttaggacatc tcagtcgccg cttggagctc       120
```

```
ccgtgaggcg tgcttgtcaa tgcggtaagt gtcactgatt ttgaactata acgaccgcgt    180
gagtcaaaat gacgcatgat tatcttttac gtgacttta agatttaact catacgataa     240
ttatattgtt atttcatgtt ctacttacgt gataacttat tatatatata ttttcttgtt   300
atagatatcg tgactaatat ataataaaat gggtagttct ttagacgatg agcatatcct   360
ctctgctctt ctgcaaagcg atgacgagct tgttggtgag gattctgaca gtgaaatatc   420
agatcacgta agtgaagatg acgtccagag cgatacagaa gaagcgttta tagatgaggt   480
acatgaagtg cagccaacgt caagcggtag tgaaatatta gacgaacaaa atgttattga   540
acaaccaggt tcttcattgg cttctaacaa aatcttgacc ttgccacaga ggactattag   600
aggtaagaat aaacattgtt ggtcaacttc aaagtccacg aggcgtagcc gagtctctgc   660
actgaatcat gtcagatctc aaagaggtcc gacgcgtatg tgccgcaata tatatgaccc   720
acttttatgc ttcaaactat tttttactga tgagataatt tcggaaattg taaaatggac   780
aaatgctgag atatcattga aacgtcggga atctatgaca ggtgctacat ttcgtgacac   840
gaatgaagat gaaatctatg ctttctttgg tattctggta atgacagcag tgagaaaaga   900
taaccacatg tccacagatg acctctttga tcgatctttg tcaatggtgt acgtctctgt   960
aatgagtcgt gatcgttttg atttttttgat acgatgtctt agaatggatg acaaaagtat  1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat tgtcgagag cataatattg atatgtgcca    2100
aagttgtttc tgactgacta ataagtataa tttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaatacaaca taaataaata gtttgttgaa tttattatta gtatgtaagt   2340
gtaaatataa taaacttaa tatctattca aattaataaa taaacctcga tatacagacc    2400
gataaaacac atgcgtcaat tttacgcatg attatcttta acgtacgtca caatatgatt   2460
```
atctttctag gg                                                                 2472

<210> SEQ ID NO 2
<211> LENGTH: 594
<212> TYPE: PRT
<213> ORGANISM: Trichoplusia ni

<400> SEQUENCE: 2

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 3
<211> LENGTH: 594
<212> TYPE: PRT
<213> ORGANISM: Trichoplusia ni

<400> SEQUENCE: 3

Met Gly Ser Ser Leu Asp Asp Glu His Ile Leu Ser Ala Leu Pro Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
            130                 135                 140

-continued

```
Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
            165                 170                 175

Tyr Ala Phe Phe Gly Ile Leu Val Met Thr Ala Val Arg Lys Asp Asn
        180                 185                 190

His Met Ser Thr Asp Asp Leu Phe Asp Arg Ser Leu Ser Met Val Tyr
    195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
            245                 250                 255

Gln Asn Tyr Thr Pro Gly Ala His Leu Thr Ile Asp Glu Gln Leu Leu
        260                 265                 270

Gly Phe Arg Gly Arg Cys Pro Phe Arg Met Tyr Ile Pro Asn Lys Pro
    275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
        340                 345                 350

Pro Leu Ala Lys Asn Leu Leu Gln Glu Pro Tyr Lys Leu Thr Ile Val
    355                 360                 365

Gly Thr Val Ala Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
        420                 425                 430

Pro Gln Met Val Met Tyr Tyr Asn Gln Thr Lys Gly Gly Val Asp Thr
    435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
        500                 505                 510

Ser Phe Met Arg Lys Arg Leu Glu Ala Pro Thr Leu Lys Arg Tyr Leu
    515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
```

```
                565                 570                 575
Cys Lys Lys Val Ile Cys Arg Glu His Asn Ile Asp Met Cys Gln Ser
            580                 585                 590
Cys Phe

<210> SEQ ID NO 4
<211> LENGTH: 594
<212> TYPE: PRT
<213> ORGANISM: Trichoplusia ni

<400> SEQUENCE: 4

Met Gly Ser Ser Leu Asp Asp Glu His Ile Leu Ser Ala Leu Leu Gln
1               5                   10                  15

Ser Asp Asn Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
```

```
                    340              345                 350
    Pro Leu Ala Lys Asn Leu Leu Gln Glu Pro Tyr Lys Leu Thr Ile Val
                355                  360                  365

Gly Thr Val Ala Ser Asn Lys Arg Glu Ile Pro Glu Val Leu Lys Asn
                370                  375                  380

Ser Arg Ser Arg Pro Val Gly Thr Ser Met Leu Cys Phe Asp Gly Pro
    385                  390                  395                  400

Leu Thr Leu Val Ser Tyr Lys Pro Lys Pro Ala Lys Met Val Tyr Leu
                     405                  410                  415

Leu Ser Ser Cys Asp Glu Asp Ala Ser Ile Asn Glu Ser Thr Gly Lys
                420                  425                  430

Pro Gln Met Val Met Tyr Tyr Asn Gln Thr Lys Gly Val Asp Thr
                435                  440                  445

Leu Asp Gln Met Cys Ser Val Met Thr Cys Ser Arg Lys Thr Asn Arg
                450                  455                  460

Trp Pro Met Ala Leu Leu Tyr Gly Met Ile Asn Ile Ala Cys Ile Asn
    465                  470                  475                  480

Ser Phe Ile Ile Tyr Ser His Asn Val Ser Ser Lys Gly Glu Lys Val
                     485                  490                  495

Gln Ser Arg Lys Lys Phe Met Arg Asn Leu Tyr Met Ser Leu Thr Ser
                500                  505                  510

Ser Phe Met Arg Lys Arg Leu Glu Ala Pro Thr Leu Lys Arg Tyr Leu
                515                  520                  525

Arg Asp Asn Ile Ser Asn Ile Leu Pro Asn Glu Val Pro Gly Thr Ser
    530                  535                  540

Asp Asp Ser Thr Glu Glu Pro Val Thr Lys Lys Arg Thr Tyr Cys Thr
    545                  550                  555                  560

Tyr Cys Pro Ser Lys Ile Arg Arg Lys Ala Asn Ala Ser Cys Lys Lys
                     565                  570                  575

Cys Lys Lys Val Ile Cys Arg Glu His Asn Ile Asp Met Cys Gln Ser
                580                  585                  590

Cys Phe

<210> SEQ ID NO 5
<211> LENGTH: 594
<212> TYPE: PRT
<213> ORGANISM: Trichoplusia ni

<400> SEQUENCE: 5

Met Gly Ser Ser Leu Asp Asp Glu His Ile Leu Ser Ala Leu Leu Gln
    1               5                   10                  15

Ser Asp Asp Glu Leu Val Gly Glu Asp Ser Asp Ser Glu Ile Pro Asp
                20                  25                  30

His Val Ser Glu Asp Val Gln Ser Asp Thr Glu Glu Ala Phe Ile
                35                  40                  45

Asp Glu Val His Glu Val Gln Pro Thr Ser Ser Gly Ser Glu Ile Leu
                50                  55                  60

Asp Glu Gln Asn Val Ile Glu Gln Pro Gly Ser Ser Leu Ala Ser Asn
    65                  70                  75                  80

Lys Ile Leu Thr Leu Pro Gln Arg Thr Ile Arg Gly Lys Asn Lys His
                    85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
```

-continued

```
            115                 120                 125
Tyr Asp Pro Leu Leu Cys Phe Lys Leu Phe Thr Asp Glu Ile Ile
    130                 135                 140
Ser Glu Ile Val Lys Trp Thr Asn Ala Glu Ile Ser Leu Lys Arg Arg
145                 150                 155                 160
Glu Ser Met Ala Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
            180                 185                 190
His Met Ser Thr Asp Asp Leu Phe Asp Arg Ser Leu Ser Met Val Tyr
        195                 200                 205
Val Ser Val Met Ser Arg Asp Arg Phe Asp Phe Leu Ile Arg Cys Leu
    210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Thr Lys
    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Asn
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
    450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
    530                 535                 540
```

```
Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 6
<211> LENGTH: 594
<212> TYPE: PRT
<213> ORGANISM: Trichoplusia ni

<400> SEQUENCE: 6

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

Tyr Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
        180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
        260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320
```

Gly Val Pro Leu Gly Glu Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
                355                 360                 365

Gly Thr Val Ala Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Asn Glu Val Pro Gly Thr Ser
            530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 7
<211> LENGTH: 594
<212> TYPE: PRT
<213> ORGANISM: Trichoplusia ni

<400> SEQUENCE: 7

Met Gly Ser Ser Leu Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Val Gln Ser Asp Thr Lys Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

```
Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
130             135                 140

Ser Glu Ile Val Lys Trp Thr Asn Ala Glu Ile Ser Leu Lys Arg Arg
145             150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305             310                 315                 320

Gly Val Pro Leu Gly Glu Tyr Tyr Val Lys Glu Leu Ser Arg Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385             390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465             470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510
```

```
Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 8
<211> LENGTH: 594
<212> TYPE: PRT
<213> ORGANISM: Trichoplusia ni

<400> SEQUENCE: 8

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Gly Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285
```

-continued

```
Ser Lys Tyr Gly Ile Lys Ile Leu Met Met Cys Asp Ser Gly Thr Lys
290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Asn
370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe

<210> SEQ ID NO 9
<211> LENGTH: 594
<212> TYPE: PRT
<213> ORGANISM: Trichoplusia ni

<400> SEQUENCE: 9

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
                20                  25                  30
His Val Ser Glu Asp Asp Val Gln Ser Asp Thr Glu Glu Ala Phe Ile
            35                  40                  45
Asp Glu Val His Glu Val Gln Pro Thr Ser Ser Gly Ser Glu Ile Leu
        50                  55                  60
```

```
Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Arg Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Ile Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
```

```
                    485                 490                 495
Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
        530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 10
<211> LENGTH: 594
<212> TYPE: PRT
<213> ORGANISM: Trichoplusia ni

<400> SEQUENCE: 10

Met Gly Ser Ser Leu Asp Asp Glu His Ile Leu Ser Ala Leu Leu Gln
1               5                   10                  15

Ser Asp Asp Glu Leu Val Gly Glu Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Pro Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
```

260                 265                 270
Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 11
<211> LENGTH: 594
<212> TYPE: PRT
<213> ORGANISM: Trichoplusia ni

<400> SEQUENCE: 11

Met Gly Ser Ser Leu Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile

```
            35                  40                  45
Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
                115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Lys Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
                290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Ala Ser Asn Lys Arg Glu Ile Pro Glu Val Leu Lys Asn
                370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460
```

```
Trp Pro Met Ala Leu Leu Tyr Gly Met Ile Asn Ile Ala Cys Ile Asn
465                 470                 475                 480

Ser Phe Ile Ile Tyr Ser His Asn Val Ser Lys Gly Glu Lys Val
            485                 490                 495

Gln Ser Arg Lys Lys Phe Met Arg Asn Leu Tyr Met Ser Leu Thr Ser
        500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 12
<211> LENGTH: 594
<212> TYPE: PRT
<213> ORGANISM: Trichoplusia ni

<400> SEQUENCE: 12

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Val Gln Ser Asp Thr Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Leu Ile Arg Cys Leu
    210                 215                 220

Arg Met Asp Asp Lys Ser Ile Arg Pro Thr Leu Arg Glu Asn Asp Val
225                 230                 235                 240
```

```
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Thr Lys
    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Asn
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asn Gln Met Cys Ser Val Met Thr Cys Ser Arg Lys Thr Asn Arg
    450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
    530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe

<210> SEQ ID NO 13
<211> LENGTH: 594
<212> TYPE: PRT
<213> ORGANISM: Trichoplusia ni

<400> SEQUENCE: 13

Met Gly Ser Ser Leu Asp Asp Glu His Ile Leu Ser Ala Leu Leu Gln
1               5                   10                  15
```

```
Ser Asp Asp Glu Leu Val Gly Glu Asp Ser Asp Ser Glu Ile Ser Asp
             20                  25                  30

His Val Ser Glu Asp Asp Val Gln Ser Asp Thr Glu Ala Phe Ile
             35                  40                  45

Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
             85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
            165                 170                 175

Tyr Ala Phe Phe Gly Ile Leu Val Met Thr Ala Val Arg Lys Asp Asn
            180                 185                 190

His Thr Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
            210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
            245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430
```

Pro Gln Met Val Met Tyr Tyr Asn Gln Thr Lys Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 14
<211> LENGTH: 594
<212> TYPE: PRT
<213> ORGANISM: Trichoplusia ni

<400> SEQUENCE: 14

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Val Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 15
<211> LENGTH: 594
<212> TYPE: PRT
<213> ORGANISM: Trichoplusia ni

<400> SEQUENCE: 15

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
```

```
                405                 410                 415
Leu Ser Ser Cys Asp Glu Asp Ala Ser Ile Asn Glu Ser Thr Gly Lys
            420                 425                 430
Pro Gln Met Ile Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
    450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
    530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe

<210> SEQ ID NO 16
<211> LENGTH: 594
<212> TYPE: PRT
<213> ORGANISM: Trichoplusia ni

<400> SEQUENCE: 16

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
            20                  25                  30
His Val Ser Glu Asp Val Gln Ser Asp Thr Glu Glu Ala Phe Ile
        35                  40                  45
Asp Glu Val His Glu Val Gln Pro Thr Ser Ser Gly Ser Glu Ile Leu
    50                  55                  60
Asp Glu Gln Asn Val Ile Glu Gln Pro Gly Ser Ser Leu Ala Ser Asn
65                  70                  75                  80
Lys Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
            100                 105                 110
Asn His Val Arg Ser Gln Arg Gly Pro Thr Arg Met Cys Arg Asn Ile
        115                 120                 125
Tyr Asp Pro Leu Leu Cys Phe Lys Leu Phe Phe Thr Asp Glu Ile Ile
    130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
```

```
             180                 185                 190
His Met Ser Thr Asp Asp Leu Phe Asp Arg Ser Leu Ser Met Val Tyr
             195                 200                 205

Val Ser Val Met Ser Arg Asp Arg Phe Asp Phe Leu Thr Arg Cys Leu
         210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                 245                 250                 255

Gln Asn Tyr Thr Pro Gly Ala His Leu Thr Ile Asp Glu Gln Leu Leu
             260                 265                 270

Gly Phe Arg Gly Arg Cys Pro Phe Arg Met Tyr Ile Pro Asn Lys Pro
         275                 280                 285

Ser Lys Tyr Gly Ile Lys Ile Leu Met Met Cys Asp Ser Gly Thr Lys
         290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                 325                 330                 335

His Gly Ser Cys Arg Asn Ile Thr Cys Asp Asn Trp Phe Thr Ser Ile
             340                 345                 350

Pro Leu Ala Lys Asn Leu Leu Gln Glu Pro Tyr Lys Leu Thr Ile Val
         355                 360                 365

Gly Thr Val Ala Ser Asn Lys Arg Glu Ile Pro Glu Val Leu Lys Asn
     370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                 405                 410                 415

Leu Ser Ser Cys Asp Glu Asp Ala Ser Ile Asn Glu Ser Thr Gly Lys
             420                 425                 430

Pro Gln Met Val Met Tyr Tyr Asn Gln Thr Lys Gly Gly Val Asp Thr
         435                 440                 445

Leu Asp Gln Met Cys Ser Val Met Thr Cys Ser Arg Lys Thr Asn Arg
     450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                 485                 490                 495

Gln Ser Arg Lys Lys Phe Met Arg Asn Leu Tyr Met Ser Leu Thr Ser
             500                 505                 510

Ser Phe Met Arg Lys Arg Leu Glu Ala Pro Thr Leu Lys Arg Tyr Leu
         515                 520                 525

Arg Asp Asn Ile Ser Asn Ile Leu Pro Asn Glu Val Pro Gly Thr Ser
     530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                 565                 570                 575

Cys Lys Lys Val Ile Cys Arg Glu His Asn Ile Asp Met Cys Gln Ser
             580                 585                 590

Cys Phe
```

<210> SEQ ID NO 17
<211> LENGTH: 594
<212> TYPE: PRT
<213> ORGANISM: Trichoplusia ni

<400> SEQUENCE: 17

```
Met Gly Ser Ser Leu Asp Asp Glu His Ile Leu Ser Ala Leu Leu Gln
 1               5                  10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Pro Asn Lys Arg Glu Ile Pro Glu Val Leu Lys Asn
370                 375                 380
```

```
Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 18
<211> LENGTH: 594
<212> TYPE: PRT
<213> ORGANISM: Trichoplusia ni

<400> SEQUENCE: 18

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
            130                 135                 140

Ser Glu Ile Val Lys Trp Thr Asn Ala Glu Ile Ser Leu Lys Arg Arg
145                 150                 155                 160
```

```
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
            180                 185                 190
His Met Ser Thr Asp Asp Leu Phe Asp Arg Ser Leu Ser Met Val Tyr
        195                 200                 205
Val Ser Val Met Ser Arg Asp Arg Phe Asp Phe Leu Ile Arg Cys Leu
    210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Thr Lys
    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Thr
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
    450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
    530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
```

```
Cys Lys Lys Val Ile Cys Arg Glu His Asn Ile Asp Met Cys Gln Ser
            580                 585                 590

Cys Phe

<210> SEQ ID NO 19
<211> LENGTH: 594
<212> TYPE: PRT
<213> ORGANISM: Trichoplusia ni

<400> SEQUENCE: 19

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350
```

```
Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Ser Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Thr Lys Arg Thr Tyr Cys Thr
545                 550                 555                 560

Tyr Cys Pro Ser Lys Ile Arg Arg Lys Ala Ser Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 20
<211> LENGTH: 594
<212> TYPE: PRT
<213> ORGANISM: Trichoplusia ni

<400> SEQUENCE: 20

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
            35                  40                  45

Asp Glu Val His Glu Val Gln Pro Thr Ser Gly Ser Glu Ile Leu
            50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125
```

```
Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Gly Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Ala
```

```
            545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 21
<211> LENGTH: 594
<212> TYPE: PRT
<213> ORGANISM: Trichoplusia ni

<400> SEQUENCE: 21

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
            130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Leu Ile Arg Cys Leu
            210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
```

```
                    325                 330                 335
His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Ser Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 22
<211> LENGTH: 594
<212> TYPE: PRT
<213> ORGANISM: Trichoplusia ni

<400> SEQUENCE: 22

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
```

```
            100                 105                 110
Asn His Val Arg Ser Gln Arg Gly Pro Thr Arg Met Cys Arg Asn Ile
            115                 120                 125
Tyr Asp Pro Leu Leu Cys Phe Lys Leu Phe Phe Thr Asp Glu Ile Ile
130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
                    165                 170                 175
Tyr Ala Phe Phe Gly Ile Leu Val Met Thr Ala Val Arg Lys Asp Asn
                    180                 185                 190
His Met Ser Thr Asp Asp Leu Phe Asp Arg Ser Leu Ser Met Val Tyr
                    195                 200                 205
Val Ser Val Met Ser Arg Asp Arg Phe Asp Phe Leu Ile Arg Cys Leu
                    210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                    245                 250                 255
Gln Asn Tyr Thr Pro Gly Ala His Leu Thr Ile Asp Glu Gln Leu Leu
                    260                 265                 270
Gly Phe Arg Gly Arg Cys Pro Phe Arg Met Tyr Ile Pro Asn Lys Pro
                    275                 280                 285
Ser Lys Tyr Gly Ile Lys Ile Leu Met Met Cys Asp Ser Gly Thr Lys
                    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                    325                 330                 335
His Gly Ser Cys Arg Asn Ile Thr Cys Asp Asn Trp Phe Thr Ser Ile
                    340                 345                 350
Pro Leu Ala Lys Asn Leu Leu Gln Glu Pro Tyr Lys Leu Thr Ile Val
                    355                 360                 365
Gly Thr Val Ala Ser Asn Lys Arg Glu Ile Pro Glu Val Leu Lys Asn
                    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                    405                 410                 415
Leu Ser Ser Cys Asp Glu Asp Ala Ser Ile Asn Glu Ser Thr Gly Lys
                    420                 425                 430
Pro Gln Met Val Met Tyr Tyr Asn Gln Thr Lys Gly Gly Val Asp Thr
            435                 440                 445
Leu Asp Gln Met Cys Ser Val Met Thr Cys Ser Arg Lys Thr Asn Arg
            450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                    485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
            515                 520                 525
```

```
Arg Asp Asn Ile Ser Asn Ile Leu Pro Asn Glu Val Pro Gly Thr Ser
            530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ala Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 23
<211> LENGTH: 594
<212> TYPE: PRT
<213> ORGANISM: Trichoplusia ni

<400> SEQUENCE: 23

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300
```

```
Tyr Met Ile Asn Gly Met Pro Tyr Leu Gly Arg Gly Thr Gln Thr Asn
305                 310                 315                 320

Gly Val Pro Leu Gly Glu Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 24
<211> LENGTH: 594
<212> TYPE: PRT
<213> ORGANISM: Trichoplusia ni

<400> SEQUENCE: 24

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Gly Ser Glu Ile Leu
    50                  55                  60

Asp Glu Gln Asn Val Ile Glu Gln Pro Gly Ser Ser Leu Ala Ser Asn
65                  70                  75                  80
```

```
Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
                115                 120                 125

Tyr Asp Pro Leu Leu Cys Phe Lys Leu Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Phe Leu Ile Arg Cys Leu
                210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
                290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495
```

```
Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Val Cys Gln Ser
            580                 585                 590

Cys Phe

<210> SEQ ID NO 25
<211> LENGTH: 594
<212> TYPE: PRT
<213> ORGANISM: Trichoplusia ni

<400> SEQUENCE: 25

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270
```

```
Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
    435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
    515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Val Cys Gln Ser
            580                 585                 590

Cys Phe

<210> SEQ ID NO 26
<211> LENGTH: 594
<212> TYPE: PRT
<213> ORGANISM: Trichoplusia ni

<400> SEQUENCE: 26

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45
```

```
Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
                115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
                290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Ala Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
```

-continued

```
                465                 470                 475                 480
            Ser Phe Ile Ile Tyr Ser His Asn Val Ser Ser Lys Gly Glu Lys Val
                            485                 490                 495
            Gln Ser Arg Lys Lys Phe Met Arg Asn Leu Tyr Met Ser Leu Thr Ser
                            500                 505                 510
            Ser Phe Met Arg Lys Arg Leu Glu Ala Pro Thr Leu Lys Arg Tyr Leu
                            515                 520                 525
            Arg Asp Asn Ile Ser Asn Ile Leu Pro Asn Glu Val Pro Gly Thr Ser
            530                 535                 540
            Asp Asp Ser Thr Glu Glu Pro Val Thr Lys Lys Arg Thr Tyr Cys Thr
            545                 550                 555                 560
            Tyr Cys Pro Ser Lys Ile Arg Arg Lys Ala Asn Ala Ser Cys Lys Lys
                            565                 570                 575
            Cys Lys Lys Val Ile Cys Arg Glu His Asn Ile Asp Met Cys Gln Gly
                            580                 585                 590
            Cys Phe

<210> SEQ ID NO 27
<211> LENGTH: 594
<212> TYPE: PRT
<213> ORGANISM: Trichoplusia ni

<400> SEQUENCE: 27

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
                20                  25                  30
His Val Ser Glu Asp Asp Val Gln Ser Asp Thr Glu Glu Ala Phe Ile
            35                  40                  45
Asp Glu Val His Glu Val Gln Pro Thr Ser Ser Gly Ser Glu Ile Leu
        50                  55                  60
Asp Glu Gln Asn Val Ile Glu Gln Pro Gly Ser Ser Leu Ala Ser Asn
65                  70                  75                  80
Lys Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
                100                 105                 110
Asn His Val Arg Ser Gln Arg Gly Pro Thr Arg Met Cys Arg Asn Ile
            115                 120                 125
Tyr Asp Pro Leu Leu Cys Phe Lys Leu Phe Thr Asp Glu Ile Ile
        130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
                180                 185                 190
His Met Ser Thr Asp Asp Leu Phe Asp Arg Ser Leu Ser Met Val Tyr
            195                 200                 205
Val Ser Val Met Ser Arg Asp Arg Phe Asp Phe Leu Ile Arg Cys Leu
        210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
```

```
            245                 250                 255
Gln Asn Tyr Thr Pro Gly Ala His Leu Thr Ile Asp Glu Gln Leu Leu
        260                 265                 270

Gly Phe Arg Gly Arg Cys Pro Phe Arg Met Tyr Ile Pro Asn Lys Pro
    275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Leu

<210> SEQ ID NO 28
<211> LENGTH: 600
<212> TYPE: PRT
<213> ORGANISM: Trichoplusia ni

<400> SEQUENCE: 28

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
```

```
                20                  25                  30
        His Val Ser Glu Asp Val Gln Ser Asp Thr Glu Ala Phe Ile
                    35                  40                  45
        Asp Glu Val His Glu Val Gln Pro Thr Ser Ser Gly Ser Glu Ile Leu
        50                  55                  60
        Asp Glu Gln Asn Val Ile Glu Gln Pro Gly Ser Ser Leu Ala Ser Asn
        65                  70                  75                  80
        Lys Ile Leu Thr Leu Pro Gln Arg Thr Ile Arg Gly Lys Asn Lys His
                        85                  90                  95
        Cys Trp Ser Thr Ser Lys Ser Thr Arg Arg Ser Arg Val Ser Ala Leu
                        100                 105                 110
        Asn His Val Arg Ser Gln Arg Gly Pro Thr Arg Met Cys Arg Asn Ile
                    115                 120                 125
        Tyr Asp Pro Leu Leu Cys Phe Lys Leu Phe Phe Thr Asp Glu Ile Ile
                    130                 135                 140
        Ser Glu Ile Val Lys Trp Thr Asn Ala Glu Ile Ser Leu Lys Arg Arg
        145                 150                 155                 160
        Glu Ser Met Thr Gly Ala Thr Phe Arg Asp Thr Asn Glu Asp Glu Ile
                        165                 170                 175
        Tyr Ala Phe Phe Gly Ile Leu Val Met Thr Ala Val Arg Lys Asp Asn
                    180                 185                 190
        His Met Ser Thr Asp Asp Leu Phe Asp Arg Ser Leu Ser Met Val Tyr
                    195                 200                 205
        Val Ser Val Met Ser Arg Asp Arg Phe Asp Phe Leu Ile Arg Cys Leu
                    210                 215                 220
        Arg Met Asp Asp Lys Ser Ile Arg Pro Thr Leu Arg Glu Asn Asp Val
        225                 230                 235                 240
        Phe Thr Pro Val Arg Lys Ile Trp Asp Leu Phe Ile His Gln Cys Ile
                        245                 250                 255
        Gln Asn Tyr Thr Pro Gly Ala His Leu Thr Ile Asp Glu Gln Leu Leu
                    260                 265                 270
        Gly Phe Arg Gly Arg Cys Pro Phe Arg Met Tyr Ile Pro Asn Lys Pro
                    275                 280                 285
        Ser Lys Tyr Gly Ile Lys Ile Leu Met Met Cys Asp Ser Gly Thr Lys
        290                 295                 300
        Tyr Met Ile Asn Gly Met Pro Tyr Leu Gly Arg Gly Thr Gln Thr Asn
        305                 310                 315                 320
        Gly Val Pro Leu Gly Glu Tyr Tyr Val Lys Glu Leu Ser Lys Pro Val
                        325                 330                 335
        His Gly Ser Cys Arg Asn Ile Thr Cys Asp Asn Trp Phe Thr Ser Ile
                    340                 345                 350
        Pro Leu Ala Lys Asn Leu Leu Gln Glu Pro Tyr Lys Leu Thr Ile Val
                    355                 360                 365
        Gly Thr Val Ala Ser Asn Lys Arg Glu Ile Pro Glu Val Leu Lys Asn
                    370                 375                 380
        Ser Arg Ser Arg Pro Val Gly Thr Ser Met Phe Cys Phe Asp Gly Pro
        385                 390                 395                 400
        Leu Thr Leu Val Ser Tyr Lys Pro Lys Pro Ala Lys Met Val Tyr Leu
                        405                 410                 415
        Leu Ser Ser Cys Asp Glu Asp Ala Ser Ile Asn Glu Ser Thr Gly Lys
                    420                 425                 430
        Pro Gln Met Val Met Tyr Tyr Asn Gln Thr Lys Gly Gly Val Asp Thr
                    435                 440                 445
```

```
Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe Trp Leu Glu Ser Cys Asn
        595                 600

<210> SEQ ID NO 29
<211> LENGTH: 600
<212> TYPE: PRT
<213> ORGANISM: Trichoplusia ni

<400> SEQUENCE: 29

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
```

```
                210               215               220
Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
                290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Ala Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
                450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Asn Glu Val Pro Gly Thr Ser
                530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe Glu Leu Glu Ser Cys Asn
                595                 600

<210> SEQ ID NO 30

<400> SEQUENCE: 30
```

<210> SEQ ID NO 31

<400> SEQUENCE: 31

000

<210> SEQ ID NO 32

<400> SEQUENCE: 32

000

<210> SEQ ID NO 33
<211> LENGTH: 594
<212> TYPE: PRT
<213> ORGANISM: Trichoplusia ni

<400> SEQUENCE: 33

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
```

```
              290                 295                 300
Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 34
<211> LENGTH: 2472
<212> TYPE: DNA
<213> ORGANISM: Trichoplusia ni

<400> SEQUENCE: 34
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttttac gtgactttta agatttaact catacgataa    240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ccgcaaagcg atgacgagct tgttggtgag gattctgaca gtgaaatatc     420
```

```
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa atcttgacc ttgccacaga ggactattag     600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaatat gggatctctt    1080 tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aaccttaca tgagcctgac     1860 gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaagttat tgtcgagag cataatattg atatgtgcca     2100
aagttgtttc tgactgacta ataagtataa tttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatctta acgtacgtca caatatgatt    2460
atctttctag gg                                                      2472
```

<210> SEQ ID NO 35
<211> LENGTH: 2472
<212> TYPE: DNA
<213> ORGANISM: Trichoplusia ni

<400> SEQUENCE: 35

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg ataacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat tcgtgacac      840 gaatgaagat gaaatctatg ctttctttgg tattctggta atgacagcag tgagaaaaga     900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
ggcatcaaac aaacgcgaga taccggaagt actgaaaaac agtcgctcca ggccagtggg    1500
aacatcgatg ctttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttgta     2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
```

```
gataaaacac atgcgtcaat tttacgcatg attatcttta acgtacgtca caatatgatt    2460
atctttctag gg                                                         2472

<210> SEQ ID NO 36
<211> LENGTH: 2472
<212> TYPE: DNA
<213> ORGANISM: Trichoplusia ni

<400> SEQUENCE: 36
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatacc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatggca ggtgctacat tcgtgacac      840 gaatgaagat gaaatctatg ctttctttgg tattctggta atgacagcag tgagaaaaga     900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat tgaccatag atgaacagtt     1140 acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttttg gcaaaaaact tactacaaga accgtataag ttaaccattg tgggaaccgt    1440
ggcatcaaac aaacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct gcataaattc ttttattata tacagccata atgtcagtag     1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
```

| | |
|---|---|
| agtaacgaaa aaacgtactt actgtactta ctgcccctct aaaataaggc gaaaggcaaa | 2040 |
| tgcatcgtgc aaaaaatgca aaaaagttat ttgtcgagag cataatattg atatgtgcca | 2100 |
| aagttgtttc tgactgacta ataagtataa tttgtttcta ttatgtataa gttaagctaa | 2160 |
| ttacttattt tataatacaa catgactgtt tttaaagtac aaaataagtt tatttttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 37
<211> LENGTH: 2472
<212> TYPE: DNA
<213> ORGANISM: Trichoplusia ni

<400> SEQUENCE: 37

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttttac gtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agattacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttttactga tgagataatt tcggaaattg taaaatggac | 780 |
| aaaatgctgag atatcattga aacgtcggga atctatgaca ggtgctacat ttcgtgacac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg attttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatcccttg gcaaaaaact tactacaaga accgtataag ttaaccattg tgggaaccgt | 1440 |
| ggcatcaaac aaacgcgaga taccggaagt actgaaaaac agtcgctcca ggccagtggg | 1500 |
| aacatcgatg ttttgttttg acggaccccct tactctcgtc tcatataaac cgaagccagc | 1560 |
| taagatggta tacttattat catcttgtga tgaggatgct tctatcaacg aaagtaccgg | 1620 |

```
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct gcataaattc ttttattata tacagccata atgtcagtag     1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat tgtcgagag cataatattg atatgtgcca     2100
aagttgtttc tgactgacta ataagtataa tttgtttcta ttatgtataa gttaagctaa    2160
ttacttattt tataatacaa catgactgtt tttaaagtac aaaataagtt tattttgta     2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472

<210> SEQ ID NO 38
<211> LENGTH: 2472
<212> TYPE: DNA
<213> ORGANISM: Trichoplusia ni

<400> SEQUENCE: 38
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgacttta agatttaact catacgataa      240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacaaaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
```

| | |
|---|---:|
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaagg cctgtgcacg gtagttgtcg taatattacg tgtgacaatt ggttcacctc | 1380 |
| aatccctttg gcaaaaaact tactacaaga accgtataag ttaaccattg tgggaaccgt | 1440 |
| ggcatcaaac aaacgcgaga taccggaagt actgaaaaac agtcgctcca ggccagtggg | 1500 |
| aacatcgatg ttttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata acattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat attttgccaa atgaagtgcc tggtacatca gatgacagta ctgaagagcc | 1980 |
| agtaacgaaa aaacgtactt actgtactta ctgcccctct aaaataaggc gaaaggcaaa | 2040 |
| tgcatcgtgc aaaaaatgca aaaaagttat tgtcgagag cataatattg atatgtgcca | 2100 |
| aagttgtttc tgactgacta ataagtataa tttgtttcta ttatgtataa gttaagctaa | 2160 |
| ttacttattt tataatacaa catgactgtt tttaaagtac aaaataagtt tattttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaacttaa tatctattca aattaataaa taaacctcga tatacagacc | 2400 |
| gataaaacac atgcgtcaat tttacgcatg attatcttta acgtacgtca caatatgatt | 2460 |
| atcttttctag gg | 2472 |

<210> SEQ ID NO 39
<211> LENGTH: 2472
<212> TYPE: DNA
<213> ORGANISM: Trichoplusia ni

<400> SEQUENCE: 39

| | |
|---|---:|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatcttttac gtgacttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa ggagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat tttttactga tgagataatt tcggaaattg taaaatggac | 780 |
| aaatgctgag atatcattga aacgtcggga atctatgaca ggtgctacat tcgtgacac | 840 |

```
gaatgaagat gaaatctatg cttcctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata acattgcctg cataaaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaagttat ttgtcgagag cataatattg atatgtgcca    2100
aagttgtttc tgactgacta ataagtataa ttttgtttcta ttatgtataa gttaagctaa   2160
ttacttattt tataatacaa catgactgtt tttaaagtac aaaataagtt tatttttgta    2220
aaagagagaa tgttaaaaag ttttgttact ttatagaaga aattttgagt ttttgttttt   2280
ttttaataaa taaataaaca taaataaata gtttgttgaa tttattatta gtatgtaagt   2340
gtaaatataa taaacttaa tatctattca aattaataaa taaacctcga tatacagacc    2400
gataaaacac atgcgtcaat tttacgcatg attatcttta acgtacgtca caatatgatt   2460
atctttctag gg                                                       2472

<210> SEQ ID NO 40
<211> LENGTH: 2472
<212> TYPE: DNA
<213> ORGANISM: Trichoplusia ni

<400> SEQUENCE: 40
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttac gtgacttta agatttaact catacgataa      240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
```

```
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa atcttgacc ttgccacaga ggactattag     600
aggtaagaat aaacatcgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tattcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat tgtcgagag cataatattg atatgtgcca    2100
aagttgtttc tgactgacta ataagtataa tttgtttcta ttatgtataa gttaagctaa   2160
ttacttattt tataatacaa catgactgtt tttaaagtac aaaataagtt tattttttgta  2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 41
<211> LENGTH: 2472
<212> TYPE: DNA
<213> ORGANISM: Trichoplusia ni

<400> SEQUENCE: 41

```
ccctagaaag atagtctgcg taaaattgac gcatgcattc ttgaaatatt gctctctctt     60
```

```
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgacttttta agatttaact catacgataa   240
ttatattgtt atttcatgtt ctacttacgt gataaacttat tatatatata ttttcttgtt   300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagcccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg cttctcttgg tattctggta atgacagcag tgagaaaaga    900
taaccacatg tccacagatg acctctttga tcgatcttttg tcaatggtgt acgtctctgt   960
aatgagtcgt gatcgttttg atttttttgat acgatgtctt agaatggatg acaaaagtat   1020
acggcccaca cttcgagaaa acgatgtatt tactcctgtt agaaaaatat gggatctctt    1080
tatccatcag tgcatacaaa attacactcc agggggctcat ttgaccatag atgaacagtt   1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
ggcatcaaac aaacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc tttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
```

```
gataaaacac atgcgtcaat tttacgcatg attatcttta acgtacgtca caatatgatt    2460
atctttctag gg                                                         2472

<210> SEQ ID NO 42
<211> LENGTH: 2472
<212> TYPE: DNA
<213> ORGANISM: Trichoplusia ni

<400> SEQUENCE: 42
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgc     180
gagtcaaaat gacgcatgat tatctttttac gtgacttttta agatttaact catacgataa    240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggccc gacgcgtatg tgccgcaata tatatgaccc     720
acttttatgc ttcaaactat ttttttactga tgagataatt tcggaaattg taaaatggac    780
aaatgctgag atatcattga aacgtcggga atctatgaca ggtgctacat tcgtgacac      840 gaatgaagat gaaatctatg ctttctttgg tattctggta atgacagcag tgaaaaaaga     900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttg gcaaaaaact tactacaaga accgtataag ttaaccattg tgggaaccgt     1440
ggcatcaaac aaacgcgaga taccggaagt actgaaaaac agtcgctcca ggccagtggg    1500
aacatcgatg ttttgttttg acggaccct tactctcgtc tcatataaac cgaagccagc     1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc tttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgccctctc aaaataaggc gaaaggcaaa    2040
```

-continued

```
tgcatcgtgc aaaaaatgca aaaaagttat ttgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

```
<210> SEQ ID NO 43
<211> LENGTH: 2472
<212> TYPE: DNA
<213> ORGANISM: Trichoplusia ni

<400> SEQUENCE: 43
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg ctttctttgg tattctggta atgacagcag tgaggaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
```

```
taaaccgcaa atggttatgt attataatca aactaaaggc ggagtggaca cgctaaacca    1680
aatgtgttct gtgatgacct gcagtaggaa gacgaatagg tggcctatgg cattattgta    1740
cggaatgata acattgcct gcataaattc ttttattata tacagccata atgtcagtag     1800
caagggagaa aaggttcaaa gtcgcaaaaa atttatgaga aacctttaca tgagcctgac    1860
gtcatcgttt atgcgtaagc gtttagaagc tcctactttg aagaggtatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat tgtcgagag cataatattg atatgtgcca     2100
aagttgtttc tgactgacta ataagtataa tttgtttcta ttatgtataa gttaagctaa    2160
ttacttattt tataatacaa catgactgtt tttaaagtac aaaataagtt tattttgta    2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472

<210> SEQ ID NO 44
<211> LENGTH: 2472
<212> TYPE: DNA
<213> ORGANISM: Trichoplusia ni

<400> SEQUENCE: 44
ccctagaaag atagtctgcg taaaattgac gcatgcattc ttgaaatatt gctctctctt    60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgacttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat ttttactga tgagataatt tcggaaattg taaaatggac    780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacacg tccacagatg acctctttga tcgatctttg tcaatggtgt acgtctctgt    960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
```

```
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttttg gcaaaaaact tactacaaga accgtataag ttaaccattg tgggaaccgt   1440
ggcatcaaac aaacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct gcataaattc ttttattata tacagccata atgtcagtag     1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472

<210> SEQ ID NO 45
<211> LENGTH: 2472
<212> TYPE: DNA
<213> ORGANISM: Trichoplusia ni

<400> SEQUENCE: 45
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttac gtgacttttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat ttttactga tgagataatt tcggaaattg taaaatggac     780
aaatgctgag atatcattga aacgtcggga atctatgaca ggtgctacat tcgtgacac     840
```

```
gaatgaagat gaaatctatg cttcctttgg tattctggta atgacagcag tgagaaaaga      900
taaccacgtg tccacagatg acctctttga tcgatctttg tcaatggtgt acgtctctgt      960
aatgagtcgt gatcgttttg atttttttgat acgatgtctt agaatggatg acaaaagtat   1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga gaggaacaca gaccaacgg agtaccactc ggtgaatact acgtgaagga     1320
gttatcaaag cctgtgcacg gtagttgtcg taatattacg tgtgacaatt ggttcacctc    1380
aatcccttg gcaaaaaact tactacaaga accgtataag ttaaccattg tgggaaccgt     1440
ggcatcaaac aaacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc ttttattata tacagccata atgtcagtag   1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat tgtcgagag cataatattg atatgtgcca     2100
aagttgtttc tgactgacta ataagtataa tttgtttcta ttatgtataa gttaagctaa    2160
ttacttattt tataatacaa catgactgtt tttaaagtac aaaataagtt tattttttgta   2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatctttta acgtacgtca caatatgatt   2460
atctttctag gg                                                        2472

<210> SEQ ID NO 46
<211> LENGTH: 2472
<212> TYPE: DNA
<213> ORGANISM: Trichoplusia ni

<400> SEQUENCE: 46
ccctagaaag atagtctgcg taaaattgac gcatgcattc ttgaaatatt gctctctctt       60
tctaaatagc gcgaatccgt cgctgtgcgt ttaggacatc tcagtcgccg cttggagctc      120
ccgtgaggcg tgcttgtcaa tgcggtaagt gtcactgatt ttgaactata acgaccgcgt      180
gagtcaaaat gacgcatgat tatctttttac gtgacttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
```

```
acatgaagtg cagccaacgt caagcggtag tgaaatatta gacgaacaaa atgttattga        540
acaaccaggt tcttcattgg cttctaacaa aatcttgacc ttgccacaga ggactattag        600
aggtaagaat aaacattgtt ggtcaacttc aaagtccacg aggcgtagcc gagtctctgc        660
actgaatcat gtcagatctc aaagaggtcc gacgcgtatg tgccgcaata tatatgaccc        720
acttttatgc ttcaaactat tttttactga tgagataatt tcggaaattg taaaatggac        780
aaatgctgag atatcattga aacgtcggga atctatgaca ggtgctacat ttcgtgacac        840
gaatgaagat gaaatctatg cttctcttgg tattctggta atgacagcag tgagaaaaga        900
taaccacatg tccacagatg acctctttga tcgatctttg tcaatggtgt acgtctctgt        960
aatgagccgt gatcgttttg attttttgat acgatgtctt agaatggatg acaaaagtat       1020
acggcccaca cttcgagaaa acgatgtatt tactcctgtt agaaaaatat gggatctctt       1080
tatccatcag tgcatacaaa attacactcc aggggctcat ttgaccatag atgaacagtt       1140
acttggtttt agaggacggt gtccgtttag gatgtatatc ccaaacaagc caagtaagta       1200
tggaataaaa atcctcatga tgtgtgacag tggtacaaag tatatgataa atggaatgcc       1260
ttatttggga agaggaacac agaccaacgg agtaccactc ggtgaatact acgtgaagga       1320
gttatcaaag cctgtgcacg gtagttgtcg taatattacg tgtgacaatt ggttcacctc       1380 aatcccttg gcaaaaaact tactacaaga accgtataag ttaaccattg tgggaaccgt        1440
ggcatcaaac aaacgcgaga taccggaagt actgaaaaac agtcgctcca ggccagtggg       1500
aacatcgatg ttttgttttg acggacccct tactctcgtc tcatataaac cgaagccagc       1560
taagatggta tacttattat catcttgtga tgaggatgct tctatcaacg aaagtaccgg       1620
taaaccgcaa atggttatgt attataatca aactaaaggc ggagtggaca cgctagacca       1680
aatgtgttct gtgatgacct gcagtaggaa gacgaatagg tggcctatgg cattattgta       1740
cggaatgata aacattgcct gcataaattc ttttattata tacagccata atgtcagtag       1800
caagggagaa aaggttcaaa gtcgcaaaaa atttatgaga aacctttaca tgagcctgac       1860
gtcatcgttt atgcgtaagc gtttagaagc tcctactttg aagagatatt tgcgcgataa       1920
tatctctaat attttgccaa atgaagtgcc tggtacatca gatgacagta ctgaagagcc       1980
agtaacgaaa aaacgtactt actgtactta ctgcccctct aaaataaggc gaaaggcaaa       2040
tgcatcgtgc aaaaaatgca aaaaagttat tgtcgagag cataatattg atatgtgcca        2100
aagttgtttc tgactgacta ataagtataa tttgtttcta ttatgtataa gttaagctaa       2160
ttacttattt tataatacaa catgactgtt tttaaagtac aaaataagtt tatttttgta       2220
aaagagagaa tgtttaaaag ttttgttact ttatagaaga aattttgagt ttttgttttt       2280
ttttaataaa taaataaaca taaataaata gtttgttgaa tttattatta gtatgtaagt       2340
gtaaatataa taaaacttaa tatctattca aattaataaa taaacctcga tatacagacc       2400
gataaaacac atgcgtcaat tttacgcatg attatcttta acgtacgtca caatatgatt       2460
atctttctag gg                                                           2472
```

<210> SEQ ID NO 47
<211> LENGTH: 2472
<212> TYPE: DNA
<213> ORGANISM: Trichoplusia ni

<400> SEQUENCE: 47

```
ccctagaaag atagtctgcg taaaattgac gcatgcattc ttgaaatatt gctctctctt         60
```

```
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg atttttttgac acgatgtctt agaatggatg acaaagtat   1020 acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggaccccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat atttttgccaa atgaagtgcc tggtacatca gatgacagta ctgaagagcc   1980
agtaacgaaa aaacgtactt actgtactta ctgccccctct aaaataaggc gaaaggcaaa   2040
tgcatcgtgc aaaaaatgca aaaaagttat ttgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttttgta   2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatctttta acgtacgtca caatatgatt   2460
```

| | |
|---|---|
| atctttctag gg | 2472 |

<210> SEQ ID NO 48
<211> LENGTH: 2472
<212> TYPE: DNA
<213> ORGANISM: Trichoplusia ni

<400> SEQUENCE: 48

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttac gtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| actttatgc ttcaaactat tttttactga tgagataatt tcggaaattg taaaatggac | 780 |
| aaatgctgag atatcattga aacgtcggga atctatgaca ggtgctacat ttcgtgacac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg atttttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatcccttg gcaaaaaact tactacaaga accgtataag ttaaccattg tgggaaccgt | 1440 |
| ggcaccaaac aaacgcgaga taccggaagt actgaaaaac agtcgctcca ggccagtggg | 1500 |
| aacatcgatg ttttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata aacattgcct gcataaaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat attttgccaa atgaagtgcc tggtacatca gatgacagta ctgaagagcc | 1980 |
| agtaacgaaa aaacgtactt actgtactta ctgcccctct aaaataaggc gaaaggcaaa | 2040 |

```
tgcatcgtgc aaaaaatgca aaaaagttat tgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttgta     2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaacttaa tatctattca aattaataaa taaacctcga tatacagacc     2400
gataaaacac atgcgtcaat tttacgcatg attatcttta acgtacgtca caatatgatt    2460
atctttctag gg                                                        2472

<210> SEQ ID NO 49
<211> LENGTH: 2472
<212> TYPE: DNA
<213> ORGANISM: Trichoplusia ni

<400> SEQUENCE: 49
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgacttta agatttaact catacgataa      240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtc cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat tcgtgacac      840 gaatgaagat gaaatctatg cttttctttgg tattctggta atgacagcag tgagaaaaga    900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
ggcatcaaac aaacgcgaga taccggaagt actgaaaacc agtcgctcca ggccagtggg    1500
aacatcgatg ttttgttttg acggacccct tactctcgtc tcatataaac cgaagccagc    1560
taagatggta tacttattat catccttgtga tgaggatgct tctatcaacg aaagtaccgg    1620
taaaccgcaa atggttatgt attataatca aactaaaggc ggagtggaca cgctagacca    1680
```

```
aatgtgttct gtgatgacct gcagtaggaa gacgaatagg tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat tgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttgta    2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                         2472

<210> SEQ ID NO 50
<211> LENGTH: 2472
<212> TYPE: DNA
<213> ORGANISM: Trichoplusia ni

<400> SEQUENCE: 50
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720 actttatgc ttcaaactat ttttactga tgagataatt tcggaaattg taaaatggac    780
aaatgctgag atatcattga aacgtcggga atctatgaca ggtgctacat tcgtgacac    840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaatat gggatctctt    1080 tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
```

```
ttatttggga agaggaacac agaccaacgg agtaccactc ggtgaatact acgtgaagga      1320
gttatcaaag cctgtgcacg gtagttgtcg taatattacg tgtgacaatt ggttcacctc      1380
aatccctttg gcaaaaaact tactacaaga accgtataag ttaaccattg tgggaaccgt      1440
ggcatcaaac aaacgcgaga taccggaagt actgaaaaac agtcgctcca ggccagtggg      1500
aacatcgatg ttttgttttg acggacccct tactctcgtc tcatataaac cgaagccagc      1560
taagatggta tacttattat catcttgtga tgaggatgct tctatcaacg aaagtaccgg      1620
taaaccgcaa atggttatgt attataatca aactaaaggc ggagtggaca cgctagacca      1680
aatgagttct gtgatgacct gcagtaggaa gacgaatagg tggcctatgg cattattgta      1740
cggaatgata aacattgcct gcataaattc tttttattata tacagccata atgtcagtag      1800
caagggagaa aaggttcaaa gtcgcaaaaa atttatgaga aacctttaca tgagcctgac      1860
gtcatcgttt atgcgtaagc gtttagaagc tcctactttg aagagatatt tgcgcgataa      1920
tatctctaat attttgccaa atgaagtgcc tggtacatca gatgacagta ctgaagagcc      1980
agtaacgaaa aaacgtactt actgtactta ctgcccctct aaaataaggc gaaaggcaag      2040
tgcatcgtgc aaaaaatgca aaaagttat tgtcgagag cataatattg atatgtgcca       2100
aagttgtttc tgactgacta ataagtataa tttgtttcta ttatgtataa gttaagctaa      2160
ttacttattt tataatacaa catgactgtt tttaaagtac aaaataagtt tattttgta      2220
aaagagagaa tgtttaaaag ttttgttact ttatagaaga aattttgagt ttttgttttt      2280
ttttaataaa taaataaaca taaataaata gtttgttgaa tttattatta gtatgtaagt      2340
gtaaatataa taaaacttaa tatctattca aattaataaa taaacctcga tatacagacc      2400
gataaaacac atgcgtcaat tttacgcatg attatcttta acgtacgtca caatatgatt      2460
atctttctag gg                                                          2472

<210> SEQ ID NO 51
<211> LENGTH: 2472
<212> TYPE: DNA
<213> ORGANISM: Trichoplusia ni

<400> SEQUENCE: 51
ccctagaaag atagtctgcg taaaattgac gcatgcattc ttgaaatatt gctctctctt        60
tctaaatagc gcgaatccgt cgctgtgcgt ttaggacatc tcagtcgccg cttggagctc      120
ccgtgaggcg tgcttgtcaa tgcggtaagt gtcactgatt ttgaactata acgaccgcgt      180
gagtcaaaat gacgcatgat tatcttttac gtgactttta agatttaact catacgataa      240
ttatattgtt atttcatgtt ctacttacgt gataacttat tatatatata tttctcttgtt     300
atagatatcg tgactaatat ataataaaat gggtagttct ttagacgatg agcatatcct      360
ctctgctctt ctgcaaagcg atgacgagct tgttggtgag gattctgaca gtgaaatatc      420
agatcacgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa atcttgacc ttgccacaga ggactattag       600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat tttttactga tgagataatt tcggaaattg taaaatggac      780
aaatgctgag atatcattga aacgtcggga atctatgaca ggtgctacat tcgtgacac       840
gaatgaagat gaaatctatg ctttctttgg tattctggta atgacagcag tgagaaaaga      900
```

```
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa cgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtgctta ctgcccctct aaaataaggc gaaaggcaaa   2040
tgcatcgtgc aaaaaatgca aaaagttat tgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 52
<211> LENGTH: 2472
<212> TYPE: DNA
<213> ORGANISM: Trichoplusia ni

<400> SEQUENCE: 52

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttac gtgacttta agatttaact catacgataa    240
ttatattgtt atttcatgtt ctacttacgt gataacttat tatatatata tttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
```

```
acatgaagtg cagccaacgt caagcggtag tgaaatatta gacgaacaaa atgttattga      540
acaaccaggt tcttcattgg cttctaacaa aatcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat ttttactga tgagataatt tcggaaattg taaaatggac       780
aaatgctgag atatcattga aacgtcggga atctatgaca ggtgctacat tcgtgacac       840 gaatgaagat gaaatctatg cttcttggg tattctggta atgacagcag tgagaaaaga       900
taaccacatg tccacagatg acctctttga tcgatctttg tcaatggtgt acgtctctgt      960
aatgagtcgt gatcgttttg atttttttgat acgatgtctt agaatggatg acaaaagtat    1020
acggcccaca cttcgagaaa acgatgtatt tactcctgtt agaaaaatat gggatctctt     1080
tatccatcag tgcatacaaa attacactcc aggggctcat ttgaccatag atgaacagtt     1140
acttggtttt agaggacggt gtccgtttag gatgtatatc ccaaacaagc caagtaagta     1200
tggaataaaa atcctcatga tgtgtgacag tggtacaaag tatatgataa atggaatgcc     1260
ttatttggga agaggaacac agaccaacgg agtaccactc ggtgaatact acgtgaagga     1320
gttatcaaag cctgtgcacg gtagttgtcg taatattacg tgtgacaatt ggttcacctc     1380
aatccctttg gcaaaaaact tactacaaga accgtataag ttaaccattg tgggaaccgt     1440
ggcatcaaac aaacgcgaga taccggaagt actgaaaaac agtcgctcca ggccagtggg    1500
aacatcgatg ttttgttttg acggaccct tactctcgtc tcatataaac cgaagccagc     1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat atttttgccaa atgaagtgcc tggtacatca gatgacagta ctgaagagcc    1980
agtaacgaaa aaacgtactt actgtactta ctgcccctct aaaataaggc gaaaggcaaa    2040
ggcatcgtgc aaaaaatgca aaaagttat tgtcgagag cataatattg atatgtgcca      2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                         2472
```

<210> SEQ ID NO 53
<211> LENGTH: 2472
<212> TYPE: DNA
<213> ORGANISM: Trichoplusia ni

<400> SEQUENCE: 53

```
ccctagaaag atagtctgcg taaaattgac gcatgcattc ttgaaatatt gctctctctt       60
tctaaatagc gcgaatccgt cgctgtgcgt ttaggacatc tcagtcgccg cttggagctc      120
```

```
ccgtgaggcg tgcttgtcaa tgcggtaagt gtcactgatt ttgaactata acgaccgcgt      180
gagtcaaaat gacgcatgat tatcttttac gtgactttta agatttaact catacgataa      240
ttatattgtt atttcatgtt ctacttacgt gataacttat tatatatata ttttcttgtt      300
atagatatcg tgactaatat ataataaaat gggtagttct ttagacgatg agcatatcct      360
ctctgctctt ctgcaaagcg atgacgagct tgttggtgag gattctgaca gtgaaatatc      420
agatcacgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa aatcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat tttttactga tgagataatt tcggaaattg taaaatggac      780 aaaatgctgag atatcattga aacgtcggga atctatgaca ggtgctacat ttcgtgacac      840
gaatgaagat gaaatctatg ctttctttgg tattctggta atgacagcag tgagaaaaga      900
taaccacatg tccacagatg acctctttga tcgatctttg tcaatggtgt acgtctctgt      960
aatgagtcgt gatcgttttg attttttgat acgatgtctt agaatggatg acaaaagtat     1020
acggcccaca cttcgagaaa acgatgtatt tactcctgtt agaaaaatat gggatctctt     1080
tatccatcag tgcatacaaa attacactcc aggggctcat ttgaccatag atgaacagtt     1140
acttggtttt agaggacggt gtccgtttag gatgtatatc ccaaacaagc caagtaagta     1200
tggaataaaa atcctcatga tgtgtgacag tggtacaaag tatatgataa atggaatgcc     1260
ttatttggga agaggaacac agaccaacgg agtaccactc ggtgaatact acgtgaagga     1320
gttatcaaag cctgtgcacg gtagttgtcg taatattacg tgtgacaatt ggttcacctc     1380
aatccctttg gcaaaaaact tactacaaga accgtataag ttaaccattg tgggaaccgt     1440
ggcatcaaac aaacgcgaga taccggaagt actgaaaaac agtcgctcca ggccagtggg     1500
aacatcgatg ttttgttttg acggacccct tactctcgtc tcatataaac cgaagccagc     1560
taagatggta tacttattat catcttgtga tgaggatgct tctatcaacg aaagtaccgg     1620
taaaccgcaa atggttatgt attataatca aactaaaggc ggagtggaca cgctagacca     1680
aatgtgttct gtgatgacct gcagtaggaa gacgaatagg tggcctatgg cattattgta     1740
cggaatgata aacattgcct gcataaaattc ttttattata tacagccata atgtcagtag     1800
caagggagaa aaggttcaaa gtcgcaaaaa atttatgaga aacctttaca tgagcctgac     1860
gtcatcgttt atgcgtaagc gtttagaagc tcctactttg aagagatatt tgcgcgataa     1920
tatctctaat atttttgccaa atgaagtgcc tggtacatca gatgacagta ctgaagagcc     1980
agtaacgaaa aaacgtactt actgtactta ctgcccctct aaaataaggc gaaaggcaaa     2040
tgcagcgtgc aaaaaatgca aaaaagttat ttgtcgagag cataatattg atatgtgcca     2100
aagttgtttc tgactgacta ataagtataa tttgtttcta ttatgtataa gttaagctaa     2160
ttacttattt tataatacaa catgactgtt tttaaagtac aaaataagtt tatttttgta     2220
aaagagagaa tgtttaaaag ttttgttact ttatagaaga aattttgagt ttttgttttt     2280
ttttaataaa taaatataca taaataaata gtttgttgaa tttattatta gtatgtaagt     2340
gtaaatataa taaaacttaa tatctattca aattaataaa taaacctcga tatacagacc     2400
gataaaacac atgcgtcaat tttacgcatg attatcttta acgtacgtca caatatgatt     2460
```

-continued

| | |
|---|---|
| atctttctag gg | 2472 |

<210> SEQ ID NO 54
<211> LENGTH: 2472
<212> TYPE: DNA
<213> ORGANISM: Trichoplusia ni

<400> SEQUENCE: 54

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttac gtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat tttttactga tgagataatt tcggaaattg taaaatggac | 780 |
| aaaatgctgag atatcattga aacgtcggga atctatgaca ggtgctacat tcgtgacac | 840 |
| gaatgaagat gaaatctatg cttctcttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg attttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatccctttg gcaaaaaact tactacaaga accgtataag ttaaccattg tgggaaccgt | 1440 |
| ggcatcaaac aaacgcgaga taccggaagt actgaaaaac agtcgctcca ggccagtggg | 1500 |
| aacatcgatg ttttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata acattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat atttttgccaa atgaagtgcc tggtacatca gatgcacagta ctgaagagcc | 1980 |
| agtaacgaaa aaacgtactt actgtactta ctgccccctct aaaataaggc gaaaggcaaa | 2040 |
| tgcatcgtgc aaaaaatgca aaaaagttat ttgtcgagag cataatattg atatgtgcca | 2100 |

```
aagttgtttc tgactgacta ataagtataa tttgtttcta ttatgtataa gttaagctaa   2160
ttacttattt tataatacaa catgactgtt tttaaagtac aaaataagtt tattttttgta  2220 aaagagagaa tgtttaaaag ttttgttact ttatagaaga aattttgagt ttttgttttt   2280
ttttaataaa taaataaaca taaataaaata gtttgttgaa tttattatta gtatgtaagt  2340
gtaaatataa taaaacttaa tatctattca aattaataaa taaacctcga tatacagacc  2400
gataaaacac atgcgtcaat tttacgcatg attatcttta acgtacgtca caatatgatt  2460
atctttctag gg                                                      2472
```

<210> SEQ ID NO 55
<211> LENGTH: 2472
<212> TYPE: DNA
<213> ORGANISM: Trichoplusia ni

<400> SEQUENCE: 55

```
ccctagaaag atagtctgcg taaaattgac gcatgcattc ttgaaatatt gctctctctt    60
tctaaatagc gcgaatccgt cgctgtgcgt ttaggacatc tcagtcgccg cttggagctc   120
ccgtgaggcg tgcttgtcaa tgcggtaagt gtcactgatt ttgaactata acgaccgcgt   180
gagtcaaaat gacgcatgat tatctttac gtgacttta agatttaact catacgataa     240
ttatattgtt atttcatgtt ctacttacgt gataacttat tatatatata ttttcttgtt   300
atagatatcg tgactaatat ataataaaat gggtagttct ttagacgatg agcatatcct   360
ctctgctctt ctgcaaagcg atgacgagct tgttggtgag gattctgaca gtgaaatatc   420
agatcacgta agtgaagatg acgtccagag cgatacagaa gaagcgttta tagatgaggt   480
acatgaagtg cagccaacgt caagcggtag tgaaatatta gacgaacaaa atgttattga   540
acaaccaggt tcttcattgg cttctaacaa aatcttgacc ttgccacaga ggactattag   600
aggtaagaat aaacattgtt ggtcaacttc aaagtccacg aggcgtagcc gagtctctgc   660
actgaatcat gtcagatctc aaagaggtcc gacgcgtatg tgccgcaata tatatgaccc   720 actttatgc ttcaaaactat ttttactga tgagataatt tcggaaattg taaaatggac    780
aaatgctgag atatcattga aacgtcggga atctatgaca ggtgctacat ttcgtgacac   840
gaatgaagat gaaatctatg cttttctttgg tattctggta atgacagcag tgagaaaaga   900
taaccacatg tccacagatg acctctttga tcgatctttg tcaatggtgt acgtctctgt    960
aatgagtcgt gatcgttttg attttttgat acgatgtctt agaatggatg acaaaagtat  1020
acggcccaca cttcgagaaa acgatgtatt tactcctgtt agaaaaatat gggatctctt  1080
tatccatcag tgcatacaaa attacactcc aggggctcat ttgaccatag atgaacagtt  1140
acttggtttt agaggacggt gtccgtttag gatgtatatc ccaaacaagc caagtaagta  1200
tggaataaaa atcctcatga tgtgtgacag tggtacaaag tatatgataa atggaatgcc  1260
ttatttggga agaggaacac agaccaacgg agtaccactc ggtgaatact acgtgaagga  1320
gttatcaaag cctgtgcacg gtagttgtcg taatattacg tgtgacaatt ggttcacctc  1380
aatccctttg gcaaaaaact tactacaaga accgtataag ttaaccattg tgggaaccgt  1440
ggcatcaaac aaacgcgaga taccggaagt actgaaaaac agtcgctcca ggccagtggg  1500
aacatcgatg ttttgttttg acggacccct tactctcgtc tcatataaac cgaagccagc  1560
taagatggta tacttattat catcttgtga tgaggatgct tctatcaacg aaagtaccgg  1620
taaaccgcaa atggttatgt attataatca aactaaaggc ggagtggaca cgctagacca  1680
```

| | |
|---|---|
| aatgtgttct gtgatgacct gcagtaggaa gacgaatagg tggcctatgg cattattgta | 1740 |
| cggaatgata aacattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat attttgccaa atgaagtgcc tggtacatca gatgacagta ctgaagagcc | 1980 |
| agtaacgaaa aaacgtactt actgtactta ctgcccctct aaaataaggc gaaaggcaaa | 2040 |
| tgcatcgtgc aaaaaatgca aaaaagttat tgtcgagag cataatattg atgtgtgcca | 2100 |
| aagttgtttc tgactgacta ataagtataa ttttgtttcta ttatgtataa gttaagctaa | 2160 |
| ttacttattt tataatacaa catgactgtt tttaaagtac aaaataagtt tattttttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 56
<211> LENGTH: 2472
<212> TYPE: DNA
<213> ORGANISM: Trichoplusia ni

<400> SEQUENCE: 56

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttta cgtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttactga tgagataatt tcggaaattg taaaatggac | 780 |
| aaatgctgag atatcattga aacgtcggga atctatgaca ggtgctacat tcgtgatac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg atttttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc agggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |

-continued

```
gttatcaaag cctgtgcacg gtagttgtcg taatattacg tgtgacaatt ggttcacctc      1380
aatccctttg gcaaaaaact tactacaaga accgtataag ttaaccattg tgggaaccgt      1440
ggcatcaaac aaacgcgaga taccggaagt actgaaaaac agtcgctcca ggccagtggg      1500
aacatcgatg ttttgttttg acggacccct tactctcgtc tcatataaac cgaagccagc      1560
taagatggta tacttattat catcttgtga tgaggatgct tctatcaacg aaagtaccgg      1620
taaaccgcaa atggttatgt attataatca aactaaaggc ggagtggaca cgctagacca      1680
aatgtgttct gtgatgacct gcagtaggaa gacgaatagg tggcctatgg cattattgta      1740
cggaatgata acattgcct gcataaattc ttttattata tacagccata atgtcagtag      1800
caagggagaa aaggttcaaa gtcgcaaaaa atttatgaga aaccttttaca tgagcctgac      1860 gtcatcgttt atgcgtaagc gtttagaagc tcctactttg aagagatatt tgcgcgataa      1920
tatctctaat atttttgccaa atgaagtgcc tggtacatca gatgacagta ctgaagagcc      1980
agtaacgaaa aaacgtactt actgtactta ctgcccctct aaaataaggc gaaaggcaaa      2040
tgcatcgtgc aaaaaatgca aaaaagttat tgtcgagag cataatattg atgtgtgcca      2100
aagttgtttc tgactgacta ataagtataa tttgtttcta ttatgtataa gttaagctaa      2160
ttacttattt tataatacaa catgactgtt tttaaagtac aaaataagtt tattttgta      2220 aaagagagaa tgtttaaaag ttttgttact ttatagaaga aattttgagt ttttgttttt      2280
ttttaataaa taaataaaca taaataaata gtttgttgaa tttattatta gtatgtaagt      2340
gtaaatataa taaacttaa tatctattca aattaataaa taaacctcga tatacagacc      2400
gataaaacac atgcgtcaat tttacgcatg attatctta acgtacgtca caatatgatt      2460
atctttctag gg                                                          2472
```

<210> SEQ ID NO 57
<211> LENGTH: 2472
<212> TYPE: DNA
<213> ORGANISM: Trichoplusia ni

<400> SEQUENCE: 57

```
ccctagaaag atagtctgcg taaaattgac gcatgcattc ttgaaatatt gctctctctt       60
tctaaatagc gcgaatccgt cgctgtgcgt ttaggacatc tcagtcgccg cttggagctc      120
ccgtgaggcg tgcttgtcaa tgcggtaagt gtcactgatt ttgaactata acgaccgcgt      180
gagtcaaaat gacgcatgat tatcttttac gtgacttttta agatttaact catacgataa      240
ttatattgtt atttcatgtt ctacttacgt gataacttat tatatatata ttttcttgtt      300
atagatatcg tgactaatat ataataaaat gggtagttct ttagacgatg agcatatcct      360
ctctgctctt ctgcaaagcg atgacagct tgttggtgag gattctgaca gtgaaatatc      420
agatcacgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa aatcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat ttttactga tgagataatt tcggaaattg taaaatggac      780
aaatgctgag atatcattga aacgtcggga atctatgaca ggtgctacat tcgtgcacac      840
gaatgaagat gaaatctatg ctttctttgg tattctggta atgacagcag tgagaaaaga      900
```

```
taaccacatg tccacagatg acctctttga tcgatctttg tcaatggtgt acgtctctgt      960
aatgagtcgt gatcgttttg atttttttgat acgatgtctt agaatggatg acaaaagtat   1020
acggcccaca cttcgagaaa acgatgtatt tactcctgtt agaaaaatat gggatctctt     1080
tatccatcag tgcatacaaa attacactcc aggggctcat ttgaccatag atgaacagtt    1140
acttggtttt agaggacggt gtccgtttag gatgtatatc ccaaacaagc caagtaagta     1200
tggaataaaa atcctcatga tgtgtgacag tggtacaaag tatatgataa atggaatgcc    1260
ttatttggga agaggaacac agaccaacgg agtaccactc ggtgaatact acgtgaagga   1320
gttatcaaag cctgtgcacg gtagttgtcg taatattacg tgtgacaatt ggttcacctc     1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg  1500
aacatcgatg ttttgttttg acggacccct tactctcgtc tcatataaac cgaagccagc    1560
taagatggta tacttattat catcttgtga tgaggatgct tctatcaacg aaagtaccgg  1620
taaaccgcaa atggttatgt attataatca aactaaaggc ggagtggaca cgctagacca  1680
aatgtgttct gtgatgacct gcagtaggaa gacgaatagg tggcctatgg cattattgta    1740
cggaatgata aacattgcct gcataaaattc ttttattata tacagccata atgtcagtag  1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa  2040
tgcatcgtgc aaaaaatgca aaaaagttat ttgtcgagag cataatattg atatgtgcca   2100
aggttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc   2400
gataaaacac atgcgtcaat tttacgcatg attatcttta acgtacgtca caatatgatt    2460
atctttctag gg                                                          2472
```

<210> SEQ ID NO 58
<211> LENGTH: 2472
<212> TYPE: DNA
<213> ORGANISM: Trichoplusia ni

<400> SEQUENCE: 58

```
ccctagaaag atagtctgcg taaaattgac gcatgcattc ttgaaatatt gctctctctt       60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt    180
gagtcaaaat gacgcatgat tatcttttac gtgacttttta agatttaact catacgataa    240
ttatattgtt atttcatgtt ctacttacgt gataacttat tatatatata ttttcttgtt      300
atagatatcg tgactaatat ataataaaat gggtagttct ttagacgatg agcatatcct     360
ctctgctctt ctgcaaagcg atgacgagct tgttggtgag gattctgaca gtgaaatatc   420
agatcacgta agtgaagatg acgtccgag cgatacagaa gaagcgttta tagatgaggt   480
acatgaagtg cagccaacgt caagcggtag tgaaatatta gacgaacaaa atgttattga    540
```

```
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat ttttttactga tgagataatt tcggaaattg taaaatggac    780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacatg tccacagatg aacctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat ttgtcgagag cataatattg atatgtgcca   2100
aagttgttta tgactgacta ataagtataa tttgtttcta ttatgtataa gttaagctaa   2160
ttacttattt tataatacaa catgactgtt tttaaagtac aaaataagtt tattttttgta   2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 59
<211> LENGTH: 2472
<212> TYPE: DNA
<213> ORGANISM: Trichoplusia ni

<400> SEQUENCE: 59

```
ccctagaaag atagtctgcg taaaattgac gcatgcattc ttgaaatatt gctctctctt    60
tctaaatagc gcgaatccgt cgctgtgcgt ttaggacatc tcagtcgccg cttggagctc   120
```

```
ccgtgaggcg tgcttgtcaa tgcggtaagt gtcactgatt ttgaactata acgaccgcgt    180
gagtcaaaat gacgcatgat tatcttttac gtgacttttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat ttttttactga tgagataatt tcggaaattg taaaatggac    780
aaatgctgag atatcattga aacgtcggga atctatgaca ggtgctacat ttcgtgacac    840
gaatgaagat gaaatctatg cttctcttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140 acttggttttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
ggcatcaaac aaacgcgaga taccggaagt actgaaaaac agtcgctcca ggccagtggg   1500
aacatcgatg ttttgttttg acggaccccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat ttgtcgagag cataatattg atatgtgcca   2100
aagttgtttc tggctgacta ataagtataa tttgtttcta ttatgtataa gttaagctaa   2160
ttacttattt tataatacaa catgactgtt tttaaagtac aaaataagtt tattttttgta   2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                        2472
```

<210> SEQ ID NO 60
<211> LENGTH: 2472
<212> TYPE: DNA
<213> ORGANISM: Trichoplusia ni

<400> SEQUENCE: 60

| | | | | | |
|---|---|---|---|---|---|
| ccctagaaag | atagtctgcg | taaaattgac | gcatgcattc | ttgaaatatt | gctctctctt | 60 |
| tctaaatagc | gcgaatccgt | cgctgtgcgt | ttaggacatc | tcagtcgccg | cttggagctc | 120 |
| ccgtgaggcg | tgcttgtcaa | tgcggtaagt | gtcactgatt | ttgaactata | acgaccgcgt | 180 |
| gagtcaaaat | gacgcatgat | tatcttttac | gtgactttta | agatttaact | catacgataa | 240 |
| ttatattgtt | atttcatgtt | ctacttacgt | gataacttat | tatatatata | ttttcttgtt | 300 |
| atagatatcg | tgactaatat | ataataaaat | gggtagttct | ttagacgatg | agcatatcct | 360 |
| ctctgctctt | ctgcaaagcg | atgacgagct | tgttggtgag | gattctgaca | gtgaaatatc | 420 |
| agatcatgta | agtgaagatg | acgtccagag | cgatacagaa | gaagcgttta | tagatgaggt | 480 |
| acatgaagtg | cagccaacgt | caagcggtag | tgaaatatta | gacgaacaaa | atgttattga | 540 |
| acaaccaggt | tcttcattgg | cttctaacaa | aatcttgacc | ttgccacaga | ggactattag | 600 |
| aggtaagaat | aaacattgtt | ggtcaacttc | aaagtccacg | aggcgtagcc | gagtctctgc | 660 |
| actgaatcat | gtcagatctc | aaagaggtcc | gacgcgtatg | tgccgcaata | tatatgaccc | 720 |
| acttttatgc | ttcaaactat | tttttactga | tgagataatt | tcggaaattg | taaaatggac | 780 |
| aaaatgctgag | atatcattga | aacgtcggga | atctatgaca | ggtgctacat | tcgtgacac | 840 |
| gaatgaagat | gaaatctatg | ctttctttgg | tattctggta | atgacagcag | tgagaaaaga | 900 |
| taaccacatg | tccacagatg | acctctttga | tcgatctttg | tcaatggtgt | acgtctctgt | 960 |
| aatgagtcgt | gatcgttttg | attttttgat | acgatgtctt | agaatggatg | acaaaagtat | 1020 |
| acggcccaca | cttcgagaaa | acgatgtatt | tactcctgtt | agaaaaatat | gggatctctt | 1080 |
| tatccatcag | tgcatacaaa | attacactcc | aggggctcat | tgaccatag | atgaacagtt | 1140 |
| acttggtttt | agaggacggt | gtccgtttag | gatgtatatc | ccaaacaagc | caagtaagta | 1200 |
| tggaataaaa | atcctcatga | tgtgtgacag | tggtacaaag | tatatgataa | atggaatgcc | 1260 |
| ttatttggga | agaggaacac | agaccaacgg | agtaccactc | ggtgaatact | acgtgaagga | 1320 |
| gttatcaaag | cctgtgcacg | gtagttgtcg | taatattacg | tgtgacaatt | ggttcacctc | 1380 |
| aatcccttg | gcaaaaaact | tactacaaga | accgtataag | ttaaccattg | tgggaaccgt | 1440 |
| ggcatcaaac | aaacgcgaga | taccggaagt | actgaaaaac | agtcgctcca | ggccagtggg | 1500 |
| aacatcgatg | ttttgttttg | acggaccccct | tactctcgtc | tcatataaac | cgaagccagc | 1560 |
| taagatggta | tacttattat | catcttgtga | tgaggatgct | tctatcaacg | aaagtaccgg | 1620 |
| taaaccgcaa | atggttatgt | attataatca | aactaaaggc | ggagtggaca | cgctagacca | 1680 |
| aatgtgttct | gtgatgacct | gcagtaggaa | gacgaatagg | tggcctatgg | cattattgta | 1740 |
| cggaatgata | aacattgcct | gcataaattc | ttttattata | tacagccata | atgtcagtag | 1800 |
| caagggagaa | aaggttcaaa | gtcgcaaaaa | atttatgaga | aacctttaca | tgagcctgac | 1860 |
| gtcatcgttt | atgcgtaagc | gtttagaagc | tcctactttg | aagagatatt | tgcgcgataa | 1920 |
| tatctctaat | attttgccaa | atgaagtgcc | tggtacatca | gatgacagta | ctgaagagcc | 1980 |
| agtaacgaaa | aaacgtactt | actgtactta | ctgccctct | aaaataaggc | gaaaggcaaa | 2040 |
| tgcatcgtgc | aaaaaatgca | aaaagttat | ttgtcgagag | cataatattg | atatgtgcca | 2100 |

-continued

```
aagttgtttc ggactgacta ataagtataa tttgtttcta ttatgtataa gttaagctaa    2160
ttacttattt tataatacaa catgactgtt tttaaagtac aaaataagtt tattttttgta   2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                       2472
```

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64
<211> LENGTH: 594
<212> TYPE: PRT
<213> ORGANISM: Trichoplusia ni

<400> SEQUENCE: 64

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190
```

```
His Met Ser Thr Asp Asp Leu Phe Asp Arg Ser Leu Ser Met Val Tyr
            195                 200                 205
Val Ser Val Met Ser Arg Asp Arg Phe Asp Phe Leu Ile Arg Cys Leu
210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Thr Lys
    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Asn
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
    530                 535                 540
Asp Asp Ser Thr Glu Glu Pro Val Met Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe

<210> SEQ ID NO 65
```

```
<211> LENGTH: 594
<212> TYPE: PRT
<213> ORGANISM: Trichoplusia ni

<400> SEQUENCE: 65

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
370                 375                 380

Ser Arg Ser Arg Pro Val Gly Thr Ser Met Phe Cys Phe Asp Gly Pro
```

```
                385                 390                 395                 400
Leu Thr Leu Val Ser Tyr Lys Pro Lys Pro Ala Lys Met Val Tyr Leu
                    405                 410                 415
Leu Ser Ser Cys Asp Glu Asp Ala Ser Ile Asn Glu Ser Thr Gly Lys
                420                 425                 430
Pro Gln Met Val Met Tyr Tyr Asn Gln Thr Lys Gly Gly Val Asp Thr
                435                 440                 445
Leu Asp Gln Met Cys Ser Val Met Thr Cys Ser Arg Lys Thr Asn Arg
            450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                    485                 490                 495
Gln Ser Arg Lys Lys Phe Met Arg Asn Leu Tyr Met Ser Leu Thr Ser
                500                 505                 510
Ser Phe Met Arg Lys Arg Leu Glu Ala Pro Thr Leu Lys Arg Tyr Leu
                515                 520                 525
Arg Asp Asn Ile Ser Asn Ile Leu Pro Asn Glu Val Pro Gly Thr Ser
            530                 535                 540
Asp Asp Ser Thr Glu Glu Pro Val Met Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe

<210> SEQ ID NO 66
<211> LENGTH: 594
<212> TYPE: PRT
<213> ORGANISM: Trichoplusia ni

<400> SEQUENCE: 66

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
                20                  25                  30
His Val Ser Glu Asp Asp Val Gln Ser Asp Thr Glu Glu Ala Phe Ile
            35                  40                  45
Asp Glu Val His Glu Val Gln Pro Thr Ser Ser Gly Ser Glu Ile Leu
        50                  55                  60
Asp Glu Gln Asn Val Ile Glu Gln Pro Gly Ser Ser Leu Ala Ser Asn
65                  70                  75                  80
Arg Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
                100                 105                 110
Asn Ile Val Arg Ser Gln Arg Gly Pro Thr Arg Met Cys Arg Asn Ile
            115                 120                 125
Tyr Asp Pro Leu Leu Cys Phe Lys Leu Phe Phe Thr Asp Glu Ile Ile
        130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
```

```
            165                 170                 175
Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Ala Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Arg Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590
```

Cys Phe

<210> SEQ ID NO 67
<211> LENGTH: 2472
<212> TYPE: DNA
<213> ORGANISM: Trichoplusia ni

<400> SEQUENCE: 67

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata cgaccgcgt      180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat ttcgtgacac     840
gaatgaagat gaaatctatg ctttctttgg tattctggta atgacagcag tgagaaaaga     900
taaccacatg tccacagatg acctctttga tcgatctttg tcaatggtgt acgtctctgt     960
aatgagtcgt gatcgttttg atttttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
ggcatcaaac aaacgcgaga taccggaagt actgaaaaac agtcgctcca ggccagtggg    1500
aacatcgatg ttttgtttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
```

```
tgcatcgtgc aaaaaatgca aaaaagttat tgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaacttaa tatctattca aattaataaa taaacctcga tatacagacc    2400
gataaaacac atgcgtcaat tttacgcatg attatcttta acgtacgtca caatatgatt    2460
atctttctag gg                                                         2472

<210> SEQ ID NO 68
<211> LENGTH: 2472
<212> TYPE: DNA
<213> ORGANISM: Trichoplusia ni

<400> SEQUENCE: 68
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgacttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtc cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat ttttactga tgagataatt tcggaaattg taaaatggac    780
aaatgctgag atatcattga acgtcggga atctatgaca ggtgctacat ttcgtgacac    840
gaatgaagat gaaatctatg cttctcttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact actacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggaccct tactctcgtc tcatataaac cgaagccagc   1560
taagatggta tacttattat catccttgtga tgaggatgct tctatcaacg aaagtaccgg   1620
taaaccgcaa atggttatgt attataatca aactaaaggc ggagtggaca cgctagacca   1680
```

```
aatgtgttct gtgatgacct gcagtaggaa gacgaatagg tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttttgta   2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472

<210> SEQ ID NO 69
<211> LENGTH: 2472
<212> TYPE: DNA
<213> ORGANISM: Trichoplusia ni

<400> SEQUENCE: 69
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat ttcgtgacac     840
gaatgaagat gaaatctatg ctttctttgg tattctggta atgacagcag tgagaaaaga     900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaatat gggatctctt    1080 tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
```

-continued

```
ttatttggga agaggaacac agaccaacgg agtaccactc ggtgaatact acgtgaagga      1320
gttatcaaag cctgtgcacg gtagttgtcg taatattacg tgtgacaatt ggttcacctc      1380
aatccctttg gcaaaaaact tactacaaga accgtataag ttaaccattg tgggaaccgt      1440
ggcatcaaac gcacgcgaga taccggaagt actgaaaaac agtcgctcca ggccagtggg      1500
aacatcgatg ttttgttttg acggacccct tactctcgtc tcatataaac cgaagccagc      1560
taagatggta tacttattat catcttgtga tgaggatgct tctatcaacg aaagtaccgg      1620
taaaccgcaa atggttatgt attataatca aactaaaggc ggagtggaca cgctagacca      1680
aatgtgttct gtgatgacct gcagtaggaa gacgaatagg tggcctatgg cattattgta      1740
cggaatgata acattgcct gcataaattc ttttattata tacagccata atgtcagtag      1800
caagggagaa aaggttcaaa gtcgcaaaaa atttatgaga aacctttaca tgagcctgac      1860
gtcatcgttt atgcgtaagc gtttagaagc tcctactttg aagagatatt tgcgcgataa      1920
tatctctaat atttttgccaa atgaagtgcc tggtacatca gatgacagta ctgaagagcc      1980
agtaacgaaa aaacgtactt actgtactta ctgcccctct aaaataaggc gaaaggcaaa      2040
tgcatcgtgc aaaaaatgca aaaaagttat tgtcgagag cataatattg atatgtgcca      2100
aagttgtttc tgactgacta ataagtataa tttgtttcta ttatgtataa gttaagctaa      2160
ttacttattt tataatacaa catgactgtt tttaaagtac aaaataagtt tattttgta      2220 aaagagagaa tgtttaaaag ttttgttact ttatagaaga aattttgagt ttttgttttt      2280
ttttaataaa taaataaaca taaataaata gtttgttgaa tttattatta gtatgtaagt      2340
gtaaatataa taaaacttaa tatctattca aattaataaa taaacctcga tatacagacc      2400
gataaaacac atgcgtcaat tttacgcatg attatcttta acgtacgtca caatatgatt      2460
atctttctag gg                                                         2472
```

<210> SEQ ID NO 70
<211> LENGTH: 2472
<212> TYPE: DNA
<213> ORGANISM: Trichoplusia ni

<400> SEQUENCE: 70

```
ccctagaaag atagtctgcg taaaattgac gcatgcattc ttgaaatatt gctctctctt       60
tctaaatagc gcgaatccgt cgctgtgcgt ttaggacatc tcagtcgccg cttggagctc      120
ccgtgaggcg tgcttgtcaa tgcggtaagt gtcactgatt ttgaactata acgaccgcgt      180
gagtcaaaat gacgcatgat tatcttttac gtgactttta agatttaact catacgataa      240
ttatattgtt atttcatgtt ctacttacgt gataacttat tatatatata ttttcttgtt      300
atagatatcg tgactaatat ataataaaat gggtagttct ttagacgatg agcatatcct      360
ctctgctctt ccgcaaagcg atgacgagct tgttggtgag gattctgaca gtgaaatatc      420
agatcacgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa atcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat ttttactga tgagataatt tcggaaattg taaaatggac      780
aaatgctgag atatcattga aacgtcggga atctatgaca ggtgctacat tcgtgacac      840 gaatgaagat gaaatctatg ctttctttgg tattctggta atgacagcag tgagaaaaga      900
```

```
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aaccttaca tgagcctgac   1860
gtcatcgttt atgcgtaagc gtttagaagc tcctactttg aagagatatt tgcgcgataa   1920
tatctctaat atttttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat tgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 71
<211> LENGTH: 2472
<212> TYPE: DNA
<213> ORGANISM: Trichoplusia ni

<400> SEQUENCE: 71

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg ataacgagct tgttggtgag gattctgaca gtgaaatatc    420
agatcacgta agtgaagatg acgtccagag cgatacagaa gaagcgttta tagatgaggt    480
```

| | |
|---|---|
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttactga tgagataatt tcggaaattg taaaatggac | 780 |
| aaatgctgag atatcattga aacgtcggga atctatgaca ggtgctacat tcgtgacac | 840 |
| gaatgaagat gaaatctatg cttctttgg tattctggta atgacagcag tgagaaaga | 900 |
| taaccacatg tccacagatg acctctttga tcgatctttg tcaatggtgt acgtctctgt | 960 |
| aatgagtcgt gatcgttttg atttttgat acgatgtctt agaatggatg acaaaagtat | 1020 |
| acggcccaca cttcgagaaa acgatgtatt tactcctgtt agaaaatat gggatctctt | 1080 |
| tatccatcag tgcatacaaa attacactcc aggggctcat ttgaccatag atgaacagtt | 1140 |
| acttggttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatccctttg gcaaaaaact tactacaaga accgtataag ttaaccattg tgggaaccgt | 1440 |
| gcgatcaaac gcacgcgaga taccggaagt actgaaaaac agtcgctcca ggccagtggg | 1500 |
| aacatcgatg ctttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata aacattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat attttgccaa atgaagtgcc tggtacatca gatgacagta ctgaagagcc | 1980 |
| agtaacgaaa aaacgtactt actgtactta ctgcccctct aaaataaggc gaaaggcaaa | 2040 |
| tgcatcgtgc aaaaaatgca aaaaagttat tgtcgagag cataatattg atatgtgcca | 2100 |
| aagttgtttc tgactgacta ataagtataa tttgtttcta ttatgtataa gttaagctaa | 2160 |
| ttacttattt tataatacaa catgactgtt tttaaagtac aaaataagtt tattttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 72
<211> LENGTH: 2472
<212> TYPE: DNA
<213> ORGANISM: Trichoplusia ni

<400> SEQUENCE: 72

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |

```
ccgtgaggcg tgcttgtcaa tgcggtaagt gtcactgatt ttgaactata acgaccgcgt    180
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatacc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat ttttttactga tgagataatt tcggaaattg taaaatggac    780 aaaatgctgag atatcattga aacgtcggga atctatggca ggtgctacat ttcgtgacac    840
gaatgaagat gaaatctatg cttttctttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380 aatcccttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggaccccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaagttat tgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaacttaa tatctattca aattaataaa taaacctcga tatacagacc   2400
gataaaacac atgcgtcaat tttacgcatg attatcttta acgtacgtca caatatgatt   2460
```

| | |
|---|---|
| atctttctag gg | 2472 |

<210> SEQ ID NO 73
<211> LENGTH: 2472
<212> TYPE: DNA
<213> ORGANISM: Trichoplusia ni

<400> SEQUENCE: 73

| | |
|---|---:|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttttac gtgacttttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agattacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttttactga tgagataatt tcggaaattg taaaatggac | 780 |
| aaaatgctgag atatcattga aacgtcggga atctatgaca ggtgctacat ttcgtgacac | 840 |
| gaatgaagat gaaatctatg cttttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg atttttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatccctttg gcaaaaaact tactacaaga accgtataag ttaaccattg tgggaaccgt | 1440 |
| gcgatcaaac gcacgcgaga taccggaagt actgaaaaac agtcgctcca ggccagtggg | 1500 |
| aacatcgatg ttttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata acattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat atttttgccaa atgaagtgcc tggtacatca gatgcacagta ctgaagagcc | 1980 |
| agtaacgaaa aaacgtactt actgtactta ctgcccctct aaaataaggc gaaaggcaaa | 2040 |
| tgcatcgtgc aaaaaatgca aaaagttat ttgtcgagag cataatattg atatgtgcca | 2100 |

```
aagttgtttc tgactgacta ataagtataa tttgtttcta ttatgtataa gttaagctaa    2160
ttacttattt tataatacaa catgactgtt tttaaagtac aaaataagtt tattttttgta   2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 74
<211> LENGTH: 2472
<212> TYPE: DNA
<213> ORGANISM: Trichoplusia ni

<400> SEQUENCE: 74

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttttac gtgacttttta agatttaact catacgataa   240
ttatattgtt atttcatgtt ctacttacgt gataacttat tatatatata ttttcttgtt    300
atagatatcg tgactaatat ataataaaat gggtagttct ttagacgatg agcatatcct   360
ctctgctctt ctgcaaagcg atgacgagct tgttggtgag gattctgaca gtgaaatatc   420
agatcacgta agtgaagatg acgtccagag cgatacaaaa gaagcgttta tagatgaggt   480
acatgaagtg cagccaacgt caagcggtag tgaaatatta gacgaacaaa atgttattga   540
acaaccaggt tcttcattgg cttctaacaa atcttgacc ttgccacaga ggactattag    600
aggtaagaat aaacattgtt ggtcaacttc aaagtccacg aggcgtagcc gagtctctgc   660
actgaatcat gtcagatctc aaagaggtcc gacgcgtatg tgccgcaata tatatgaccc   720
acttttatgc ttcaaactat ttttactga tgagataatt tcggaaattg taaaatggac    780
aaatgctgag atatcattga aacgtcggga atctatgaca ggtgctacat tcgtgacac    840 gaatgaagat gaaatctatg cttttcttgg tattctggta atgacagcag tgagaaaaga   900
taaccacatg tccacagatg acctctttga tcgatctttg tcaatggtgt acgtctctgt   960
aatgagtcgt gatcgttttg atttttttgat acgatgtctt agaatggatg acaaaagtat  1020
acggcccaca cttcgagaaa acgatgtatt tactcctgtt agaaaatat gggatctctt    1080 tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaagg cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggaccccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
```

| | |
|---|---|
| aatgtgttct gtgatgacct gcagtaggaa gacgaatagg tggcctatgg cattattgta | 1740 |
| cggaatgata aacattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat attttgccaa atgaagtgcc tggtacatca gatgacagta ctgaagagcc | 1980 |
| agtaacgaaa aaacgtactt actgtactta ctgcccctct aaaataaggc gaaaggcaaa | 2040 |
| tgcatcgtgc aaaaaatgca aaaagttat tgtcgagag cataatattg atatgtgcca | 2100 |
| aagttgtttc tgactgacta ataagtataa ttttgtttcta ttatgtataa gttaagctaa | 2160 |
| ttacttattt tataatacaa catgactgtt tttaaagtac aaaataagtt tattttttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 75
<211> LENGTH: 2472
<212> TYPE: DNA
<213> ORGANISM: Trichoplusia ni

<400> SEQUENCE: 75

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatcttttac gtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa ggagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttactga tgagataatt tcggaaattg taaaatggac | 780 |
| aaatgctgag atatcattga acgtcggga atctatgaca ggtgctacat tcgtgacac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg atttttttgat acgatgtctt agaatggatg acaaaagtat | 1020 |
| acggccacca cttcgagaaa acgatgtatt tactcctgtt agaaaaatat gggatctctt | 1080 |
| tatccatcag tgcatacaaa attacactcc aggggctcat tgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |

```
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct  gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat tgtcgagag cataatattg atatgtgcca     2100
aagttgtttc tgactgacta ataagtataa tttgtttcta ttatgtataa gttaagctaa    2160
ttacttattt tataatacaa catgactgtt tttaaagtac aaaataagtt tattttgta     2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaacttaa  tatctattca aattaataaa taaacctcga tatacagacc    2400
gataaaacac atgcgtcaat tttacgcatg attatcttta acgtacgtca caatatgatt    2460
atctttctag gg                                                        2472
```

<210> SEQ ID NO 76
<211> LENGTH: 2472
<212> TYPE: DNA
<213> ORGANISM: Trichoplusia ni

<400> SEQUENCE: 76

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgacttta  agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacagct  tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacatcgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat ttttactga  tgagataatt tcggaaattg taaaatggac     780
aaatgctgag atatcattga aacgtcggga atctatgaca ggtgctacat tcgtgcacac     840
gaatgaagat gaaatctatg ctttctttgg tattctggta atgacagcag tgagaaaaga    900
```

| | |
|---|---|
| taaccacatg tccacagatg acctctttga tcgatctttg tcaatggtgt acgtctctgt | 960 |
| aatgagtcgt gatcgttttg atttttttgat acgatgtctt agaatggatg acaaaagtat | 1020 |
| acggcccaca cttcgagaaa acgatgtatt tattcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatcccttg gcaaaaaact tactacaaga accgtataag ttaaccattg tgggaaccgt | 1440 |
| gcgatcaaac gcacgcgaga taccggaagt actgaaaaac agtcgctcca ggccagtggg | 1500 |
| aacatcgatg ttttgttttg acggacccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata acattgcct gcataaaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat atttgccaa atgaagtgcc tggtacatca gatgacagta ctgaagagcc | 1980 |
| agtaacgaaa aaacgtactt actgtactta ctgccctct aaaataaggc gaaaggcaaa | 2040 |
| tgcatcgtgc aaaaaatgca aaaaagttat ttgtcgagag cataatattg atatgtgcca | 2100 |
| aagttgttc tgactgacta ataagtataa tttgtttcta ttatgtataa gttaagctaa | 2160 |
| ttacttattt tataatacaa catgactgtt tttaaagtac aaaataagtt tatttttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 77
<211> LENGTH: 2472
<212> TYPE: DNA
<213> ORGANISM: Trichoplusia ni

<400> SEQUENCE: 77

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttac gtgacttta agatttaact catacgataa | 240 |
| ttatattgtt atttcatgtt ctacttacgt gataacttat tatatatata tttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccgagag cgatacagaa gaagcgttta tagatgaggt | 480 |
| acatgaagtg cagccaacgt caagcggtag tgaaatatta gacgaacaaa atgttattga | 540 |

```
acaaccaggt tcttcattgg cttctaacaa atcttgacc ttgccacaga ggactattag    600
aggtaagaat aaacattgtt ggtcaacttc aaagcccacg aggcgtagcc gagtctctgc    660
actgaatcat gtcagatctc aaagaggtcc gacgcgtatg tgccgcaata tatatgaccc    720
acttttatgc ttcaaactat ttttactga tgagataatt tcggaaattg taaaatggac    780
aaatgctgag atatcattga aacgtcggga atctatgaca ggtgctacat tcgtgacac    840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaatat gggatctctt   1080 tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380 aatcccttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620 taaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc tttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat tgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttgta   2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                        2472

<210> SEQ ID NO 78
<211> LENGTH: 2472
<212> TYPE: DNA
<213> ORGANISM: Trichoplusia ni

<400> SEQUENCE: 78
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
```

```
ccgtgaggcg tgcttgtcaa tgcggtaagt gtcactgatt ttgaactata acgaccgcgt      180
gagtcaaaat gacgcatgat tatcttttac gtgacttttta agatttaact catacgataa    240
```

```
ccgtgaggcg tgcttgtcaa tgcggtaagt gtcactgatt ttgaactata acgaccgcgt      180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggccc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat ttcgtgacac     840
gaatgaagat gaaatctatg cttctcttgg tattctggta atgacagcag tgaaaaaaga     900
taaccacatg tccacagatg acctctttga tcgatctttg tcaatggtgt acgtctctgt     960
aatgagtcgt gatcgttttg atttttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg tttttgttttg acggaccccct tactctcgtc tcatataaac cgaagccagc   1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat atttttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat tgtcgagag cataatattg atatgtgcca    2100
aagttgtttc tgactgacta ataagtataa tttgtttcta ttatgtataa gttaagctaa    2160 ttacttatttt tataatacaa catgactgtt tttaaagtac aaaataagtt tattttgta    2220 aaagagagaa tgtttaaaag ttttgttact ttatagaaga aatttgagt ttttgttttt    2280 ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460 atcttttctag gg                                                         2472
```

<210> SEQ ID NO 79
<211> LENGTH: 2472
<212> TYPE: DNA
<213> ORGANISM: Trichoplusia ni

<400> SEQUENCE: 79

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatgtgaccc     720
acttttatgc ttcaaactat ttttactga tgagataatt tcggaaattg taaaatggac     780
aaatgctgag atatcattga aacgtcggga atctatgaca ggtgctacat tcgtgacac      840
gaatgaagat gaaatctatg cttctcttgg tattctggta atgacagcag tgaggaaaga     900
taaccacatg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa cgatgtatatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatcccttg gcaaaaaact actacaaga accgtataag ttaaccattg tgggaaccgt     1440
gcgatcaaac gcacgcgaga taccggaagt actgaaaaac agtcgctcca ggccagtggg    1500
aacatcgatg ttttgttttg acggaccct tactctcgtc tcatataaac cgaagccagc     1560
taagatggta tacttattat catcttgtga tgaggatgct tctatcaacg aaagtaccgg    1620
taaaccgcaa atggttatgt attataatca aactaaaggc ggagtggaca cgctaaacca    1680
aatgtgttct gtgatgacct gcagtaggaa gacgaatagg tggcctatgg cattattgta    1740
cggaatgata aacattgcct gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagaggtatt tgcgcgataa    1920
tatctctaat attttgccaa atgaagtgcc tggtacatca gatgacagta ctgaagagcc    1980
agtaacgaaa aaacgtactt actgtactta ctgccctct aaaataaggc gaaaggcaaa    2040
tgcatcgtgc aaaaaatgca aaaaagttat ttgtcgagag cataatattg atatgtgcca    2100
```

```
aagttgtttc tgactgacta ataagtataa tttgtttcta ttatgtataa gttaagctaa    2160
ttacttattt tataatacaa catgactgtt tttaaagtac aaaataagtt tattttttgta   2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472

<210> SEQ ID NO 80
<211> LENGTH: 2472
<212> TYPE: DNA
<213> ORGANISM: Trichoplusia ni

<400> SEQUENCE: 80
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat ttttactga tgagataatt tcggaaattg taaaatggac      780
aaatgctgag atatcattga aacgtcggga atctatgaca ggtgctacat tcgtgacac      840 gaatgaagat gaaatctatg cttttctttgg tattctggta atgacagcag tgagaaaaga    900
taaccacacg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacg agtaccactc ggtgaatact acgtgaagga     1320
gttatcaaag cctgtgcacg gtagttgtcg taatattacg tgtgacaatt ggttcacctc    1380
aatcccttgc gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
```

```
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                       2472

<210> SEQ ID NO 81
<211> LENGTH: 2472
<212> TYPE: DNA
<213> ORGANISM: Trichoplusia ni

<400> SEQUENCE: 81
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttac gtgactttta agatttaact catacgataa      240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat ttttactga tgagataatt tcggaaattg taaaatggac      780
aaatgctgag atatcattga aacgtcggga atctatgaca ggtgctacat tcgtgacac      840 gaatgaagat gaaatctatg ctttctttgg tattctggta atgacagcag tgagaaaaga     900
taaccacgtg tccacagatg acctctttga tcgatctttg tcaatggtgt acgtctctgt     960
aatgagtcgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
```

```
gttatcaaag cctgtgcacg gtagttgtcg taatattacg tgtgacaatt ggttcacctc    1380 aatcccttttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaacttaa tatctattca aattaataaa taaacctcga tatacagacc    2400
gataaaacac atgcgtcaat tttacgcatg attatcttta acgtacgtca caatatgatt    2460 atcttttctag gg                                                       2472
```

<210> SEQ ID NO 82
<211> LENGTH: 2472
<212> TYPE: DNA
<213> ORGANISM: Trichoplusia ni

<400> SEQUENCE: 82

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttac gtgacttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa atcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat ttttactga tgagataatt tcggaaattg taaaatggac     780
aaatgctgag atatcattga aacgtcggga atctatgaca ggtgctacat tcgtgacac     840 gaatgaagat gaaatctatg ctttctttgg tattctggta atgacagcag tgagaaaga     900 taaccacatg tccacagatg acctctttga tcgatctttg tcaatggtgt acgtctctgt     960
```

```
aatgagccgt gatcgttttg attttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata acattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat tgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttgta    2220 aaagagagaa tgtttaaaag ttttgttact ttatagaaga aattttgagt ttttgttttt    2280 ttttaataa taaataaaca taaataaata gtttgttgaa tttattatta gtatgtaagt    2340
gtaaatataa taaacttaa tatctattca aattaataaa taaacctcga tatacagacc    2400
gataaaacac atgcgtcaat tttacgcatg attatcttta acgtacgtca caatatgatt    2460
atctttctag gg                                                       2472
```

<210> SEQ ID NO 83
<211> LENGTH: 2472
<212> TYPE: DNA
<213> ORGANISM: Trichoplusia ni

<400> SEQUENCE: 83

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttac gtgactttta agattaact catacgataa     240 ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
```

```
acaaccaggt tcttcattgg cttctaacaa atcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgac acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat tgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaacttaa tatctattca aattaataaa taaacctcga tatacagacc   2400
gataaaacac atgcgtcaat tttacgcatg attatcttta acgtacgtca caatatgatt   2460
atctttctag gg                                                      2472

<210> SEQ ID NO 84
<211> LENGTH: 2472
<212> TYPE: DNA
<213> ORGANISM: Trichoplusia ni

<400> SEQUENCE: 84
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
```

```
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840 gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat   1020
acggcccaca cttcgagaaa acgatgtatt tactcctgtt agaaaaatat gggatctctt    1080
tatccatcag tgcatacaaa attacactcc agggctcat ttgaccatag atgaacagtt     1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
gcgaccaaac gcacgcgaga taccggaagt actgaaaaac agtcgctcca ggccagtggg    1500
aacatcgatg ttttgttttg acggaccct tactctcgtc tcatataaac cgaagccagc     1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaaagttat tgtcgagag cataatattg atatgtgcca     2100
aagttgtttc tgactgacta ataagtataa tttgtttcta ttatgtataa gttaagctaa    2160
ttacttattt tataatacaa catgactgtt tttaaagtac aaaataagtt tattttttgta   2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472
```

<210> SEQ ID NO 85
<211> LENGTH: 2472
<212> TYPE: DNA
<213> ORGANISM: Trichoplusia ni

<400> SEQUENCE: 85

| | | | | | |
|---|---|---|---|---|---|
| ccctagaaag | atagtctgcg | taaaattgac | gcatgcattc | ttgaaatatt | gctctctctt | 60 |
| tctaaatagc | gcgaatccgt | cgctgtgcgt | ttaggacatc | tcagtcgccg | cttggagctc | 120 |
| ccgtgaggcg | tgcttgtcaa | tgcggtaagt | gtcactgatt | ttgaactata | acgaccgcgt | 180 |
| gagtcaaaat | gacgcatgat | tatctttttac | gtgacttttta | agatttaact | catacgataa | 240 |
| ttatattgtt | atttcatgtt | ctacttacgt | gataacttat | tatatatata | ttttcttgtt | 300 |
| atagatatcg | tgactaatat | ataataaaat | gggtagttct | ttagacgatg | agcatatcct | 360 |
| ctctgctctt | ctgcaaagcg | atgacgagct | tgttggtgag | gattctgaca | gtgaaatatc | 420 |
| agatcacgta | agtgaagatg | acgtccagag | cgatacagaa | gaagcgttta | tagatgaggt | 480 |
| acatgaagtg | cagccaacgt | caagcggtag | tgaaatatta | gacgaacaaa | atgttattga | 540 |
| acaaccaggt | tcttcattgg | cttctaacaa | aatcttgacc | ttgccacaga | ggactattag | 600 |
| aggtaagaat | aaacattgtt | ggtcaacttc | aaagtccacg | aggcgtagcc | gagtctctgc | 660 |
| actgaatcat | gtcagatctc | aaagaggtcc | gacgcgtatg | tgccgcaata | tatatgaccc | 720 |
| acttttatgc | ttcaaactat | tttttactga | tgagataatt | tcggaaattg | taaaatggac | 780 |
| aaatgctgag | atatcattga | aacgtcggga | atctatgaca | ggtgctacat | ttcgtgacac | 840 |
| gaatgaagat | gaaatctatg | ctttctttgg | tattctggta | atgacagcag | tgagaaaaga | 900 |
| taaccacatg | tccacagatg | acctctttga | tcgatctttg | tcaatggtgt | acgtctctgt | 960 |
| aatgagtcgt | gatcgttttg | attttttgat | acgatgtctt | agaatggatg | acaaaagtat | 1020 |
| acggcccaca | cttcgagaaa | acgatgtatt | tactcctgtt | agaaaaatat | gggatctctt | 1080 |
| tatccatcag | tgcatacaaa | attacactcc | aggggctcat | ttgaccatag | atgaacagtt | 1140 |
| acttggtttt | agaggacggt | gtccgtttag | gatgtatatc | ccaaacaagc | caagtaagta | 1200 |
| tggaataaaa | atcctcatga | tgtgtgacag | tggtacaaag | tatatgataa | atggaatgcc | 1260 |
| ttatttggga | agaggaacac | agaccaacgg | agtaccactc | ggtgaatact | acgtgaagga | 1320 |
| gttatcaaag | cctgtgcacg | gtagttgtcg | taatattacg | tgtgacaatt | ggttcacctc | 1380 |
| aatccctttg | gcaaaaaact | tactacaaga | accgtataag | ttaaccattg | tgggaaccgt | 1440 |
| gcgatcaaac | gcacgcgaga | taccggaagt | actgaaaacc | agtcgctcca | ggccagtggg | 1500 |
| aacatcgatg | ttttgttttg | acggaccect | tactctcgtc | tcatataaac | cgaagccagc | 1560 |
| taagatggta | tacttattat | catcttgtga | tgaggatgct | tctatcaacg | aaagtaccgg | 1620 |
| taaaccgcaa | atggttatgt | attataatca | aactaaaggc | ggagtggaca | cgctagacca | 1680 |
| aatgtgttct | gtgatgacct | gcagtaggaa | gacgaatagg | tggcctatgg | cattattgta | 1740 |
| cggaatgata | aacattgcct | gcataaaattc | ttttattata | tacagccata | atgtcagtag | 1800 |
| caagggagaa | aaggttcaaa | gtcgcaaaaa | atttatgaga | aaccctttaca | tgagcctgac | 1860 |
| gtcatcgttt | atgcgtaagc | gtttagaagc | tcctactttg | aagagatatt | tgcgcgataa | 1920 |
| tatctctaat | attttgccaa | atgaagtgcc | tggtacatca | gatgacagta | ctgaagagcc | 1980 |
| agtaacgaaa | aaacgtactt | actgtactta | ctgcccctct | aaaataaggc | gaaaggcaaa | 2040 |
| tgcatcgtgc | aaaaaatgca | aaaaagttat | ttgtcgagag | cataatattg | atatgtgcca | 2100 |
| aagttgtttc | tgactgacta | ataagtataa | tttgtttcta | ttatgtataa | gttaagctaa | 2160 |

```
ttacttattt tataatacaa catgactgtt tttaaagtac aaaataagtt tattttttgta    2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                        2472
```

<210> SEQ ID NO 86
<211> LENGTH: 2472
<212> TYPE: DNA
<213> ORGANISM: Trichoplusia ni
<400> SEQUENCE: 86

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840 gaatgaagat gaaatctatg cttctttggg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgagttct gtgatgacct gcagtaggaa gacgaatagg tggcctatgg cattattgta   1740
```

| | |
|---|---|
| cggaatgata aacattgcct gcataaattc ttttattata tacagccata atgtcagtag | 1800 |
| caagggagaa aaggttcaaa gtcgcaaaaa atttatgaga aacctttaca tgagcctgac | 1860 |
| gtcatcgttt atgcgtaagc gtttagaagc tcctactttg aagagatatt tgcgcgataa | 1920 |
| tatctctaat atttttgccaa atgaagtgcc tggtacatca gatgcacagta ctgaagagcc | 1980 |
| agtaacgaaa aaacgtactt actgtactta ctgcccctct aaaataaggc gaaaggcaag | 2040 |
| tgcatcgtgc aaaaaatgca aaaagttat tgtcgagag cataatattg atatgtgcca | 2100 |
| aagttgtttc tgactgacta ataagtataa tttgtttcta ttatgtataa gttaagctaa | 2160 |
| ttacttattt tataatacaa catgactgtt tttaaagtac aaaataagtt tattttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 87
<211> LENGTH: 2472
<212> TYPE: DNA
<213> ORGANISM: Trichoplusia ni

<400> SEQUENCE: 87

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatcttttac gtgactttta agatttaact catacgataa | 240 |
| ttatattgtt atttcatgtt ctacttacgt gataacttat tatatatata ttttcttgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat ttttttactga tgagataatt tcggaaattg taaaatggac | 780 |
| aaatgctgag atatcattga aacgtcggga atctatgaca ggtgctacat tcgtgacac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg attttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |

```
aatcccttctg gcaaaaaact tactacaaga accgtataag ttaaccattg tgggaaccgt      1440
gcgatcaaac gcacgcgaga taccggaagt actgaaaaac agtcgctcca ggccagtggg      1500
aacatcgatg ttttgttttg acggacccct tactctcgtc tcatataaac cgaagccagc      1560
taagatggta tacttattat catcttgtga tgaggatgct tctatcaacg aaagtaccgg      1620
taaaccgcaa atggttatgt attataatca aactaaaggc ggagtggaca cgctagacca      1680
aatgtgttct gtgatgacct gcagtaggaa gacgaatagg tggcctatgg cattattgta      1740
cggaatgata acattgcct gcataaattc ttttattata tacagccata atgtcagtag       1800
caagggagaa aaggttcaaa gtcgcaaaaa atttatgaga aacctttaca tgagcctgac      1860
gtcatcgttt atgcgtaagc gtttagaagc tcctactttg aagagatatt tgcgcgataa      1920
tatctctaat attttgccaa atgaagtgcc tggtacatca gatgacagta ctgaagagcc      1980
agtaacgaaa aaacgtactt actgtgctta ctgccctct aaaataaggc gaaaggcaaa      2040
tgcatcgtgc aaaaaatgca aaaagttat ttgtcgagag cataatattg atatgtgcca      2100
aagttgtttc tgactgacta ataagtataa tttgtttcta ttatgtataa gttaagctaa      2160
ttacttattt tataatacaa catgactgtt tttaaagtac aaaataagtt tattttttgta    2220 aaagagagaa tgtttaaag ttttgttact ttatagaaga aattttgagt ttttgtttt       2280 ttttaataaa taaataaaca taaataaata gtttgttgaa tttattatta gtatgtaagt     2340
gtaaatataa taaaacttaa tatctattca aattaataaa taaacctcga tatacagacc     2400
gataaaacac atgcgtcaat tttacgcatg attatcttta acgtacgtca caatatgatt    2460
atctttctag gg                                                          2472

<210> SEQ ID NO 88
<211> LENGTH: 2472
<212> TYPE: DNA
<213> ORGANISM: Trichoplusia ni

<400> SEQUENCE: 88
ccctagaaag atagtctgcg taaaattgac gcatgcattc ttgaaatatt gctctctctt        60
tctaaatagc gcgaatccgt cgctgtgcgt ttaggacatc tcagtcgccg cttggagctc       120
ccgtgaggcg tgcttgtcaa tgcggtaagt gtcactgatt ttgaactata acgaccgcgt       180
gagtcaaaat gacgcatgat tatctttac gtgactttta agatttaact catacgataa       240
ttatattgtt atttcatgtt ctacttacgt gataacttat tatatatata ttttcttgtt      300
atagatatcg tgactaatat ataataaaat gggtagttct ttagacgatg agcatatcct      360
ctctgctctt ctgcaaagcg atgacgagct tgttggtgag gattctgaca gtgaaatatc      420
agatcacgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa aatcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat tttttactga tgagataatt tcggaaattg taaaatggac      780
aaatgctgag atatcattga aacgtcggga atctatgaca ggtgctacat tcgtgacac       840 gaatgaagat gaaatctatg ctttctttgg tattctggta atgacagcag tgagaaaaga     900
taaccacatg tccacagatg acctctttga tcgatctttg tcaatggtgt acgtctctgt    960
```

```
aatgagtcgt gatcgttttg atttttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380 aatcccttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatt ttttgttttg acggacccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat atttttgccaa atgaagtgcc tggtacatca gatgacagta ctgaagagcc    1980
agtaacgaaa aaacgtactt actgtactta ctgcccctct aaaataaggc gaaaggcaaa    2040
ggcatcgtgc aaaaatgca aaaagtat ttgtcgagag cataatattg atatgtgcca    2100
aagttgtttc tgactgacta ataagtataa tttgtttcta ttatgtataa gttaagctaa    2160
ttacttattt tataatacaa catgactgtt tttaaagtac aaaataagtt tattttttgta    2220 aaagagagaa tgtttaaaag ttttgttact ttatagaaga aattttgagt tttgttttt    2280 ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                       2472
```

<210> SEQ ID NO 89
<211> LENGTH: 2472
<212> TYPE: DNA
<213> ORGANISM: Trichoplusia ni

<400> SEQUENCE: 89

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatctttttac gtgacttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
```

```
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg cttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380 aatcccttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggaccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcagcgtgc aaaaaatgca aaaaagttat ttgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttgta    2220 aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 90
<211> LENGTH: 2472
<212> TYPE: DNA
<213> ORGANISM: Trichoplusia ni

<400> SEQUENCE: 90

```
ccctagaaag atagtctgcg taaaattgac gcatgcattc ttgaaatatt gctctctctt     60
tctaaatagc gcgaatccgt cgctgtgcgt ttaggacatc tcagtcgccg cttgagctc    120 ccgtgaggcg tgcttgtcaa tgcggtaagt gtcactgatt ttgaactata acgaccgcgt   180
```

```
gagtcaaaat gacgcatgat tatcttttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg ctttctttgg tattctggta atgacagcag tgagaaaaga    900
taaccacatg tccacagatg acctcttttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380 aatcccttttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat ttgtcgagag cataatattg atatgtgcca   2100
aagttgtttc tgactgacta ataagtaaa ttttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                       2472
```

<210> SEQ ID NO 91
<211> LENGTH: 2472
<212> TYPE: DNA
<213> ORGANISM: Trichoplusia ni

<400> SEQUENCE: 91

```
ccctagaaag atagtctgcg taaaattgac gcatgcattc ttgaaatatt gctctctctt      60
tctaaatagc gcgaatccgt cgctgtgcgt ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacaa aatcttgacc ttgccacaga ggactattag     600
aggtaagaat aaacattgtt ggtcaacttc aaagtccacg aggcgtagcc gagtctctgc     660
actgaatcat gtcagatctc aaagaggtcc gacgcgtatg tgccgcaata tatatgaccc     720
acttttatgc ttcaaactat tttttactga tgagataatt tcggaaattg taaaatggac     780
aaatgctgag atatcattga aacgtcggga atctatgaca ggtgctacat tcgtgacac     840
gaatgaagat gaaatctatg ctttctttgg tattctggta atgacagcag tgagaaaaga     900
taaccacatg tccacagatg acctctttga tcgatctttg tcaatggtgt acgtctctgt     960
aatgagtcgt gatcgttttg atttttttgat acgatgtctt agaatggatg acaaaagtat    1020
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgcacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg ttttgttttg acggaccccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaatagg tggcctatgg cattattgta    1740
cggaatgata aacattgcct gcataaaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctacttg aagagatatt tgcgcgataa    1920
tatctctaat attttgccaa atgaagtgcc tggtacatca gatgacagta ctgaagagcc    1980
agtaacgaaa aaacgtactt actgtactta ctgccctct aaaataaggc gaaaggcaaa    2040
tgcatcgtgc aaaaaatgca aaaaagttat tgtcgagag cataatattg atgtgtgcca    2100
aagttgtttc tgactgacta ataagtataa tttgtttcta ttatgtataa gttaagctaa    2160
```

| | |
|---|---|
| ttacttattt tataatacaa catgactgtt tttaaagtac aaaataagtt tattttgta | 2220 |
| aaagagagaa tgtttaaaag ttttgttact ttatagaaga aattttgagt ttttgttttt | 2280 |
| ttttaataaa taaataaaca taaataaata gtttgttgaa tttattatta gtatgtaagt | 2340 |
| gtaaatataa taaaacttaa tatctattca aattaataaa taaacctcga tatacagacc | 2400 |
| gataaaacac atgcgtcaat tttacgcatg attatcttta acgtacgtca caatatgatt | 2460 |
| atctttctag gg | 2472 |

<210> SEQ ID NO 92
<211> LENGTH: 2472
<212> TYPE: DNA
<213> ORGANISM: Trichoplusia ni

<400> SEQUENCE: 92

| | |
|---|---|
| ccctagaaag atagtctgcg taaaattgac gcatgcattc ttgaaatatt gctctctctt | 60 |
| tctaaatagc gcgaatccgt cgctgtgcgt ttaggacatc tcagtcgccg cttggagctc | 120 |
| ccgtgaggcg tgcttgtcaa tgcggtaagt gtcactgatt ttgaactata acgaccgcgt | 180 |
| gagtcaaaat gacgcatgat tatctttttac gtgacttttta agatttaact catacgataa | 240 |
| ttatattgtt atttcatgtt ctacttacgt gataaacttat tatatatata tttctctgtt | 300 |
| atagatatcg tgactaatat ataataaaat gggtagttct ttagacgatg agcatatcct | 360 |
| ctctgctctt ctgcaaagcg atgacgagct tgttggtgag gattctgaca gtgaaatatc | 420 |
| agatcacgta agtgaagatg acgtccagag cgatacagaa gaagcgttta tagatgaggt | 480 |
| acatgaagtg cagccaacgt caagcggtag tgaaatatta gacgaacaaa atgttattga | 540 |
| acaaccaggt tcttcattgg cttctaacaa aatcttgacc ttgccacaga ggactattag | 600 |
| aggtaagaat aaacattgtt ggtcaacttc aaagtccacg aggcgtagcc gagtctctgc | 660 |
| actgaatcat gtcagatctc aaagaggtcc gacgcgtatg tgccgcaata tatatgaccc | 720 |
| acttttatgc ttcaaactat tttttactga tgagataatt tcggaaattg taaaatggac | 780 |
| aaatgctgag atatcattga aacgtcggga atctatgaca ggtgctacat tcgtgatac | 840 |
| gaatgaagat gaaatctatg ctttctttgg tattctggta atgacagcag tgagaaaaga | 900 |
| taaccacatg tccacagatg acctctttga tcgatctttg tcaatggtgt acgtctctgt | 960 |
| aatgagtcgt gatcgttttg attttttgat acgatgtctt agaatggatg acaaaagtat | 1020 |
| acggcccaca cttcgagaaa acgatgtatt tactcctgtt agaaaaatat gggatctctt | 1080 |
| tatccatcag tgcatacaaa attacactcc aggggctcat ttgaccatag atgaacagtt | 1140 |
| acttggtttt agaggacggt gtccgtttag gatgtatatc ccaaacaagc caagtaagta | 1200 |
| tggaataaaa atcctcatga tgtgtgacag tggtacaaag tatatgataa atggaatgcc | 1260 |
| ttatttggga agaggaacac agaccaacgg agtaccactc ggtgaatact acgtgaagga | 1320 |
| gttatcaaag cctgtgcacg gtagttgtcg taatattacg tgtgacaatt ggttcacctc | 1380 |
| aatcccttg gcaaaaaact tactacaaga accgtataag ttaaccattg tgggaaccgt | 1440 |
| gcgatcaaac gcacgcgaga taccggaagt actgaaaaac agtcgctcca ggccagtggg | 1500 |
| aacatcgatg ttttgttttg acggaccccct tactctcgtc tcatataaac cgaagccagc | 1560 |
| taagatggta tacttattat catcttgtga tgaggatgct tctatcaacg aaagtaccgg | 1620 |
| taaaccgcaa atggttatgt attataatca aactaaaggc ggagtggaca cgctagacca | 1680 |
| aatgtgttct gtgatgacct gcagtaggaa gacgaatagg tggcctatgg cattattgta | 1740 |
| cggaatgata aacattgcct gcataaattc ttttattata tacagccata atgtcagtag | 1800 |

```
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat  ttgtcgagag cataatattg atgtgtgcca    2100
aagttgtttc tgactgacta ataagtataa tttgtttcta ttatgtataa gttaagctaa    2160
ttacttattt tataatacaa catgactgtt tttaaagtac aaaataagtt tattttgta     2220
aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaacttaa  tatctattca aattaataaa taaacctcga tatacagacc    2400
gataaaacac atgcgtcaat tttacgcatg attatcttta acgtacgtca caatatgatt    2460
atctttctag gg                                                         2472

<210> SEQ ID NO 93
<211> LENGTH: 2472
<212> TYPE: DNA
<213> ORGANISM: Trichoplusia ni

<400> SEQUENCE: 93
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttac  gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840
gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
```

| | | | | |
|---|---|---|---|---|
| aatccctttg | gcaaaaaact | tactacaaga | accgtataag | ttaaccattg tgggaaccgt | 1440 |
| gcgatcaaac | gcacgcgaga | taccggaagt | actgaaaaac | agtcgctcca ggccagtggg | 1500 |
| aacatcgatg | ttttgttttg | acggacccct | tactctcgtc | tcatataaac cgaagccagc | 1560 |
| taagatggta | tacttattat | catcttgtga | tgaggatgct | tctatcaacg aaagtaccgg | 1620 |
| taaaccgcaa | atggttatgt | attataatca | aactaaaggc | ggagtggaca cgctagacca | 1680 |
| aatgtgttct | gtgatgacct | gcagtaggaa | gacgaatagg | tggcctatgg cattattgta | 1740 |
| cggaatgata | aacattgcct | gcataaattc | ttttattata | tacagccata atgtcagtag | 1800 |
| caagggagaa | aaggttcaaa | gtcgcaaaaa | atttatgaga | aacctttaca tgagcctgac | 1860 |
| gtcatcgttt | atgcgtaagc | gtttagaagc | tcctactttg | aagagatatt tgcgcgataa | 1920 |
| tatctctaat | attttgccaa | atgaagtgcc | tggtacatca | gatgacagta ctgaagagcc | 1980 |
| agtaacgaaa | aaacgtactt | actgtactta | ctgcccctct | aaaataaggc gaaaggcaaa | 2040 |
| tgcatcgtgc | aaaaaatgca | aaaaagttat | tgtcgagag | cataatattg atatgtgcca | 2100 |
| aggttgtttc | tgactgacta | ataagtataa | tttgtttcta | ttatgtataa gttaagctaa | 2160 |
| ttacttattt | tataatacaa | catgactgtt | tttaaagtac | aaaataagtt tattttgta | 2220 |
| aaagagagaa | tgtttaaaag | ttttgttact | ttatagaaga | aattttgagt ttttgttttt | 2280 |
| ttttaataaa | taaataaaca | taaataaata | gtttgttgaa | tttattatta gtatgtaagt | 2340 |
| gtaaatataa | taaaacttaa | tatctattca | aattaataaa | taaacctcga tatacagacc | 2400 |
| gataaaacac | atgcgtcaat | tttacgcatg | attatcttta | acgtacgtca caatatgatt | 2460 |
| atctttctag | gg | | | | 2472 |

<210> SEQ ID NO 94
<211> LENGTH: 2472
<212> TYPE: DNA
<213> ORGANISM: Trichoplusia ni

<400> SEQUENCE: 94

| | | | | |
|---|---|---|---|---|
| ccctagaaag | atagtctgcg | taaaattgac | gcatgcattc | ttgaaatatt gctctctctt | 60 |
| tctaaatagc | gcgaatccgt | cgctgtgcgt | ttaggacatc | tcagtcgccg cttggagctc | 120 |
| ccgtgaggcg | tgcttgtcaa | tgcggtaagt | gtcactgatt | ttgaactata acgaccgcgt | 180 |
| gagtcaaaat | gacgcatgat | tatctttac | gtgactttta | agatttaact catacgataa | 240 |
| ttatattgtt | atttcatgtt | ctacttacgt | gataacttat | tatatatata ttttcttgtt | 300 |
| atagatatcg | tgactaatat | ataataaaat | gggtagttct | ttagacgatg agcatatcct | 360 |
| ctctgctctt | ctgcaaagcg | atgacgagct | tgttggtgag | gattctgaca gtgaaatatc | 420 |
| agatcacgta | agtgaagatg | acgtccagag | cgatacagaa | gaagcgttta tagatgaggt | 480 |
| acatgaagtg | cagccaacgt | caagcggtag | tgaaatatta | gacgaacaaa atgttattga | 540 |
| acaaccaggt | tcttcattgg | cttctaacaa | aatcttgacc | ttgccacaga ggactattag | 600 |
| aggtaagaat | aaacattgtt | ggtcaacttc | aaagtccacg | aggcgtagcc gagtctctgc | 660 |
| actgaatcat | gtcagatctc | aaagaggtcc | gacgcgtatg | tgccgcaata tatatgaccc | 720 |
| acttttatgc | ttcaaactat | tttttactga | tgagataatt | tcggaaattg taaaatggac | 780 |
| aaatgctgag | atatcattga | aacgtcggga | atctatgaca | ggtgctacat tcgtgacac | 840 |
| gaatgaagat | gaaatctatg | ctttctttgg | tattctggta | atgacagcag tgagaaaaga | 900 |
| taaccacatg | tccacagatg | acctcttga | tcgatctttg | tcaatggtgt acgtctctgt | 960 |
| aatgagtcgt | gatcgttttg | atttttttgat | acgatgtctt | agaatggatg acaaaagtat | 1020 |

```
acggcccaca cttcgagaaa acgatgtatt tactcctgtt agaaaaatat gggatctctt    1080
tatccatcag tgcatacaaa attacactcc aggggctcat ttgaccatag atgaacagtt    1140
acttggtttt agaggacggt gtccgtttag gatgtatatc ccaaacaagc caagtaagta    1200
tggaataaaa atcctcatga tgtgtgacag tggtacaaag tatatgataa atggaatgcc    1260
ttatttggga agaggaacac agaccaacgg agtaccactc ggtgaatact acgtgaagga    1320
gttatcaaag cctgtgcacg gtagttgtcg taatattacg tgtgacaatt ggttcacctc    1380
aatccctttg gcaaaaaact tactacaaga accgtataag ttaaccattg tgggaaccgt    1440
gcgatcaaac gcacgcgaga taccggaagt actgaaaaac agtcgctcca ggccagtggg    1500
aacatcgatg tttttgtttg acggaccccct tactctcgtc tcatataaac cgaagccagc    1560
taagatggta tacttattat catcttgtga tgaggatgct tctatcaacg aaagtaccgg    1620
taaaccgcaa atggttatgt attataatca aactaaaggc ggagtggaca cgctagacca    1680
aatgtgttct gtgatgacct gcagtaggaa gacgaataag tggcctatgg cattattgta    1740
cggaatgata aacattgcct gcataaattc ttttattata tacagccata atgtcagtag    1800
caagggagaa aaggttcaaa gtcgcaaaaa atttatgaga aacctttaca tgagcctgac    1860
gtcatcgttt atgcgtaagc gtttagaagc tcctactttg aagagatatt tgcgcgataa    1920
tatctctaat attttgccaa atgaagtgcc tggtacatca gatgacagta ctgaagagcc    1980
agtaacgaaa aaacgtactt actgtactta ctgcccctct aaaataaggc gaaaggcaaa    2040
tgcatcgtgc aaaaaatgca aaaagttat tgtcgagag cataatattg atatgtgcca    2100
aagttgttta tgactgacta ataagtataa tttgtttcta ttatgtataa gttaagctaa    2160
ttacttattt tataatacaa catgactgtt tttaaagtac aaaataagtt tattttgta    2220 aaagagagaa tgtttaaaag ttttgttact ttatagaaga aattttgagt ttttgttttt    2280
ttttaataaa taaataaaca taaataaata gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                         2472
```

<210> SEQ ID NO 95
<211> LENGTH: 2472
<212> TYPE: DNA
<213> ORGANISM: Trichoplusia ni

<400> SEQUENCE: 95

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttac gtgactttta agatttaact catacgataa    240
ttatattgtt atttcatgtt ctacttacgt gataacttat tatatatata ttttcttgtt    300
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacaa aatcttgacc ttgccacaga ggactattag    600
```

```
aggtaagaat aaacattgtt ggtcaacttc aaagtccacg aggcgtagcc gagtctctgc    660
actgaatcat gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat tcgtgacac     840 gaatgaagat gaaatctatg cttctttgg tattctggta atgacagcag tgagaaaaga    900
taaccacatg tccacagatg acctctttga tcgatctttg tcaatggtgt acgtctctgt    960
aatgagtcgt gatcgttttg atttttttgat acgatgtctt agaatggatg acaaaagtat  1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacaaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380
aatccctttg gcaaaaaact tactacaaga accgtataag ttaaccattg tgggaaccgt   1440
gcgatcaaac gcacgcgaga taccggaagt actgaaaaac agtcgctcca ggccagtggg   1500
aacatcgatg ttttgttttg acggaccct  tactctcgtc tcatataaac cgaagccagc    1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaattc ttttattata tacagccata atgtcagtag   1800
caagggagaa aaggttcaaa gtcgcaaaaa atttatgaga aaccttaca tgagcctgac    1860 gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaacgaaa aaacgtactt actgtactta ctgcccctct aaaataaggc gaaaggcaaa   2040
tgcatcgtgc aaaaaatgca aaaaagttat ttgtcgagag cataatattg atatgtgcca   2100
aagttgtttc tggctgacta ataagtataa tttgtttcta ttatgtataa gttaagctaa   2160
ttacttattt tataatacaa catgactgtt tttaaagtac aaaataagtt tatttttgta   2220
aaagagagaa tgtttaaaag ttttgttact ttatagaaga aattttgagt ttttgttttt   2280
ttttaataaa taaataaaca taaataaata gtttgttgaa tttattatta gtatgtaagt   2340
gtaaatataa taaaacttaa tatctattca aattaataaa taaacctcga tatacagacc   2400
gataaaacac atgcgtcaat tttacgcatg attatcttta acgtacgtca caatatgatt   2460
atctttctag gg                                                        2472
```

<210> SEQ ID NO 96
<211> LENGTH: 2472
<212> TYPE: DNA
<213> ORGANISM: Trichoplusia ni

<400> SEQUENCE: 96

```
ccctagaaag atagtctgcg taaaattgac gcatgcattc ttgaaatatt gctctctctt     60
tctaaatagc gcgaatccgt cgctgtgcgt ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttttac gtgactttta agatttaact catacgataa    240
```

```
ttatattgtt atttcatgtt ctacttacgt gataacttat tatatatata ttttcttgtt      300
atagatatcg tgactaatat ataataaaat gggtagttct ttagacgatg agcatatcct      360
ctctgctctt ctgcaaagcg atgacgagct tgttggtgag gattctgaca gtgaaatatc      420
agatcatgta agtgaagatg acgtccagag cgatacagaa gaagcgttta tagatgaggt      480
acatgaagtg cagccaacgt caagcggtag tgaaatatta gacgaacaaa atgttattga      540
acaaccaggt tcttcattgg cttctaacaa aatcttgacc ttgccacaga ggactattag      600
aggtaagaat aaacattgtt ggtcaacttc aaagtccacg aggcgtagcc gagtctctgc      660
actgaatcat gtcagatctc aaagaggtcc gacgcgtatg tgccgcaata tatatgaccc      720
acttttatgc ttcaaactat tttttactga tgagataatt tcggaaattg taaaatggac      780 aaaatgctgag atatcattga aacgtcggga atctatgaca ggtgctacat tcgtgacac       840 gaatgaagat gaaatctatg ctttctttgg tattctggta atgacagcag tgagaaaaga      900
taaccacatg tccacagatg acctctttga tcgatctttg tcaatggtgt acgtctctgt      960
aatgagtcgt gatcgttttg attttttgat acgatgtctt agaatggatg acaaaagtat     1020
acggcccaca cttcgagaaa acgatgtatt tactcctgtt agaaaaatat gggatctctt     1080
tatccatcag tgcatacaaa attacactcc aggggctcat ttgaccatag atgaacagtt     1140
acttggtttt agaggacggt gtccgtttag gatgtatatc ccaaacaagc caagtaagta     1200
tggaataaaa atcctcatga tgtgtgacag tggtacaaag tatatgataa atggaatgcc     1260
ttatttggga agaggaacac agaccaacgg agtaccactc ggtgaatact acgtgaagga     1320
gttatcaaag cctgtgcacg gtagttgtcg taatattacg tgtgacaatt ggttcacctc     1380 aatcccttg gcaaaaaact tactacaaga accgtataag ttaaccattg tgggaaccgt      1440
gcgatcaaac gcacgcgaga taccggaagt actgaaaaac agtcgctcca ggccagtggg     1500
aacatcgatg ttttgttttg acggacccct tactctcgtc tcatataaac cgaagccagc     1560
taagatggta tacttattat catcttgtga tgaggatgct tctatcaacg aaagtaccgg     1620
taaaccgcaa atggttatgt attataatca aactaaaggc ggagtggaca cgctagacca     1680
aatgtgttct gtgatgacct gcagtaggaa gacgaatagg tggcctatgg cattattgta     1740
cggaatgata aacattgcct gcataaattc ttttattata tacagccata atgtcagtag     1800
caagggagaa aaggttcaaa gtcgcaaaaa atttatgaga aacctttaca tgagcctgac     1860
gtcatcgttt atgcgtaagc gtttagaagc tcctactttg aagagatatt tgcgcgataa     1920
tatctctaat atttttgccaa atgaagtgcc tggtacatca gatgacagta ctgaagagcc     1980
agtaacgaaa aaacgtactt actgtactta ctgcccctct aaaataaggc gaaaggcaaa     2040
tgcatcgtgc aaaaaatgca aaaaagttat tgtcgagag cataatattg atatgtgcca      2100
aagttgtttc ggactgacta ataagtataa tttgtttcta ttatgtataa gttaagctaa     2160
ttacttattt tataatacaa catgactgtt tttaaagtac aaaataagtt tattttgta     2220 aaagagagaa tgtttaaaag ttttgttact ttatagaaga aattttgagt ttttgttttt     2280
ttttaataaa taaataaaca taaataaata gtttgttgaa tttattatta gtatgtaagt     2340
gtaaatataa taaaacttaa tatctattca aattaataaa taaacctcga tatacagacc     2400
gataaaacac atgcgtcaat tttacgcatg attatcttta acgtacgtca caatatgatt     2460
atctttctag gg                                                         2472
```

<210> SEQ ID NO 97

<211> LENGTH: 594
<212> TYPE: PRT
<213> ORGANISM: Trichoplusia ni

<400> SEQUENCE: 97

```
Met Gly Ser Ser Leu Asp Asp Glu His Ile Leu Ser Ala Leu Pro Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
```

```
                385                 390                 395                 400
Leu Thr Leu Val Ser Tyr Lys Pro Lys Pro Ala Lys Met Val Tyr Leu
                    405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Val Asp Thr
            435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 98
<211> LENGTH: 594
<212> TYPE: PRT
<213> ORGANISM: Trichoplusia ni

<400> SEQUENCE: 98

Met Gly Ser Ser Leu Asp Asp Glu His Ile Leu Ser Ala Leu Leu Gln
1               5                   10                  15

Ser Asp Asn Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
```

-continued

```
                165                 170                 175
Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Leu Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590
```

Cys Phe

<210> SEQ ID NO 99
<211> LENGTH: 594
<212> TYPE: PRT
<213> ORGANISM: Trichoplusia ni

<400> SEQUENCE: 99

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Pro Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Ala Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
         370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 100
<211> LENGTH: 594
<212> TYPE: PRT
<213> ORGANISM: Trichoplusia ni

<400> SEQUENCE: 100

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

Tyr Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

```
Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Arg Ser Asn Ala Arg Glu Ile Pro Glu Val Leu Lys Asn
                370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Asn Glu Val Pro Gly Thr Ser
                530                 535                 540

Asp Asp Ser Thr Glu Glu Pro Val Thr Lys Lys Arg Thr Tyr Cys Thr
545                 550                 555                 560
```

Tyr Cys Pro Ser Lys Ile Arg Arg Lys Ala Asn Ala Ser Cys Lys Lys
              565                 570                 575

Cys Lys Lys Val Ile Cys Arg Glu His Asn Ile Asp Met Cys Gln Ser
              580                 585                 590

Cys Phe

<210> SEQ ID NO 101
<211> LENGTH: 594
<212> TYPE: PRT
<213> ORGANISM: Trichoplusia ni

<400> SEQUENCE: 101

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Lys Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Arg Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 102
<211> LENGTH: 594
<212> TYPE: PRT
<213> ORGANISM: Trichoplusia ni

<400> SEQUENCE: 102

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Gly Ala Phe Ile
        35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

-continued

```
Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
```

```
            530                 535                 540
Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 103
<211> LENGTH: 594
<212> TYPE: PRT
<213> ORGANISM: Trichoplusia ni

<400> SEQUENCE: 103

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Arg Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Ile Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
```

```
            305                 310                 315                 320
    Gly Val Pro Leu Gly Glu Tyr Tyr Val Lys Glu Leu Ser Lys Pro Val
                    325                 330                 335

His Gly Ser Cys Arg Asn Ile Thr Cys Asp Asn Trp Phe Thr Ser Ile
                    340                 345                 350

Pro Leu Ala Lys Asn Leu Leu Gln Glu Pro Tyr Lys Leu Thr Ile Val
                    355                 360                 365

Gly Thr Val Arg Ser Asn Ala Arg Glu Ile Pro Glu Val Leu Lys Asn
                    370                 375                 380

Ser Arg Ser Arg Pro Val Gly Thr Ser Met Phe Cys Phe Asp Gly Pro
    385                 390                 395                 400

Leu Thr Leu Val Ser Tyr Lys Pro Lys Pro Ala Lys Met Val Tyr Leu
                    405                 410                 415

Leu Ser Ser Cys Asp Glu Asp Ala Ser Ile Asn Glu Ser Thr Gly Lys
                    420                 425                 430

Pro Gln Met Val Met Tyr Tyr Asn Gln Thr Lys Gly Gly Val Asp Thr
                    435                 440                 445

Leu Asp Gln Met Cys Ser Val Met Thr Cys Ser Arg Lys Thr Asn Arg
                    450                 455                 460

Trp Pro Met Ala Leu Leu Tyr Gly Met Ile Asn Ile Ala Cys Ile Asn
    465                 470                 475                 480

Ser Phe Ile Ile Tyr Ser His Asn Val Ser Ser Lys Gly Glu Lys Val
                    485                 490                 495

Gln Ser Arg Lys Lys Phe Met Arg Asn Leu Tyr Met Ser Leu Thr Ser
                    500                 505                 510

Ser Phe Met Arg Lys Arg Leu Glu Ala Pro Thr Leu Lys Arg Tyr Leu
                    515                 520                 525

Arg Asp Asn Ile Ser Asn Ile Leu Pro Asn Glu Val Pro Gly Thr Ser
                    530                 535                 540

Asp Asp Ser Thr Glu Glu Pro Val Thr Lys Lys Arg Thr Tyr Cys Thr
    545                 550                 555                 560

Tyr Cys Pro Ser Lys Ile Arg Arg Lys Ala Asn Ala Ser Cys Lys Lys
                    565                 570                 575

Cys Lys Lys Val Ile Cys Arg Glu His Asn Ile Asp Met Cys Gln Ser
                    580                 585                 590

Cys Phe

<210> SEQ ID NO 104
<211> LENGTH: 594
<212> TYPE: PRT
<213> ORGANISM: Trichoplusia ni

<400> SEQUENCE: 104

Met Gly Ser Ser Leu Asp Asp Glu His Ile Leu Ser Ala Leu Leu Gln
    1               5                   10                  15

Ser Asp Asp Glu Leu Val Gly Glu Asp Ser Asp Ser Glu Ile Ser Asp
                    20                  25                  30

His Val Ser Glu Asp Asp Val Gln Ser Asp Thr Glu Glu Ala Phe Ile
                    35                  40                  45

Asp Glu Val His Glu Val Gln Pro Thr Ser Ser Gly Ser Glu Ile Leu
                    50                  55                  60

Asp Glu Gln Asn Val Ile Glu Gln Pro Gly Ser Ser Leu Ala Ser Asn
    65                  70                  75                  80

Lys Ile Leu Thr Leu Pro Gln Arg Thr Ile Arg Gly Lys Asn Lys His
```

```
                    85                  90                  95
Cys Trp Ser Thr Ser Lys Pro Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Gly Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Lys Gly Glu Lys Val
                485                 490                 495

Gln Ser Arg Lys Lys Phe Met Arg Asn Leu Tyr Met Ser Leu Thr Ser
            500                 505                 510
```

```
Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 105
<211> LENGTH: 594
<212> TYPE: PRT
<213> ORGANISM: Trichoplusia ni

<400> SEQUENCE: 105

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Val Gln Ser Asp Thr Glu Glu Ala Phe Ile
                35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Lys Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285
```

```
Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                    325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                    405                 410                 415

Leu Ser Ser Cys Asp Glu Asp Ala Ser Ile Asn Glu Ser Thr Gly Lys
                420                 425                 430

Pro Gln Met Val Met Tyr Asn Gln Thr Lys Gly Gly Val Asp Thr
            435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                    485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
        530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                    565                 570                 575

Cys Lys Lys Val Ile Cys Arg Glu His Asn Ile Asp Met Cys Gln Ser
                580                 585                 590

Cys Phe

<210> SEQ ID NO 106
<211> LENGTH: 594
<212> TYPE: PRT
<213> ORGANISM: Trichoplusia ni

<400> SEQUENCE: 106

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60
```

```
Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asn Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480
```

```
Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
        500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
        530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 107
<211> LENGTH: 594
<212> TYPE: PRT
<213> ORGANISM: Trichoplusia ni

<400> SEQUENCE: 107

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Thr Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255
```

```
Gln Asn Tyr Thr Pro Gly Ala His Leu Thr Ile Asp Glu Gln Leu Leu
                260                 265                 270
Gly Phe Arg Gly Arg Cys Pro Phe Arg Met Tyr Ile Pro Asn Lys Pro
            275                 280                 285
Ser Lys Tyr Gly Ile Lys Ile Leu Met Met Cys Asp Ser Gly Thr Lys
        290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Val Lys Glu Leu Ser Lys Pro Val
                325                 330                 335
His Gly Ser Cys Arg Asn Ile Thr Cys Asp Asn Trp Phe Thr Ser Ile
                340                 345                 350
Pro Leu Ala Lys Asn Leu Leu Gln Glu Pro Tyr Lys Leu Thr Ile Val
                355                 360                 365
Gly Thr Val Arg Ser Asn Ala Arg Glu Ile Pro Glu Val Leu Lys Asn
                370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
                420                 425                 430
Pro Gln Met Val Met Tyr Tyr Asn Gln Thr Lys Gly Gly Val Asp Thr
                435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
                500                 505                 510
Ser Phe Met Arg Lys Arg Leu Glu Ala Pro Thr Leu Lys Arg Tyr Leu
                515                 520                 525
Arg Asp Asn Ile Ser Asn Ile Leu Pro Asn Glu Val Pro Gly Thr Ser
                530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
                580                 585                 590
Cys Phe

<210> SEQ ID NO 108
<211> LENGTH: 594
<212> TYPE: PRT
<213> ORGANISM: Trichoplusia ni

<400> SEQUENCE: 108

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
                20                  25                  30
```

```
His Val Ser Glu Asp Asp Val Gln Ser Asp Thr Glu Glu Ala Phe Ile
         35                  40                  45

Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Val Ser Thr Asp Leu Phe Asp Arg Ser Leu Ser Met Val Tyr
            195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
```

```
            450                 455                 460
Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 109
<211> LENGTH: 594
<212> TYPE: PRT
<213> ORGANISM: Trichoplusia ni

<400> SEQUENCE: 109

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
```

```
            225                 230                 235                 240
        Phe Thr Pro Val Arg Lys Ile Trp Asp Leu Phe Ile His Gln Cys Ile
                        245                 250                 255
        Gln Asn Tyr Thr Pro Gly Ala His Leu Thr Ile Asp Glu Gln Leu Leu
                        260                 265                 270
        Gly Phe Arg Gly Arg Cys Pro Phe Arg Met Tyr Ile Pro Asn Lys Pro
                        275                 280                 285
        Ser Lys Tyr Gly Ile Lys Ile Leu Met Met Cys Asp Ser Gly Thr Lys
                        290                 295                 300
        Tyr Met Ile Asn Gly Met Pro Tyr Leu Gly Arg Gly Thr Gln Thr Asn
        305                 310                 315                 320
        Gly Val Pro Leu Gly Glu Tyr Val Lys Glu Leu Ser Lys Pro Val
                        325                 330                 335
        His Gly Ser Cys Arg Asn Ile Thr Cys Asp Asn Trp Phe Thr Ser Ile
                        340                 345                 350
        Pro Leu Ala Lys Asn Leu Leu Gln Glu Pro Tyr Lys Leu Thr Ile Val
                        355                 360                 365
        Gly Thr Val Arg Ser Asn Ala Arg Glu Ile Pro Glu Val Leu Lys Asn
                        370                 375                 380
        Ser Arg Ser Arg Pro Val Gly Thr Ser Met Phe Cys Phe Asp Gly Pro
        385                 390                 395                 400
        Leu Thr Leu Val Ser Tyr Lys Pro Lys Pro Ala Lys Met Val Tyr Leu
                        405                 410                 415
        Leu Ser Ser Cys Asp Glu Asp Ala Ser Ile Asn Glu Ser Thr Gly Lys
                        420                 425                 430
        Pro Gln Met Ile Met Tyr Tyr Asn Gln Thr Lys Gly Gly Val Asp Thr
                        435                 440                 445
        Leu Asp Gln Met Cys Ser Val Met Thr Cys Ser Arg Lys Thr Asn Arg
                        450                 455                 460
        Trp Pro Met Ala Leu Leu Tyr Gly Met Ile Asn Ile Ala Cys Ile Asn
        465                 470                 475                 480
        Ser Phe Ile Ile Tyr Ser His Asn Val Ser Ser Lys Gly Glu Lys Val
                        485                 490                 495
        Gln Ser Arg Lys Lys Phe Met Arg Asn Leu Tyr Met Ser Leu Thr Ser
                        500                 505                 510
        Ser Phe Met Arg Lys Arg Leu Glu Ala Pro Thr Leu Lys Arg Tyr Leu
                        515                 520                 525
        Arg Asp Asn Ile Ser Asn Ile Leu Pro Asn Glu Val Pro Gly Thr Ser
        530                 535                 540
        Asp Asp Ser Thr Glu Glu Pro Val Thr Lys Lys Arg Thr Tyr Cys Thr
        545                 550                 555                 560
        Tyr Cys Pro Ser Lys Ile Arg Arg Lys Ala Asn Ala Ser Cys Lys Lys
                        565                 570                 575
        Cys Lys Lys Val Ile Cys Arg Glu His Asn Ile Asp Met Cys Gln Ser
                        580                 585                 590
        Cys Phe

<210> SEQ ID NO 110
<211> LENGTH: 594
<212> TYPE: PRT
<213> ORGANISM: Trichoplusia ni

<400> SEQUENCE: 110

Met Gly Ser Ser Leu Asp Asp Glu His Ile Leu Ser Ala Leu Leu Gln
```

-continued

```
1               5                   10                  15
Ser Asp Asp Glu Leu Val Gly Glu Asp Ser Asp Ser Glu Ile Ser Asp
                20                  25                  30
His Val Ser Glu Asp Val Gln Ser Asp Thr Glu Glu Ala Phe Ile
                35                  40                  45
Asp Glu Val His Glu Val Gln Pro Thr Ser Ser Gly Ser Glu Ile Leu
 50                  55                  60
Asp Glu Gln Asn Val Ile Glu Gln Pro Gly Ser Ser Leu Ala Ser Asn
 65                  70                  75                  80
Lys Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
                100                 105                 110
Asn His Val Arg Ser Gln Arg Gly Pro Thr Arg Met Cys Arg Asn Ile
                115                 120                 125
Tyr Asp Pro Leu Leu Cys Phe Lys Leu Phe Phe Thr Asp Glu Ile Ile
 130                 135                 140
Ser Glu Ile Val Lys Trp Thr Asn Ala Glu Ile Ser Leu Lys Arg Arg
 145                 150                 155                 160
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
                180                 185                 190
His Met Ser Thr Asp Asp Leu Phe Asp Arg Ser Leu Ser Met Val Tyr
                195                 200                 205
Val Ser Val Met Ser Arg Asp Arg Phe Asp Phe Leu Thr Arg Cys Leu
 210                 215                 220
Arg Met Asp Asp Lys Ser Ile Arg Pro Thr Leu Arg Glu Asn Asp Val
 225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
                260                 265                 270
Gly Phe Arg Gly Arg Cys Pro Phe Arg Met Tyr Ile Pro Asn Lys Pro
                275                 280                 285
Ser Lys Tyr Gly Ile Lys Ile Leu Met Met Cys Asp Ser Gly Thr Lys
                290                 295                 300
Tyr Met Ile Asn Gly Met Pro Tyr Leu Gly Arg Gly Thr Gln Thr Asn
 305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
                340                 345                 350
Pro Leu Ala Lys Asn Leu Leu Gln Glu Pro Tyr Lys Leu Thr Ile Val
                355                 360                 365
Gly Thr Val Arg Ser Asn Ala Arg Glu Ile Pro Glu Val Leu Lys Asn
                370                 375                 380
Ser Arg Ser Arg Pro Val Gly Thr Ser Met Phe Cys Phe Asp Gly Pro
 385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
                420                 425                 430
```

```
Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 111
<211> LENGTH: 594
<212> TYPE: PRT
<213> ORGANISM: Trichoplusia ni

<400> SEQUENCE: 111

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205
```

```
Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Pro Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 112
<211> LENGTH: 594
<212> TYPE: PRT
```

-continued

<213> ORGANISM: Trichoplusia ni

<400> SEQUENCE: 112

| | | | | | | | | | | | | | | |
|---|---|---|---|---|---|---|---|---|---|---|---|---|---|---|
| Met | Gly | Ser | Ser | Leu | Asp | Asp | Glu | His | Ile | Leu | Ser | Ala | Leu | Leu | Gln |
| 1 | | | | 5 | | | | | 10 | | | | | 15 | |
| Ser | Asp | Asp | Glu | Leu | Val | Gly | Glu | Asp | Ser | Asp | Ser | Glu | Ile | Ser | Asp |
| | | | 20 | | | | | 25 | | | | | 30 | | |
| His | Val | Ser | Glu | Asp | Asp | Val | Gln | Ser | Asp | Thr | Glu | Glu | Ala | Phe | Ile |
| | | | 35 | | | | | 40 | | | | | 45 | | |
| Asp | Glu | Val | His | Glu | Val | Gln | Pro | Thr | Ser | Ser | Gly | Ser | Glu | Ile | Leu |
| | 50 | | | | | 55 | | | | | 60 | | | | |
| Asp | Glu | Gln | Asn | Val | Ile | Glu | Gln | Pro | Gly | Ser | Ser | Leu | Ala | Ser | Asn |
| 65 | | | | | 70 | | | | | 75 | | | | | 80 |
| Lys | Ile | Leu | Thr | Leu | Pro | Gln | Arg | Thr | Ile | Arg | Gly | Lys | Asn | Lys | His |
| | | | | 85 | | | | | 90 | | | | | 95 | |
| Cys | Trp | Ser | Thr | Ser | Lys | Ser | Thr | Arg | Arg | Ser | Arg | Val | Ser | Ala | Leu |
| | | | | 100 | | | | | 105 | | | | | 110 | |
| Asn | His | Val | Arg | Ser | Gln | Arg | Gly | Pro | Thr | Arg | Met | Cys | Arg | Asn | Ile |
| | | | | 115 | | | | | 120 | | | | | 125 | |
| Tyr | Asp | Pro | Leu | Leu | Cys | Phe | Lys | Leu | Phe | Phe | Thr | Asp | Glu | Ile | Ile |
| | 130 | | | | | 135 | | | | | 140 | | | | |
| Ser | Glu | Ile | Val | Lys | Trp | Thr | Asn | Ala | Glu | Ile | Ser | Leu | Lys | Arg | Arg |
| 145 | | | | | 150 | | | | | 155 | | | | | 160 |
| Glu | Ser | Met | Thr | Gly | Ala | Thr | Phe | Arg | Asp | Thr | Asn | Glu | Asp | Glu | Ile |
| | | | | 165 | | | | | 170 | | | | | 175 | |
| Tyr | Ala | Phe | Phe | Gly | Ile | Leu | Val | Met | Thr | Ala | Val | Arg | Lys | Asp | Asn |
| | | | | 180 | | | | | 185 | | | | | 190 | |
| His | Met | Ser | Thr | Asp | Asp | Leu | Phe | Asp | Arg | Ser | Leu | Ser | Met | Val | Tyr |
| | | | | 195 | | | | | 200 | | | | | 205 | |
| Val | Ser | Val | Met | Ser | Arg | Asp | Arg | Phe | Asp | Phe | Leu | Ile | Arg | Cys | Leu |
| | 210 | | | | | 215 | | | | | 220 | | | | |
| Arg | Met | Asp | Asp | Lys | Ser | Ile | Arg | Pro | Thr | Leu | Arg | Glu | Asn | Asp | Val |
| 225 | | | | | 230 | | | | | 235 | | | | | 240 |
| Phe | Thr | Pro | Val | Arg | Lys | Ile | Trp | Asp | Leu | Phe | Ile | His | Gln | Cys | Ile |
| | | | | 245 | | | | | 250 | | | | | 255 | |
| Gln | Asn | Tyr | Thr | Pro | Gly | Ala | His | Leu | Thr | Ile | Asp | Glu | Gln | Leu | Leu |
| | | | | 260 | | | | | 265 | | | | | 270 | |
| Gly | Phe | Arg | Gly | Arg | Cys | Pro | Phe | Arg | Met | Tyr | Ile | Pro | Asn | Lys | Pro |
| | | | | 275 | | | | | 280 | | | | | 285 | |
| Ser | Lys | Tyr | Gly | Ile | Lys | Ile | Leu | Met | Met | Cys | Asp | Ser | Gly | Thr | Lys |
| | | | | 290 | | | | | 295 | | | | | 300 | |
| Tyr | Met | Ile | Asn | Gly | Met | Pro | Tyr | Leu | Gly | Arg | Gly | Thr | Gln | Thr | Asn |
| 305 | | | | | 310 | | | | | 315 | | | | | 320 |
| Gly | Val | Pro | Leu | Gly | Glu | Tyr | Tyr | Val | Lys | Glu | Leu | Ser | Lys | Pro | Val |
| | | | | 325 | | | | | 330 | | | | | 335 | |
| His | Gly | Ser | Cys | Arg | Asn | Ile | Thr | Cys | Asp | Asn | Trp | Phe | Thr | Ser | Ile |
| | | | | 340 | | | | | 345 | | | | | 350 | |
| Pro | Leu | Ala | Lys | Asn | Leu | Leu | Gln | Glu | Pro | Tyr | Lys | Leu | Thr | Ile | Val |
| | | | | 355 | | | | | 360 | | | | | 365 | |
| Gly | Thr | Val | Arg | Ser | Asn | Ala | Arg | Glu | Ile | Pro | Glu | Val | Leu | Lys | Thr |
| | 370 | | | | | 375 | | | | | 380 | | | | |
| Ser | Arg | Ser | Arg | Pro | Val | Gly | Thr | Ser | Met | Phe | Cys | Phe | Asp | Gly | Pro |
| 385 | | | | | 390 | | | | | 395 | | | | | 400 |

```
Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 113
<211> LENGTH: 594
<212> TYPE: PRT
<213> ORGANISM: Trichoplusia ni

<400> SEQUENCE: 113

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175
```

-continued

```
Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Ser Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Ser Ala Ser Cys Lys Lys
                565                 570                 575

Cys Lys Lys Val Ile Cys Arg Glu His Asn Ile Asp Met Cys Gln Ser
            580                 585                 590

Cys Phe
```

<210> SEQ ID NO 114
<211> LENGTH: 594
<212> TYPE: PRT
<213> ORGANISM: Trichoplusia ni

<400> SEQUENCE: 114

Met Gly Ser Ser Leu Asp Asp Glu His Ile Leu Ser Ala Leu Leu Gln
1               5                   10                  15

Ser Asp Asp Glu Leu Val Gly Glu Ser Asp Ser Glu Ile Ser Asp
            20                  25                  30

His Val Ser Glu Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
            130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn

```
                370             375             380
Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Ala
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 115
<211> LENGTH: 594
<212> TYPE: PRT
<213> ORGANISM: Trichoplusia ni

<400> SEQUENCE: 115

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Val Gln Ser Asp Thr Glu Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
```

```
       145                 150                 155                 160
Glu Ser Met Thr Gly Ala Thr Phe Arg Asp Thr Asn Glu Asp Glu Ile
                    165                 170                 175
Tyr Ala Phe Phe Gly Ile Leu Val Met Thr Ala Val Arg Lys Asp Asn
                    180                 185                 190
His Met Ser Thr Asp Asp Leu Phe Asp Arg Ser Leu Ser Met Val Tyr
                    195                 200                 205
Val Ser Val Met Ser Arg Asp Arg Phe Asp Phe Leu Ile Arg Cys Leu
            210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                    245                 250                 255
Gln Asn Tyr Thr Pro Gly Ala His Leu Thr Ile Asp Glu Gln Leu Leu
                    260                 265                 270
Gly Phe Arg Gly Arg Cys Pro Phe Arg Met Tyr Ile Pro Asn Lys Pro
                    275                 280                 285
Ser Lys Tyr Gly Ile Lys Ile Leu Met Met Cys Asp Ser Gly Thr Lys
            290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                    325                 330                 335
His Gly Ser Cys Arg Asn Ile Thr Cys Asp Asn Trp Phe Thr Ser Ile
                    340                 345                 350
Pro Leu Ala Lys Asn Leu Leu Gln Glu Pro Tyr Lys Leu Thr Ile Val
                    355                 360                 365
Gly Thr Val Arg Ser Asn Ala Arg Glu Ile Pro Glu Val Leu Lys Asn
            370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                    405                 410                 415
Leu Ser Ser Cys Asp Glu Asp Ala Ser Ile Asn Glu Ser Thr Gly Lys
                    420                 425                 430
Pro Gln Met Val Met Tyr Asn Gln Thr Lys Gly Gly Val Asp Thr
                    435                 440                 445
Leu Asp Gln Met Cys Ser Val Met Thr Cys Ser Arg Lys Thr Asn Arg
            450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                    485                 490                 495
Gln Ser Arg Lys Lys Phe Met Arg Asn Leu Tyr Met Ser Leu Thr Ser
                    500                 505                 510
Ser Phe Met Arg Lys Arg Leu Glu Ala Pro Thr Leu Lys Arg Tyr Leu
                    515                 520                 525
Arg Asp Asn Ile Ser Asn Ile Leu Pro Asn Glu Val Pro Gly Thr Ser
            530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Ser Ala Ser Cys Lys Lys
                    565                 570                 575
```

```
Cys Lys Lys Val Ile Cys Arg Glu His Asn Ile Asp Met Cys Gln Ser
            580                 585                 590

Cys Phe

<210> SEQ ID NO 116
<211> LENGTH: 594
<212> TYPE: PRT
<213> ORGANISM: Trichoplusia ni

<400> SEQUENCE: 116

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350
```

-continued

```
Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Asn Gln Thr Lys Gly Gly Val Asp Thr
            435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ala Cys Lys Lys
            565                 570                 575

Cys Lys Lys Val Ile Cys Arg Glu His Asn Ile Asp Met Cys Gln Ser
            580                 585                 590

Cys Phe
```

<210> SEQ ID NO 117
<211> LENGTH: 594
<212> TYPE: PRT
<213> ORGANISM: Trichoplusia ni

<400> SEQUENCE: 117

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125
```

```
Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540
```

-continued

```
Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
        580                 585                 590

Cys Phe

<210> SEQ ID NO 118
<211> LENGTH: 594
<212> TYPE: PRT
<213> ORGANISM: Trichoplusia ni

<400> SEQUENCE: 118

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320
```

Gly Val Pro Leu Gly Glu Tyr Tyr Val Lys Glu Leu Ser Lys Pro Val
              325                 330                 335

His Gly Ser Cys Arg Asn Ile Thr Cys Asp Asn Trp Phe Thr Ser Ile
          340                 345                 350

Pro Leu Ala Lys Asn Leu Leu Gln Glu Pro Tyr Lys Leu Thr Ile Val
          355                 360                 365

Gly Thr Val Arg Ser Asn Ala Arg Glu Ile Pro Glu Val Leu Lys Asn
          370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
              405                 410                 415

Leu Ser Ser Cys Asp Glu Asp Ala Ser Ile Asn Glu Ser Thr Gly Lys
              420                 425                 430

Pro Gln Met Val Met Tyr Tyr Asn Gln Thr Lys Gly Gly Val Asp Thr
              435                 440                 445

Leu Asp Gln Met Cys Ser Val Met Thr Cys Ser Arg Lys Thr Asn Arg
          450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
              485                 490                 495

Gln Ser Arg Lys Lys Phe Met Arg Asn Leu Tyr Met Ser Leu Thr Ser
              500                 505                 510

Ser Phe Met Arg Lys Arg Leu Glu Ala Pro Thr Leu Lys Arg Tyr Leu
          515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
              565                 570                 575

Cys Lys Lys Val Ile Cys Arg Glu His Asn Ile Asp Val Cys Gln Ser
              580                 585                 590

Cys Phe

<210> SEQ ID NO 119
<211> LENGTH: 594
<212> TYPE: PRT
<213> ORGANISM: Trichoplusia ni

<400> SEQUENCE: 119

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
              20                  25                  30

His Val Ser Glu Asp Asp Val Gln Ser Asp Thr Glu Glu Ala Phe Ile
          35                  40                  45

Asp Glu Val His Glu Val Gln Pro Thr Ser Ser Gly Ser Glu Ile Leu
      50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
              85                  90                  95

```
Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Thr Asp Glu Ile Ile
130             135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Ala Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
```

```
            515                 520                 525
Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Val Cys Gln Ser
            580                 585                 590

Cys Phe

<210> SEQ ID NO 120
<211> LENGTH: 594
<212> TYPE: PRT
<213> ORGANISM: Trichoplusia ni

<400> SEQUENCE: 120

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
```

```
            290                 295                 300
Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Arg Ser Asn Ala Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Asn Glu Val Pro Gly Thr Ser
            530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Gly
                580                 585                 590

Cys Phe

<210> SEQ ID NO 121
<211> LENGTH: 594
<212> TYPE: PRT
<213> ORGANISM: Trichoplusia ni

<400> SEQUENCE: 121

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Ala Phe Ile
                35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
```

```
                65                  70                  75                  80
Lys Ile Leu Thr Leu Pro Gln Arg Thr Ile Arg Gly Lys Asn Lys His
                    85                  90                  95

Cys Trp Ser Thr Ser Lys Ser Thr Arg Arg Ser Arg Val Ser Ala Leu
                    100                 105                 110

Asn His Val Arg Ser Gln Arg Gly Pro Thr Arg Met Cys Arg Asn Ile
                    115                 120                 125

Tyr Asp Pro Leu Leu Cys Phe Lys Leu Phe Phe Thr Asp Glu Ile Ile
            130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                    165                 170                 175

Tyr Ala Phe Phe Gly Ile Leu Val Met Thr Ala Val Arg Lys Asp Asn
                    180                 185                 190

His Met Ser Thr Asp Asp Leu Phe Asp Arg Ser Leu Ser Met Val Tyr
                    195                 200                 205

Val Ser Val Met Ser Arg Asp Arg Phe Asp Phe Leu Ile Arg Cys Leu
            210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                    245                 250                 255

Gln Asn Tyr Thr Pro Gly Ala His Leu Thr Ile Asp Glu Gln Leu Leu
                    260                 265                 270

Gly Phe Arg Gly Arg Cys Pro Phe Arg Met Tyr Ile Pro Asn Lys Pro
                    275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                    325                 330                 335

His Gly Ser Cys Arg Asn Ile Thr Cys Asp Asn Trp Phe Thr Ser Ile
                    340                 345                 350

Pro Leu Ala Lys Asn Leu Leu Gln Glu Pro Tyr Lys Leu Thr Ile Val
                    355                 360                 365

Gly Thr Val Arg Ser Asn Ala Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                    405                 410                 415

Leu Ser Ser Cys Asp Glu Asp Ala Ser Ile Asn Glu Ser Thr Gly Lys
                    420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                    485                 490                 495
```

```
Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
        530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Leu

<210> SEQ ID NO 122
<211> LENGTH: 600
<212> TYPE: PRT
<213> ORGANISM: Trichoplusia ni

<400> SEQUENCE: 122

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270
```

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe Trp Leu Glu Ser Cys Asn
        595                 600

<210> SEQ ID NO 123
<211> LENGTH: 600
<212> TYPE: PRT
<213> ORGANISM: Trichoplusia ni

<400> SEQUENCE: 123

Met Gly Ser Ser Leu Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile

-continued

```
                35                  40                  45
Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Lys Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
                115                 120                 125

Tyr Asp Pro Leu Leu Cys Phe Lys Leu Phe Phe Thr Asp Glu Ile Ile
                130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
                290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Arg Ser Asn Ala Arg Glu Ile Pro Glu Val Leu Lys Asn
                370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460
```

Trp Pro Met Ala Leu Leu Tyr Gly Met Ile Asn Ile Ala Cys Ile Asn
465                 470                 475                 480

Ser Phe Ile Ile Tyr Ser His Asn Val Ser Lys Gly Glu Lys Val
            485                 490                 495

Gln Ser Arg Lys Lys Phe Met Arg Asn Leu Tyr Met Ser Leu Thr Ser
        500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe Glu Leu Glu Ser Cys Asn
            595                 600

<210> SEQ ID NO 124
<211> LENGTH: 600
<212> TYPE: PRT
<213> ORGANISM: Trichoplusia ni

<400> SEQUENCE: 124

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val

```
            225                 230                 235                 240
        Phe Thr Pro Val Arg Lys Ile Trp Asp Leu Phe Ile His Gln Cys Ile
                        245                 250                 255
        Gln Asn Tyr Thr Pro Gly Ala His Leu Thr Ile Asp Glu Gln Leu Leu
                        260                 265                 270
        Gly Phe Arg Gly Arg Cys Pro Phe Arg Met Tyr Ile Pro Asn Lys Pro
                        275                 280                 285
        Ser Lys Tyr Gly Ile Lys Ile Leu Met Met Cys Asp Ser Gly Thr Lys
                        290                 295                 300
        Tyr Met Ile Asn Gly Met Pro Tyr Leu Gly Arg Gly Thr Gln Thr Asn
        305                 310                 315                 320
        Gly Val Pro Leu Gly Glu Tyr Val Lys Glu Leu Ser Lys Pro Val
                        325                 330                 335
        His Gly Ser Cys Arg Asn Ile Thr Cys Asp Asn Trp Phe Thr Ser Ile
                        340                 345                 350
        Pro Leu Ala Lys Asn Leu Leu Gln Glu Pro Tyr Lys Leu Thr Ile Val
                        355                 360                 365
        Gly Thr Val Ala Ser Asn Lys Arg Glu Ile Pro Glu Val Leu Lys Asn
        370                 375                 380
        Ser Arg Ser Arg Pro Val Gly Thr Ser Met Phe Cys Phe Asp Gly Pro
        385                 390                 395                 400
        Leu Thr Leu Val Ser Tyr Lys Pro Lys Pro Ala Lys Met Val Tyr Leu
                        405                 410                 415
        Leu Ser Ser Cys Asp Glu Asp Ala Ser Ile Asn Glu Ser Thr Gly Lys
                        420                 425                 430
        Pro Gln Met Val Met Tyr Tyr Asn Gln Thr Lys Gly Gly Val Asp Thr
                        435                 440                 445
        Leu Asp Gln Met Cys Ser Val Met Thr Cys Ser Arg Lys Thr Asn Arg
                        450                 455                 460
        Trp Pro Met Ala Leu Leu Tyr Gly Met Ile Asn Ile Ala Cys Ile Asn
        465                 470                 475                 480
        Ser Phe Ile Ile Tyr Ser His Asn Val Ser Ser Lys Gly Glu Lys Val
                        485                 490                 495
        Gln Ser Arg Lys Lys Phe Met Arg Asn Leu Tyr Met Ser Leu Thr Ser
                        500                 505                 510
        Ser Phe Met Arg Lys Arg Leu Glu Ala Pro Thr Leu Lys Arg Tyr Leu
                        515                 520                 525
        Arg Asp Asn Ile Ser Asn Ile Leu Pro Asn Glu Val Pro Gly Thr Ser
        530                 535                 540
        Asp Asp Ser Thr Glu Glu Pro Val Thr Lys Lys Arg Thr Tyr Cys Thr
        545                 550                 555                 560
        Tyr Cys Pro Ser Lys Ile Arg Arg Lys Ala Asn Ala Ser Cys Lys Lys
                        565                 570                 575
        Cys Lys Lys Val Ile Cys Arg Glu His Asn Ile Asp Met Cys Gln Ser
                        580                 585                 590
        Cys Phe Trp Leu Thr Asn Lys Tyr
                        595                 600

<210> SEQ ID NO 125
<211> LENGTH: 600
<212> TYPE: PRT
<213> ORGANISM: Trichoplusia ni

<400> SEQUENCE: 125
```

```
Met Gly Ser Ser Leu Asp Asp Glu His Ile Leu Ser Ala Leu Leu Gln
1               5                   10                  15

Ser Asp Asp Glu Leu Val Gly Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
                100                 105                 110

Asn His Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
    195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
```

```
                    420                 425                 430
Pro Gln Met Val Met Tyr Tyr Asn Gln Thr Lys Gly Gly Val Asp Thr
            435                 440                 445
Leu Asp Gln Met Cys Ser Val Met Thr Cys Ser Arg Lys Thr Asn Arg
        450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe Trp Leu Thr Asn Lys Tyr
        595                 600

<210> SEQ ID NO 126
<211> LENGTH: 600
<212> TYPE: PRT
<213> ORGANISM: Trichoplusia ni

<400> SEQUENCE: 126

Met Gly Ser Ser Leu Asp Asp Glu His Ile Leu Ser Ala Leu Leu Gln
1               5                   10                  15
Ser Asp Asp Glu Leu Val Gly Glu Asp Ser Asp Ser Glu Ile Ser Asp
                20                  25                  30
His Val Ser Glu Asp Val Gln Ser Asp Thr Glu Glu Ala Phe Ile
            35                  40                  45
Asp Glu Val His Glu Val Gln Pro Thr Ser Ser Gly Ser Glu Ile Leu
        50                  55                  60
Asp Glu Gln Asn Val Ile Glu Gln Pro Gly Ser Ser Leu Ala Ser Asn
65                  70                  75                  80
Lys Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
            100                 105                 110
Asn His Val Arg Ser Gln Arg Gly Pro Thr Arg Met Cys Arg Asn Ile
        115                 120                 125
Tyr Asp Pro Leu Leu Cys Phe Lys Leu Phe Thr Asp Glu Ile Ile
130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
            180                 185                 190
```

-continued

```
His Met Ser Thr Asp Asp Leu Phe Asp Arg Ser Leu Ser Met Val Tyr
            195                 200                 205
Val Ser Val Met Ser Arg Asp Arg Phe Asp Phe Leu Ile Arg Cys Leu
210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Thr Lys
290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Ala Ser Asn Lys Arg Glu Ile Pro Glu Val Leu Lys Asn
370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Asn Glu Val Pro Gly Thr Ser
530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
            580                 585                 590
Cys Phe Gly Leu Thr Asn Lys Tyr
        595                 600
```

<210> SEQ ID NO 127
<211> LENGTH: 600
<212> TYPE: PRT
<213> ORGANISM: Trichoplusia ni

<400> SEQUENCE: 127

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Ala Arg Glu Ile Pro Glu Val Leu Lys Asn
370                 375                 380
```

```
Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe Gly Leu Thr Asn Lys Tyr
        595                 600

<210> SEQ ID NO 128
<211> LENGTH: 6
<212> TYPE: PRT
<213> ORGANISM: Trichoplusia ni

<400> SEQUENCE: 128

Trp Leu Glu Ser Cys Asn
1               5

<210> SEQ ID NO 129
<211> LENGTH: 6
<212> TYPE: PRT
<213> ORGANISM: Trichoplusia ni

<400> SEQUENCE: 129

Glu Leu Glu Ser Cys Asn
1               5

<210> SEQ ID NO 130
<211> LENGTH: 6
<212> TYPE: PRT
<213> ORGANISM: Trichoplusia ni

<400> SEQUENCE: 130

Gly Leu Glu Ser Cys Asn
1               5
```